US009388138B2

(12) United States Patent
Kennedy et al.

(10) Patent No.: US 9,388,138 B2
(45) Date of Patent: Jul. 12, 2016

(54) ANTI-ANGIOGENIC COMPOUNDS

(71) Applicants: University College Dublin National University of Ireland, Dublin, Dublin (IE); The Provost, Fellows, Foundation Scholars, and the other members of Board, of the College of the Holy, Dublin (IE)

(72) Inventors: Breandan Douglas Kennedy, Dublin (IE); Alison Reynolds, Dublin (IE); Claire Kilty, Dublin (IE); Jacintha O'Sullivan, Dublin (IE); Andrew Douglas Baxter, West Sussex (GB)

(73) Assignees: UNIVERSITY COLLEGE DUBLIN NATIONAL UNIVERSITY OF IRELAND, DUBLIN, Dublin (IE); THE PROVOST, FELLOWS, FOUNDATION SCHOLARS, AND THE OTHER MEMEBERS OF BOARD, OF THE COLLEGES OF THE HOLY AND UNDIVIDED TRINITY OF QUEEN ELIZABETH NEAR DUBLIN, Dublin (IE)

( * ) Notice: Subject to any disclaimer, the term of this patent is extended or adjusted under 35 U.S.C. 154(b) by 0 days.

(21) Appl. No.: 14/415,078

(22) PCT Filed: Jul. 15, 2013

(86) PCT No.: PCT/EP2013/064911
§ 371 (c)(1),
(2) Date: Jan. 15, 2015

(87) PCT Pub. No.: WO2014/012889
PCT Pub. Date: Jan. 23, 2014

(65) Prior Publication Data
US 2015/0218100 A1 Aug. 6, 2015

(30) Foreign Application Priority Data
Jul. 18, 2012 (IE) .................................. 2012/0321

(51) Int. Cl.
*C07D 215/38* (2006.01)
*A61K 31/47* (2006.01)
*C07D 215/14* (2006.01)
*A61K 31/4725* (2006.01)

(52) U.S. Cl.
CPC ............... *C07D 215/14* (2013.01); *A61K 31/47* (2013.01); *A61K 31/4725* (2013.01)

(58) Field of Classification Search
CPC . A61K 31/47; A61K 31/4725; C07D 215/38; C07D 215/14
See application file for complete search history.

(56) References Cited

U.S. PATENT DOCUMENTS 4,130,650 A * 12/1978 Muller ................. A61K 31/135
514/351
8,916,586 B2 * 12/2014 Kennedy ............ A61K 31/4725
514/186

FOREIGN PATENT DOCUMENTS

WO       2012/095836 A1      7/2012

OTHER PUBLICATIONS

Forschungsinst, CA 69:51946, abstract only of Tetrahedron, vol. 24(14), p. 5023-5027, 1968.*
Tak, CA 77:47548, abstract only of J of the Indian Chem Soc, vol. 49(2), p. 139-144, 1972.*
Alvarez et al., "Selective Inhibition of Retinal Angiogenesis by Targeting PI3 Kinase", PLoSONE 4(11): e7867. doi:10.1371/journal.pone.0007867, Nov. 2009.
Alvarez et al., "Genetic determinants of hyaloid and retinal vasculature in zebrafish", BMC evelopmental Biology 2007, 7:114 doi:10.1186/1471-213X-7-114, Oct. 15, 2007.
Bergers et al., "Tumorigenesis and the Angiogenic Switch", Nature Publishing Group, doi:10.1038/nrc1093, vol. 3, pp. 401-410, Jun. 2003.
Bergers et al., "Modes of resistance to antiangiogenic therapy", Macmillan Publishers Limited, doi:10.1038/nrc2442, vol. 8, pp. 592-603, Aug. 2008.
Brockerhoff, "Measuring the optokinetic response of zebrafish larvae", Nature Protocols, doi:10.1038/nprot.2006.255, vol. 1 No. 5, pp. 2448-2451, Dec. 29, 2006.
Carmeliet, "VEGF as a Key Mediator of Angiogenesis in Cancer", Oncology, DOI: 10.1159/000088478, 69(suppl 3): pp. 4-10, Nov. 21, 2005.
Culy, "Bevacizumab Antiangiogenic cancer therapy", Drugs of Today 2005, 41 (1): pp. 23-36, CCC: 0025-7656/2005.
Hertog, "Chemical Genetics: Drug Screens in Zebrafish", Bioscience Reports, DOI: 10.1007/s10540-005-2891-8 , vol. 25, Nos. 5/6, pp. 289-297, Oct./Dec. 2005.
Doukas et al., "Topical Administration of a Multi-Targeted Kinase Inhibitor Suppresses Choroidal Neovascularization and Retinal Edema", J Cell Physiol, 216(1): 29-37. doi:10.1002/jcp.21426, Jul. 2008.
Ellis, "Antiangiogenic Therapy at a Crossroads: Clinical Trial Results and Future Directions", Journal of Clinical Oncology, DOI: 10.1200/JCO.2003.09.134, vol. 21, No. 23s: pp. 281s-283s, (Dec. 1 Supplement), 2003.
Ferrara, "Vascular endothelial growth factor and age-related macular degeneration: from basic science to therapy", nature medicine, vol. 16, No. 10, pp. 1107-1111, Oct. 2010.
Ferrara et al., "Angiogenesis as a therapeutic target", Nature, doi:10.1038/nature04483, vol. 438, pp. 967-974, Dec. 15, 2005.
Frank, "Diabetic Retinopathy", The New England Journal of Medicine, 350;1, pp. 48-58, Jan. 1, 2004.
Goldsmith, "Zebrafish as a pharmacological tool: the how, why and when", Current Opinion in Pharmacology, DOI 10.1016/j.coph.2004.04.005, vol. 4, pp. 504-512, Jul. 20, 2004.

(Continued)

*Primary Examiner* — D M Seaman
(74) *Attorney, Agent, or Firm* — Jacobson Holman, PLLC.

(57) ABSTRACT

(E)-2-(2-Quinolin-2-yl-propenyl)-phenol, 2-Quinolin-2-yl-ylethynyl-phenol and salts thereof are useful as medicaments, especially for treatment of an angiogenesis-related disease or disorder.

20 Claims, 50 Drawing Sheets

(56) References Cited

OTHER PUBLICATIONS

He et al., "Biologic Therapy for Colon Cancer", Clinical Advances in Hematology & Oncology vol. 3, pp. 555-561, Jul. 7, 2005.

Jager et al., "Age-Related Macular Degeneration", The New England Journal of Medicine, 358;24, pp. 2606-2617, Jun. 12, 2008.

Kleinman et al., "Sequence- and target-independent angiogenesis suppression by siRNA via TLR3", Nature, doi:10.1038/nature06765, vol. 452, pp. 591-598, Apr. 3, 2008.

MacRae et al., "Zebrafish-Based Small Molecule Discovery", Chemistry & Biology, DOI 10.1016/j.chembiol.2003.10.003, vol. 10, pp. 901-908, Oct. 2003.

Mandalà et al., "Oxaliplatin in Colon Cancer", The New England Journal of Medicine, 351;16, pp. 1691-92, Oct. 14, 2004.

Narayanan et al., "Ranibizumab", Nature Reviews, Drug Discovery, vol. 5, pp. 815-816, Oct. 2006.

Peterson et al., "Chemical suppression of a genetic mutation in a zebrafish model of aortic coarctation", Nature Biotechnology, doi:10.1038/nbt963, vol. 22, No. 5, pp. 595-599, Apr. 18, 2004.

Pichler et al., "Chemical discovery and global gene expression analysis in zebrafish", Nature Biotechnology, vol. 21, No. 8, pp. 879-883, Aug. 2003.

Rattner et al., "Macular degeneration: recent advances and therapeutic opportunities", Nature, doi:10.1038/nrn2007, vol. 7, pp. 860-872, Oct. 11, 2006.

Takahashi et al., "The Multi-targeted Kinase Inhibitor Pazopanib Causes Suppression and Regression of Choroidal Neovascularization", Arch Ophthalmol, 127(4): pp. 494-499, doi:10.1001/archophthalmol.2009.27, Apr. 2009.

Wong, "Cetuximab: An Epidermal Growth Factor Receptor Monoclonal Antibody for the Treatment of Colorectal Cancer", Clinical Therapeutics, doi: 10.1016/j.clinthera.2005.06.003, vol. 27, pp. 684-694, No. 6, 2005.

Zon et al., "In Vivo Drug Discovery in the Zebrafish", Nature Reviews, Drug Discovery, doi:10.1038/nrd1606, vol. 4, pp. 35-44, Jan. 2005.

Bahner et al., "Di- and Tri-methoxystyryl Derivatives of Heterocyclic Nitrogen Compounds", Arzneim Forsch, Drug Res. 31 (1), Nr.3, pp. 404-406, 1981.

Zamboni et al., "Development of a Novel Series of Styrylquinoline Compounds as High-Affinity Leukotriene D4 Receptor Antagonists: Synthetic and Structure-Activity Studies Leading to the Discovery of . . . ", J.Med. Chem. 1992, 35, pp. 3832-3844, Apr. 6, 1992.

\* cited by examiner

| Assay Type | % inhibition of each compound | |
|---|---|---|
| | 11B_CC11_HCl | 11B_CC16_HCl |
| CysLT1 (LTD4) antagonist assay (cell based) | 137 | 137 |
| CysLT1 (LTD4) antagonist assay (GP lung) | | 100 |
| CysLT2 (LTC4) antagonist assay (cell based) | 41 | 48 |

11A (5-bromo-N'-[2-(trifluoromethyl)benzylidene]-2-furohydrazide)

11C (3-(1,3-benzodioxol-5-yl)-N-(3-pyridinylmethyl)acrylamide)

ANTI-ANGIOGENIC COMPOUNDS

INTRODUCTION

The invention relates to anti-angiogenic compounds.

In many human diseases there is an inappropriate growth of new blood vessels (angiogenesis). Angiogenesis is a physiological process involving the growth of new blood vessels from pre-existing vessels (Ferrara and Kerbel, 2005). Angiogenesis may be a therapeutic target for combating diseases characterised by poor vascularisation or abnormal vasculature (Ferrara and Kerbel, 2005). Targeted administration of specific compounds that may inhibit (anti-angiogenesis) or induce (pro-angiogenesis) the creation of new blood vessels in the body may help combat such diseases.

Diabetic retinopathy (DR) is the most feared complication of diabetes, compromising the quality of life in most sufferers (Frank, 2004). About 30% of type 1 diabetes patients advance to the blinding stage of the disease and about 60% of type 2 diabetes patients develop retinopathy. DR is the most common cause of vision impairment in people of working age in Western society and is likely to increase in prevalence as it has been projected that about 360 million people will suffer from diabetes by 2030. Diabetic macular oedema is the principal cause of vision loss in diabetes and involves leakage from a disrupted blood-retinal barrier.

Age-related macular degeneration (AMD) is a leading cause of vision loss in the western world among people aged 50 or older (Rattner and Nathans, 2006; Jager et al., 2008). Ninety percent of vision loss due to AMD results from the exudative form, which is characterized by newly formed blood vessels arising from capillaries in the choroid layer adjacent to the retina.

Current approaches for resolving inappropriate growth of new vessels in the eye include laser treatment and molecular therapies targeted to vascular endothelial cell growth factor (VEGF) (Ferrara; Rattner and Nathans, 2006; Jager et al., 2008).

Photodynamic therapy (PDT) is a laser-based surgery for wet age-related macular degeneration. In PDT a light-sensitive dye is injected intravenously. A low energy laser beam is directed onto the target vessels. This makes the chemical react and destroy the leaking blood vessels without damaging adjacent healthy tissue however, multiple treatments are usually required and PDT is unsuitable for long-established wet age-related macular degeneration and cannot restore sight already lost to age-related macular degeneration.

There are a number of variations of VEGF molecular therapy but those in clinical use are antibodies targeted to VEGF which stop the development of new leaky blood vessels. Treatment requires intraocular injection by retinal specialists, needs to be repeated every six weeks and requires the patient to be sedated. In some cases, VEGF treatment has been shown to restore some visual acuity.

In diabetic retinopathy, laser ablation of the new vessels is routinely performed however laser ablation locally destroys the retina. In age-related macular degeneration monoclonal antibodies attenuating VEGF signalling are used clinically (Macugen, Lucentis), however the monoclonal antibodies are very expensive to manufacture/administer and patients require monthly intravitreal injections (Narayanan et al., 2006). Armala (pazopanib) is a multi-kinase (VEGF, PDGF, c-kit) angiogenesis inhibitor in clinical trials for AMD and cancer (Takahashi et al., 2009). siRNA targeting VEGF have also been used in clinical trials, however the siRNAs to VEGF have been found to act by a non-specific mechanism (Kleinman et al., 2008).

Cancer can originate in many tissues including the bowel, breast and skin. Obviously, with the prevalence and incurability of cancer types, there is a real need to develop new therapeutics. It is now widely accepted that the growth of solid tumours is dependent on their capacity to acquire a blood supply (Bergers and Benjamin, 2003). Indeed, much effort has been directed towards the development of anti-angiogenics that disrupt this process in tumours. In contrast to traditional anti-cancer agents that directly destroy tumour cells, mediating a cytocidal effect, anti-angiogenics are generally regarded as cytostatic agents. Another emerging feature of the use of anti-angiogenics in cancer treatment is the phenomenon of resistance (Bergers and Hanahan, 2008). In both animal models and humans, the benefits of anti-angiogenic therapy are at best transitory and commonly followed by a restoration of tumour growth and progression. As such, there is a pressing need to find multiple target points for anti-angiogenic therapy, so as to provide additional opportunities to pre-empt such resistance phenomena emerging.

Of particular relevance is Colorectal Cancer (CRC) which accounts for 10-15% of all cancers and is the leading cause of cancer deaths in the Western world (Mandala et al., 2004). Colorectal cancer is the commonest internal cancer in the Western World. It is a major cause of morbidity and mortality, with approximately 50 percent dying from their disease within 5 years of diagnosis. Contemporary chemotherapy treatments are effective in many cases but extremely expensive and potentially dangerous.

Current treatments for colorectal cancer patients are complex. Multidisciplinary teams must decide who will benefit from expensive new treatments. Currently, treatment decisions for patients depend solely on pathological staging. The chemotherapeutic agents Fluorouracil (5-FU) plus leucovorin (LV) have been the mainstay treatment for CRC. Newer drugs such as oxaliplatin, capecitabine and irinotecan have significantly improved response rates, time to progression and increase survival rates in patients with advanced CRC (Mandala et al., 2004). However, even with these new drug combinations, the long term prognosis remains poor for late-stage CRC patients with metastatic lesions.

Over the last few years, new monoclonal antibody therapies targeting key angiogenic molecules including: bevacizumab (Avastin, anti-VEGF) and cetuximab (Erbitux, anti-EGFR) (Culy, 2005; He and Marshall, 2005) have been introduced to fight late-stage CRC and improve outcome (Ellis, 2003). Bevacizumab (Avastin) blocks vascular endothelial growth factor (VEGF) by preventing the interaction of VEGF with its' receptors [VEGFR-1 (Flt-1) and VEGFR-2 (KDR)]. Pre-clinical studies suggest that bevacizumab acts by inhibiting tumour neo-vascularisation and when used in combination with chemotherapeutic drugs, it increases the permeability of tumours to chemotherapy (Ellis, 2003). Cetuximab (Erbitux) inhibits the epidermal growth factor receptor (EGFR) signalling cascade (Wong, 2005) and tumours that over-express EGFR have a poor prognosis. Erbitux also inhibits angiogenesis inside tumours, leading to an overall suppression of tumour growth (Carmeliet, 2005). Pre-clinical data indicate that Erbitux has anti-tumour activity in colon cancer xenografts and can reduce the production of VEGF, interleukin-8 (IL-8), and basic fibroblast growth factor (bFGF). Currently, these molecular therapies are solely given to late-stage metastatic CRC patients

STATEMENTS OF INVENTION

According to the invention there is provided compound selected from:

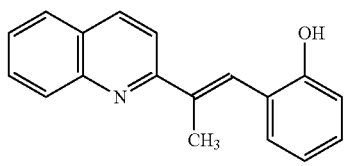

Structure IV

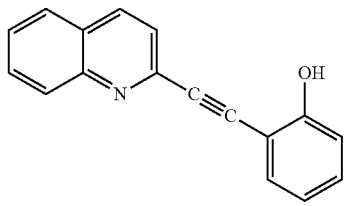

Structure VI and salts thereof.

In one case salt is a HCl salt.

The invention also provides compound selected from:

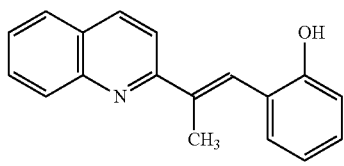

Structure IV

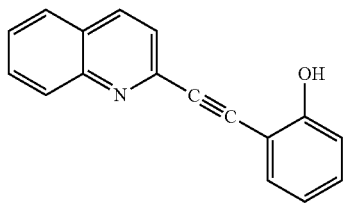

Structure VI and salts thereof for use as a medicament.

Further provided is a compound selected from:

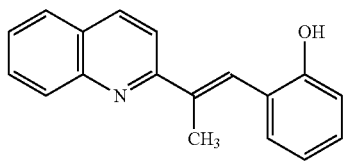

Structure IV

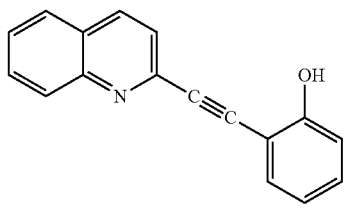

Structure VI and salts thereof for use in the treatment of an angiogenesis-related disease or disorder.

The salt may be a HCl salt of the compound.

The angiogenesis-related disease or disorder may be associated with neovascularisation of the eye. In one case the angiogenesis-related disease or disorder is associated with blindness. The angiogenesis-related disease or disorder may be age-related macular degeneration or diabetic retinopathy. The age-related macular degeneration may be wet age-related macular degeneration.

In one embodiment the angiogenesis-related disease or disorder is cancer. The cancer may be a solid tumour forming cancer.

The cancer may be colorectal cancer, oesophageal cancer, or breast cancer.

The invention also provides a pharmaceutical composition comprising one or more compound selected from:

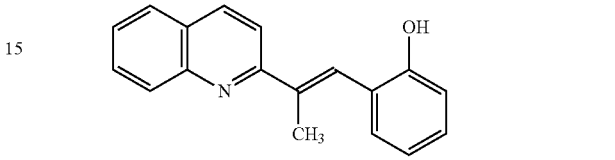

Structure IV

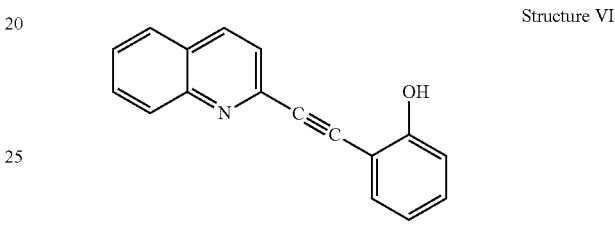

Structure VI and salts thereof

The salt may be a HCl salt of the compound.

The composition may comprise a pharmaceutically acceptable excipient. The composition may be in a form for topical administration. The composition may be in the form of eye drops. The composition may be in a form for systemic administration. In one case the composition is in the form of an injectable solution or suspension.

Also provided is use of a composition of the invention in the treatment of an angiogenesis-related disease or disorder. The angiogenesis-related disease or disorder may be associated with neovascularisation of the eye. The angiogenesis-related disease or disorder may be associated with blindness. The angiogenesis-related disease or disorder may be age-related macular degeneration or diabetic retinopathy. The age-related macular degeneration may be wet age-related macular degeneration. The angiogenesis-related disease or disorder may be cancer. The cancer may be a solid tumour forming cancer. The cancer may be colorectal cancer. The cancer may be oesophageal cancer. The cancer may be breast cancer.

Also provided is a compound of the invention for use in treating cancer. The cancer may be a solid tumour forming cancer. The cancer may be colorectal cancer, oesophageal cancer, or breast cancer.

The invention also provides a compound of the formula

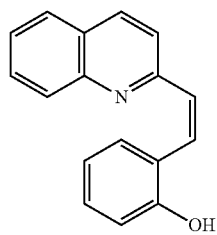 [SMILES: Oc1ccccc1/C=C\c1ccc2ccccc2n1]

or a salt thereof, particularly the HCl salt, pharmaceutical compositions comprising the compound and use thereof as a medicament. The compound may be used in the treatment of an angiogenesis-related disease or disorder. In one case the disease or disorder is associated with blindness. The angiogenesis-related disease or disorder may be age-related macular degeneration or diabetic retinopathy such as wet age-related macular degeneration. The compound may be used for the treatment of cancer which may be a solid tumour forming cancer such as colorectal cancer. The compound may be used for the treatment of oesophageal cancer or breast cancer.

The invention further provides a compound for the formula

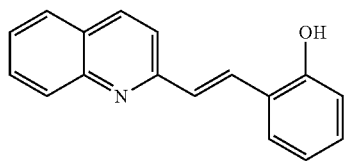 [SMILES: Oc1ccccc1/C=C/c1ccc2ccccc2n1]

or a salt thereof especially the HCl salt for use in the treatment of oesophageal cancer or breast cancer.

The invention also provides a compound selected from:

Structure I
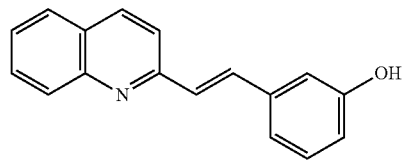

Structure II
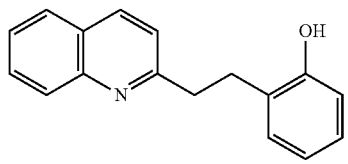

Structure III
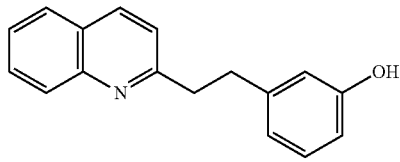

Structure IV
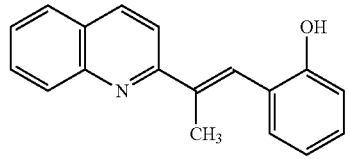

Structure V
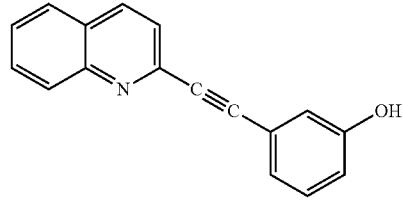

Structure VI
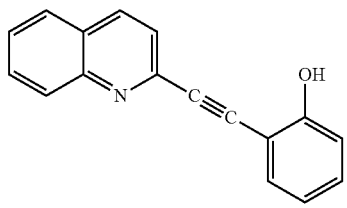

Structure VII
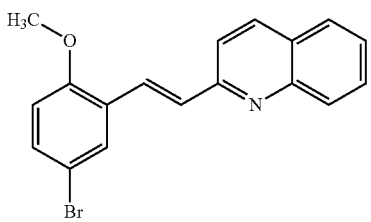

Structure VIII
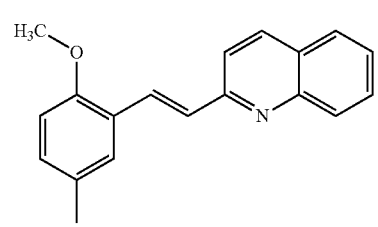

Structure IX
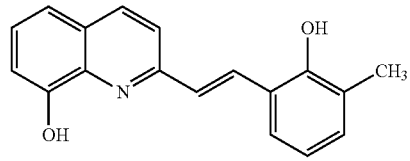

Structure X
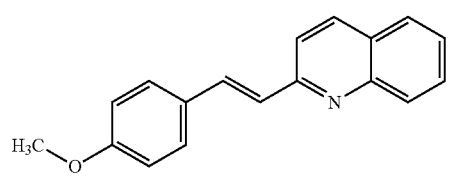

Structure XI
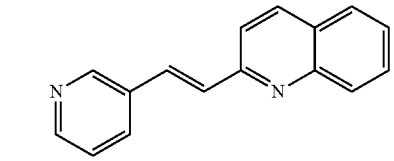

Structure XII
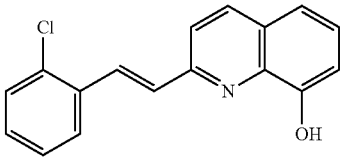

Structure XIII
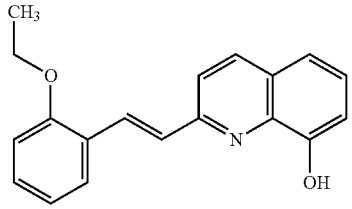

-continued

Structure XIV

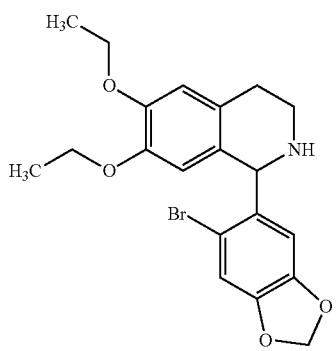

Structure XV

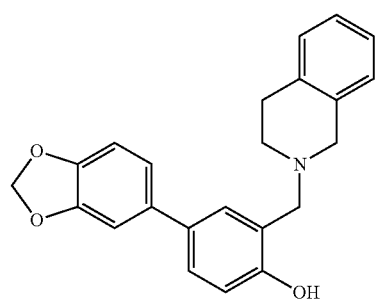

Structure XVI

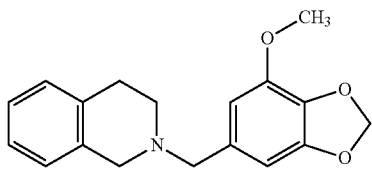

Structure XVII

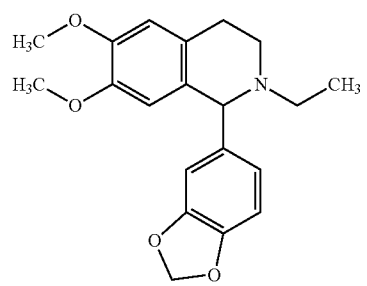

and salts thereof for use in the treatment of an angiogenesis-related disease or disorder. The salt may be a HCl salt of the compound.

The invention also provides a compound selected from:

Structure XVIII

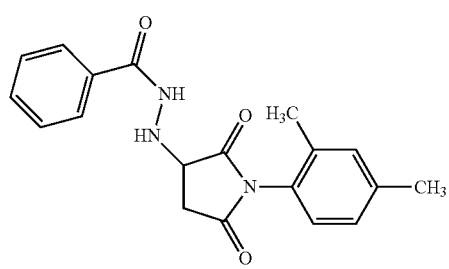

-continued

Structure XIX

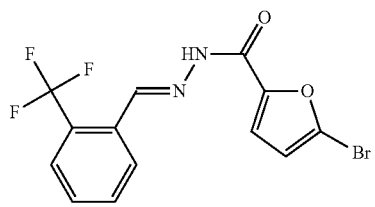

Structure XX

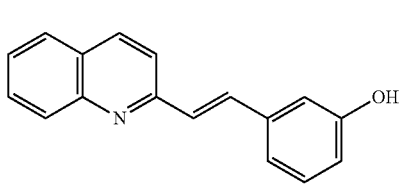

and salts thereof for use in the treatment of an angiogenesis-related disease or disorder.

The angiogenesis-related disease or disorder may be associated with neovascularisation of the eye. The angiogenesis-related disease or disorder may be associated with blindness. The angiogenesis-related disease or disorder may be age-related macular degeneration or diabetic retinopathy. The age-related macular degeneration may be wet age-related macular degeneration.

The angiogenesis-related disease or disorder may be cancer. The cancer may be a solid tumour forming cancer such as colorectal cancer.

The compounds described herein may be used for the treatment of cancer, in particular colorectal cancer, oesophageal cancer or breast cancer.

The compounds described herein may be used for the treatment of undesirable inflammation.

The invention further provides a pharmaceutical composition comprising one or more compound selected from:

Structure I

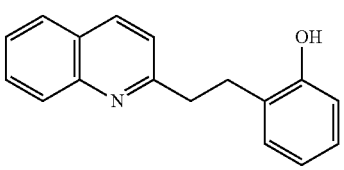

Structure II

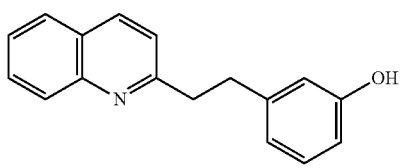

Structure III

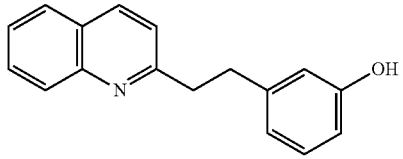

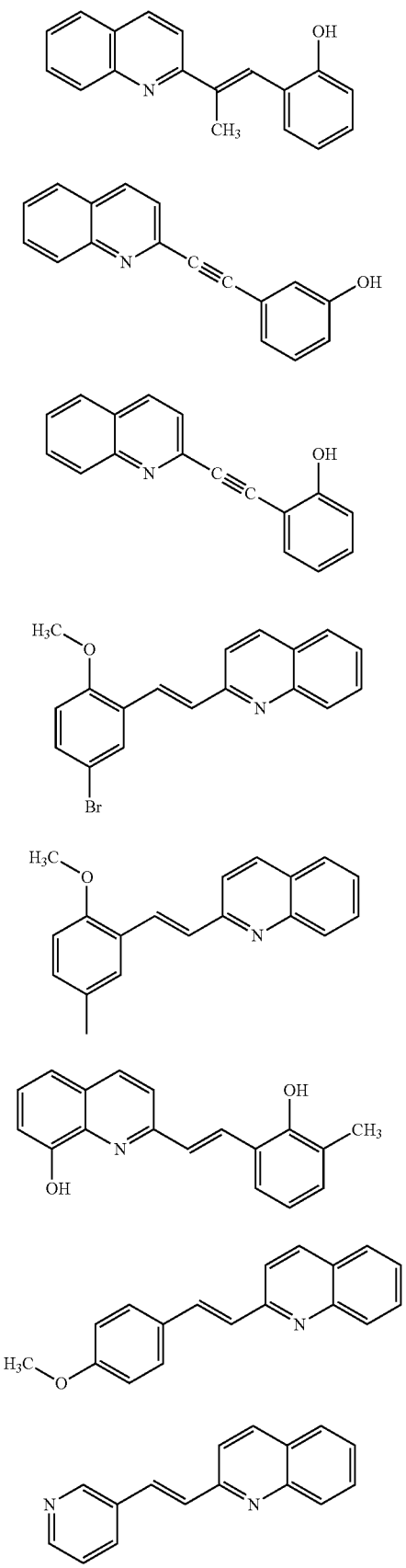

Structure IV

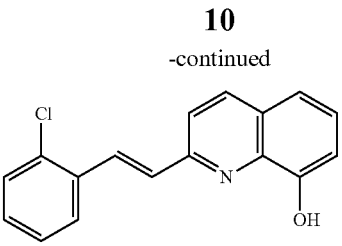

Structure V

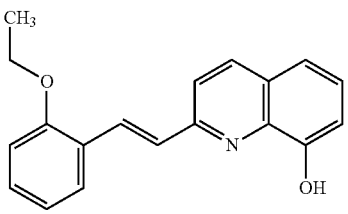

Structure VI

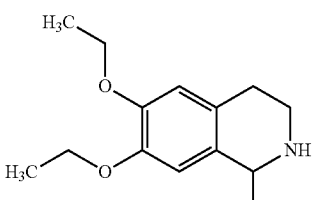

Structure VII

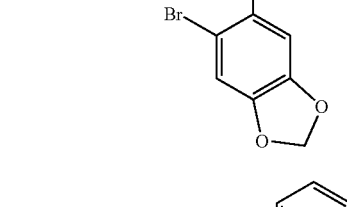

Structure VIII

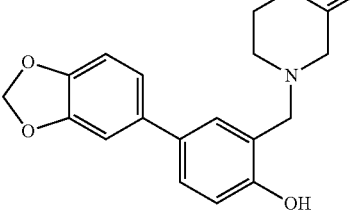

Structure IX

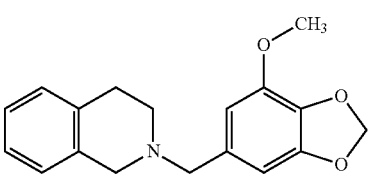

Structure X

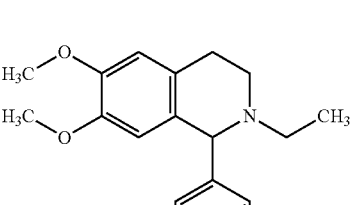

Structure XI

Structure XII

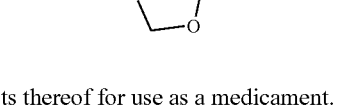

Structure XIII

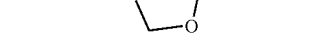

Structure XIV

Structure XV

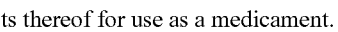

Structure XVI

Structure XVII and salts thereof for use as a medicament. The salt may be a HCl salt of the compound.

The invention also provides a pharmaceutical composition comprising one or more compound selected from:

Structure XVIII

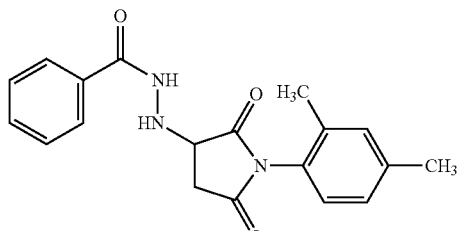

Structure XIX

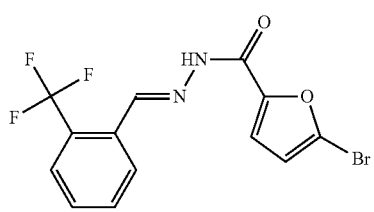

Structure XX

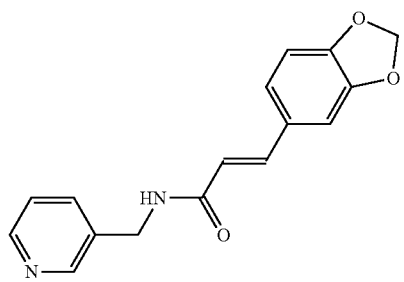

and salts thereof for use as a medicament.

The composition may comprise a pharmaceutically acceptable excipient.

The composition may be in a form for topical administration such as in the form of eye drops.

The composition may be in a form for systemic administration such as in the form of an injectable solution or suspension.

The invention also provides for the use of a compositions described herein in the treatment of an angiogenesis-related disease or disorder. The angiogenesis-related disease or disorder may associated with neovascularisation of the eye. The angiogenesis-related disease or disorder may be associated with blindness. The angiogenesis-related disease or disorder may be age-related macular degeneration or diabetic retinopathy. The age-related macular degeneration may be wet age-related macular degeneration.

The angiogenesis-related disease or disorder may be cancer. The cancer may be a solid tumour forming cancer such as colorectal cancer.

The compositions described herein may be used for the treatment of undesirable inflammation.

The invention also provides a compound of:

Structure I

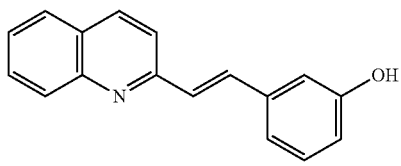

or salt thereof

The invention further provides a compound of:

Structure II

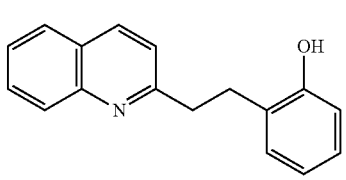

or salt thereof

The invention further provides a compound of:

Structure III

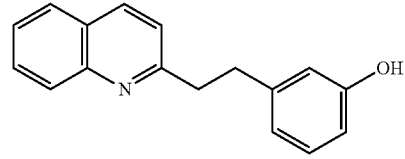

or salt thereof.

The invention further provides a compound of:

Structure IV

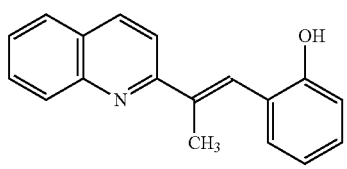

or salt thereof.

The invention further provides a compound of:

Structure V

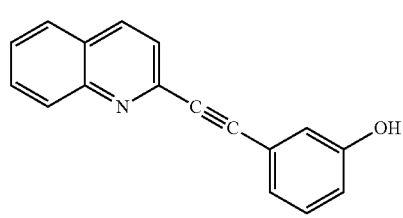

or salt thereof

The invention further provides a compound of:

Structure VI

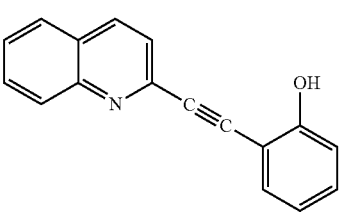

or salt thereof.

The invention also provides a compound of:

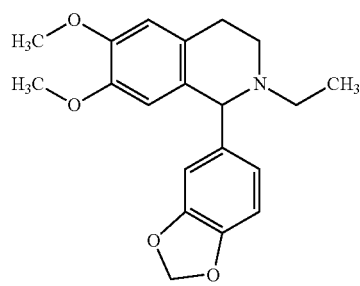

Structure XVII or salt thereof.

The salt may be a HCl salt.

The invention also provides any compound described herein including the compounds of the tables herein and the structures of FIGS. 19, 23, 28 and 29 and salts thereof and the use thereof as medicaments, particularly for treatment of an angiogenesis related disease or disorder as herein described and/or cancer such as colorectal cancer, oesophageal cancer or breast cancer.

The compounds and compositions of the invention may be administered by any conventional route for example parenterally such as in the form of an injectable solution or suspension, enterally for example orally such as in the form of an oral dosage form for example a tablet or a capsule, or topically for example in the form of lotions, gels, ointments, creams or eyedrops. The compounds or compositions of the invention may also be administered in a nasal or suppository form. The route of administration of the compounds and compositions of the invention will depend on the angiogenic driven disease (angiogenic-related disease or disorder) and/or the undesirable inflammation to be treated.

It will be appreciated by a person skilled in the art that the compounds and compositions of the invention should be administered in a therapeutically effective amount. The dosage of the active ingredient will depend on a variety of factors including type, species, age, weight, sex, medical condition of the patient, the severity of the condition to be treated and the route of administration.

BRIEF DESCRIPTION OF THE FIGURES

The invention will be more clearly understood from the following description of some embodiments thereof, given by way of example only, with reference to the accompanying figures, in which:

FIG. 15 tables the percentage inhibition by compounds 11B_CC11_HCl and 11B_CC16_HCl on the cysteinyl leukotriene pathway in in vitro and ex vivo assays. Ex vivo cysteinyl leukotriene lung strip assay: 11B_CC16_HCl was tested at 30 μM concentration in duplicate, in a single experiment for its ability to inhibit 3 nM leukotriene D4-induced contraction of a 3 mg strip of guinea pig lung. 30 μM 11B_CC16_HCl was sufficient to completely inhibit such contraction. For in vitro cysteinyl leukotriene cell-based assays 11B_CC11_HCl and 11B_CC16_HCl, were tested at 30 μM concentration in duplicate, in a single experiment for their ability to inhibit the calcium mobilisation response of the CysLT1 receptor to 0.1 nM leukotriene D4 in CHO cells over-expressing the CysLT1 receptor or the calcium mobilisation response of the CysLT2 receptor to 30 nM of leukotriene C4 in HEK 293 cells over expressing the CysLT2 receptor.

FIG. 18B shows representative epi-fluorescent images of the hyaloid vessels on dissected zebrafish lenses, depicting the patterns of hyaloid vasculature observed in zebrafish larvae treated with DMSO (control) and an 11B-series of compounds: control, 11B_CC2, 11B_CC2_HCl, 11B_CC4_HCl, 11B-CC5, 11B_CC5_HCl, 11B_CC16, 11B_CC16_HCl and control 11B-268, 11B-074, 11B-438 and 11B-739.

FIG. 29 A is a graph showing the effect of 5 μM of compound 11B_Z and 11B_Z_HCl in inhibiting developmental angiogenesis of the hyaloid vasculature in the zebrafish eye. FIG. 29 B is a graph showing the effect of 10 μM of compound 11B_Z and 11B_Z_HCl in inhibiting developmental angiogenesis of the intersegmental vessels. FIG. 29 C shows a representative image for 11B_Z hyaloid vasculature, intersegmental vessels and the chemical structure of 11B_Z. FIG. 29 D shows a representative image for 11B_Z_HCl hyaloid vasculature, intersegmental vessels and the chemical structure of 11B_Z_HCl. FIG. 29 E tables the percentage inhibition by compounds 11B_Z and 11B_Z_HCl of the cysteinyl leukotriene pathway. Details on these assays are given in the legend for FIG. 15.

DETAILED DESCRIPTION

TABLE 1

11B Series Compounds

Figure 1:
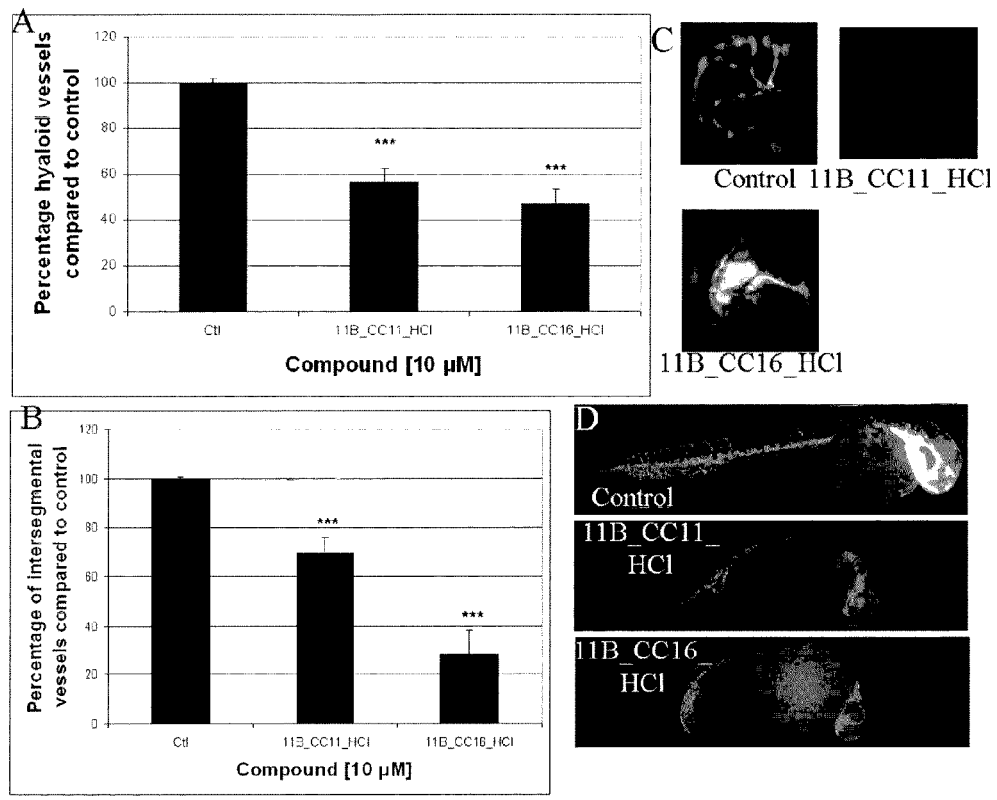
FIGS. 1 A, B, C and D show the effect of 10 μM of 11B_CC11_HCl and 11B_CC16_HCl compounds on inhibiting developmental angiogenesis of the hyaloid vasculature (A is a graph and C shows representative images) and intersegmental vasculature (B is a graph and D shows images) in zebrafish. n>=12, *** p-value ≤0.001. Data shown is mean+SEM.
Figure 2:
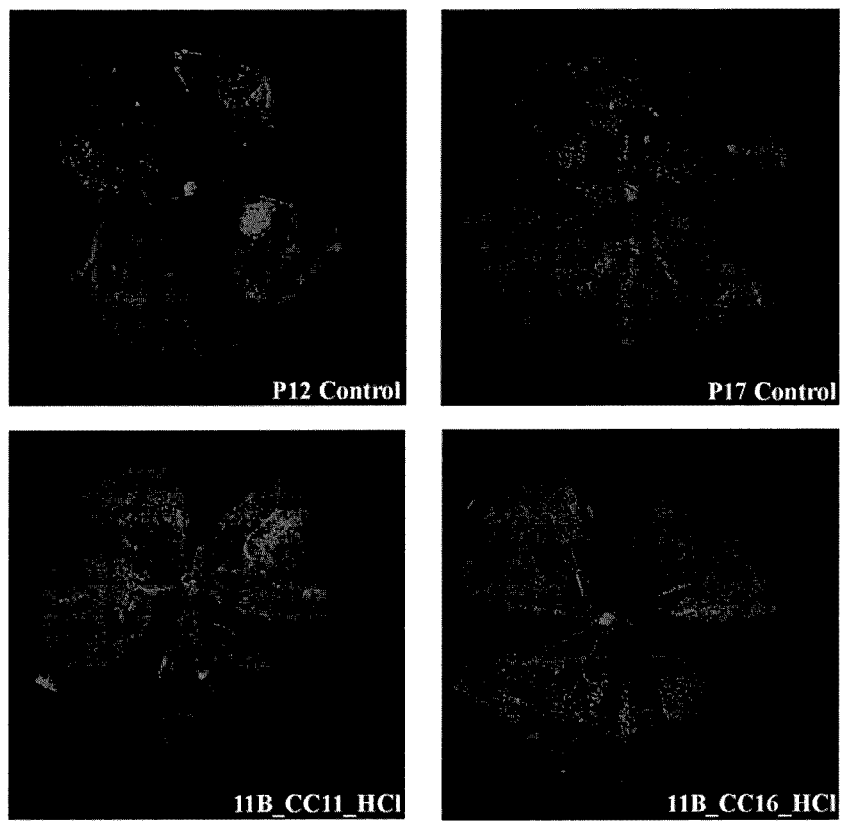
FIGS. 2 A and B are representative images and graphs showing the effect of 5 μM of 11B_CC11_HCl and 11B_CC16_HCl compounds on inhibiting neovascularisation in the mouse oxygen-induced retinopathy model. Data shown is mean+SEM. N=3 experiments and n=4 (P12 control and P17 control), n=5 (Avastin), n=8 (pazopanib), n=9 (11B_CC11_HCl) and n=15 (11B_CC16_HCl).
Figure 2:
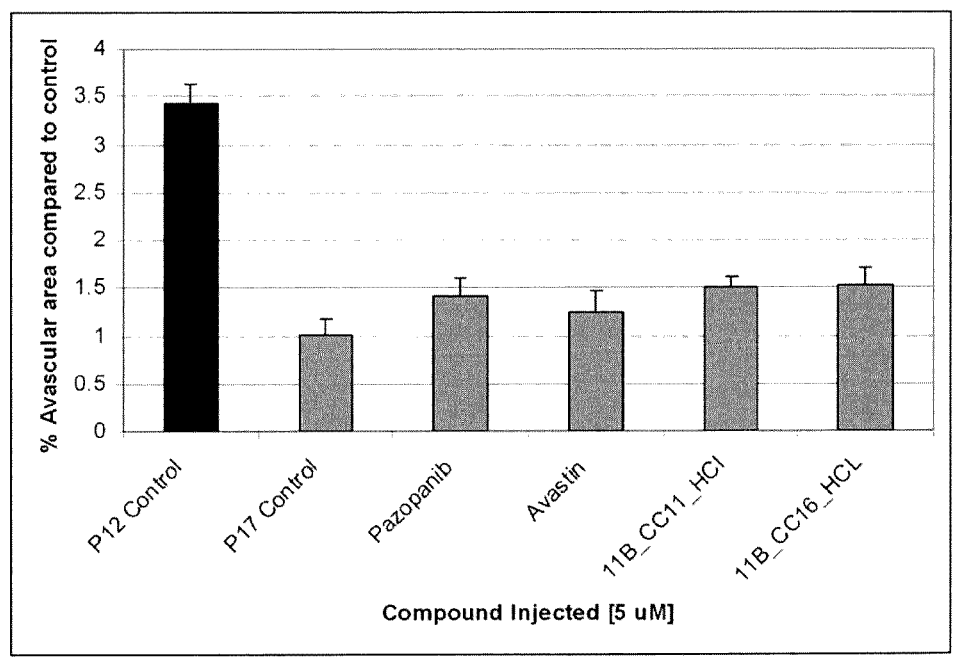
Figure 3:
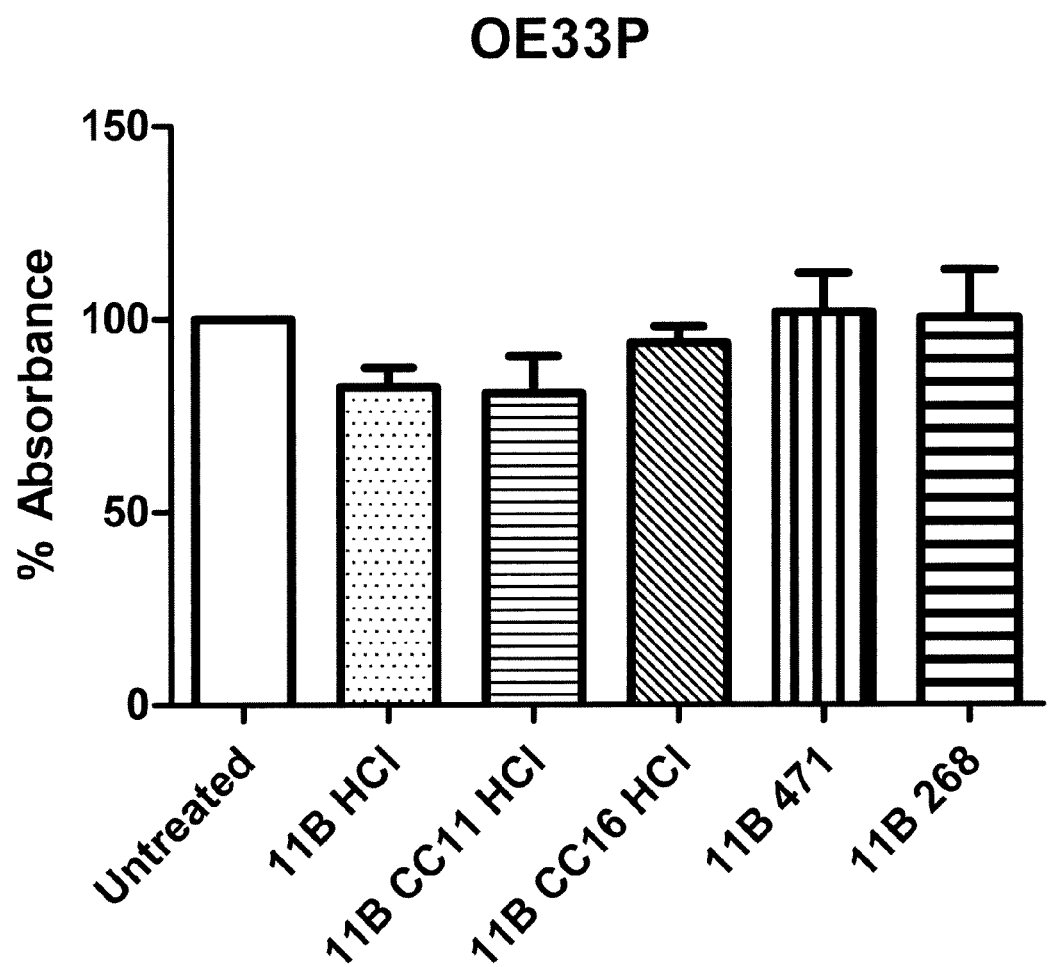
FIG. 3 is a graph showing that compounds 11B HCl, 11B_CC11_HCl, 11B_CC16_HCl, 11B 471 and 11B 268 did not significantly reduce cell number, measured by % absorbance, in OE33P radio-sensitive oesophageal adenocarcinoma cells. OE33P were treated with 10 μM of 11B HCl, 11B_CC11_HCl, 11B_CC16_HCl, 11B 471 or 11B 268 for 24 hours, fixed with glutaraldehyde, stained with crystal violet, resuspended with TritonX-100 and absorbance measured at 590 nm.
Figure 4:
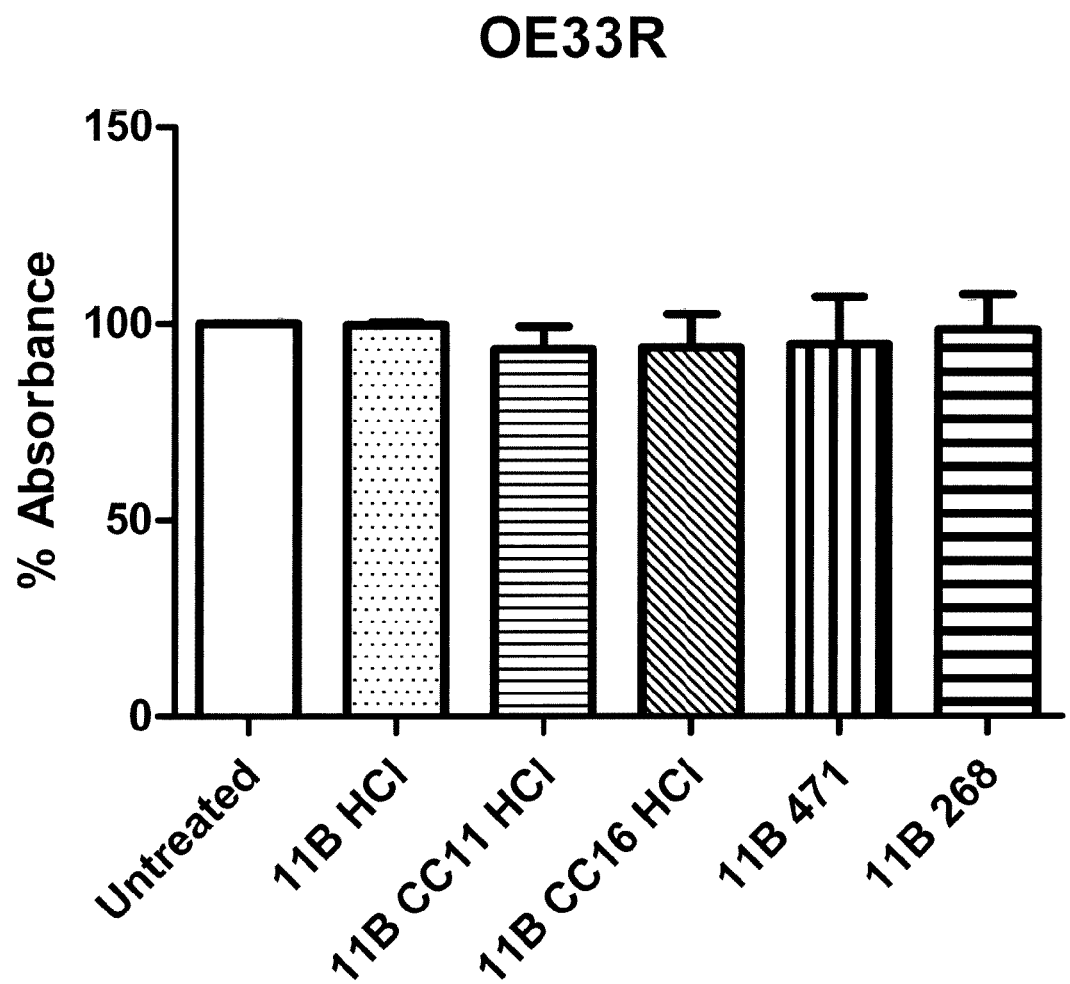
FIG. 4 is a graph showing that compounds 11B HCl, 11B_CC11_HCl, 11B_CC16_HCl, 11B 471 and 11B 268 did not significantly reduce cell number, measured by % absorbance, in OE33 radio-resistant oesophageal adenocarcinoma cells. OE33R were treated with 10 μM of 11B HCl, 11B+CC11_HCl, 11B_CC16_HCl, 11B 471 or 11B 268 for 24 hours, fixed with glutaraldehyde, stained with crystal violet, resuspended with TritonX-100 and absorbance measured at 590 nm.
Figure 5:
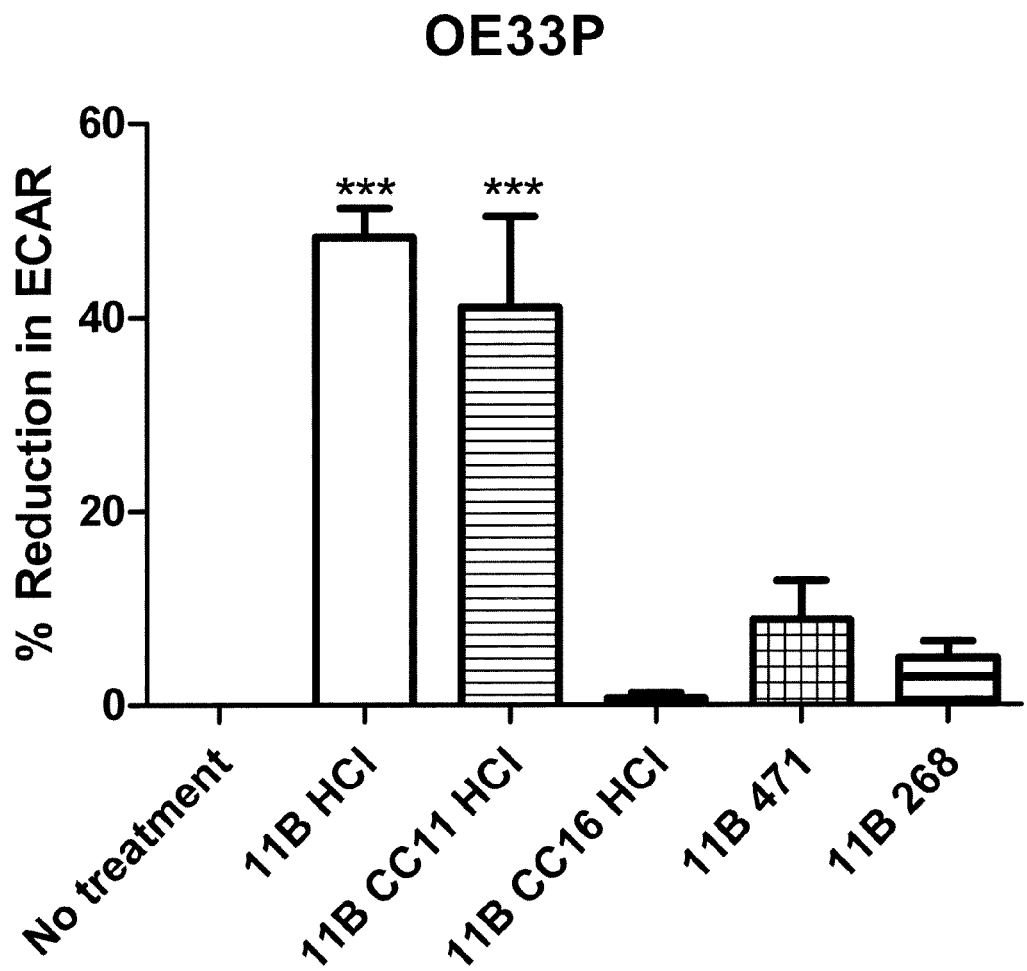
FIG. 5 is a graph showing that compounds 11B HCl and 11B_CC11_HCl significantly reduce extracellular acidification rate (ECAR), a measure of glycolysis, in OE33P radiosensitive oesophageal adenocarcinoma cells. OE33P were treated with 10 μM of 11B HCl, 11B_CC11_HCl, 11B_CC16_HCl, 11B 471 or 11B 268 for 24 hours, then ECAR was determined using Seahorse Bioscience metabolism technology.
Figure 6:
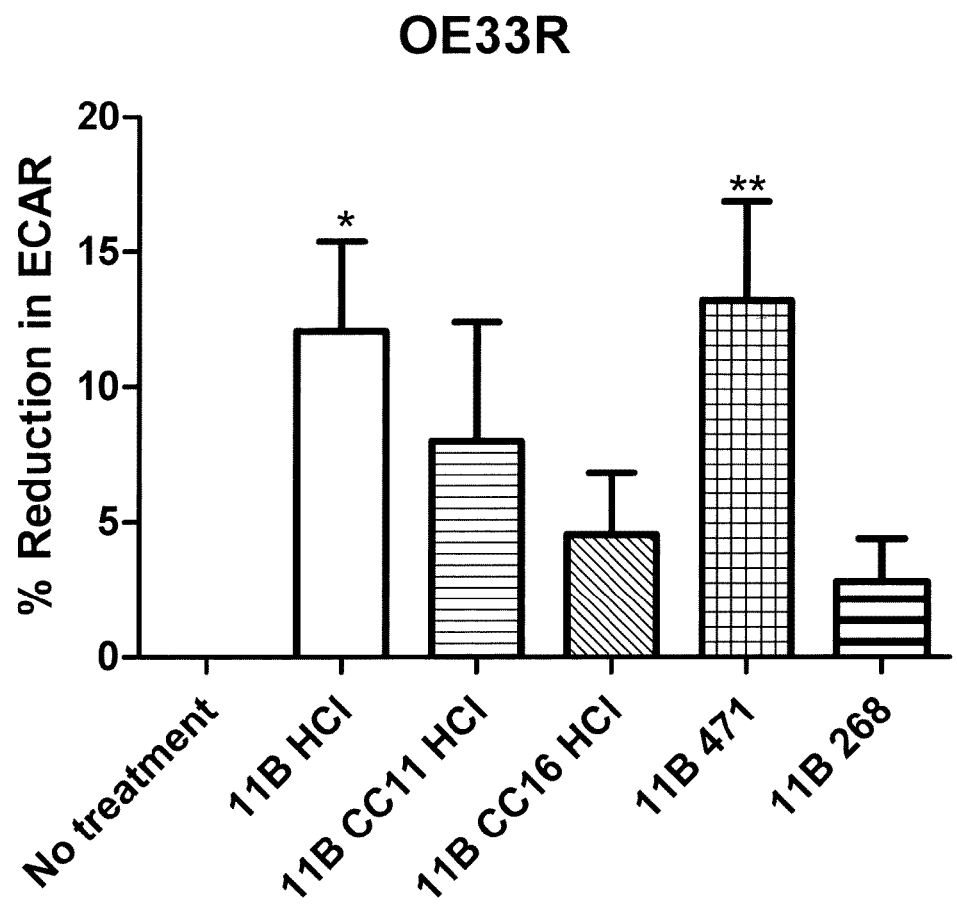
FIG. 6 is a graph showing that compounds 11B HCl and 11B 471 significantly reduce extracellular acidification rate (ECAR), a measure of glycolysis, in OE33R radio-resistant oesophageal adenocarcinoma cells. OE33R were treated with 10 μM of 11B HCl, 11B_CC11_HCl, 11B_CC16_HCl, 11B 471 or 11B 268 for 24 hours, then ECAR was determined using Seahorse Bioscience metabolism technology.
Figure 7:
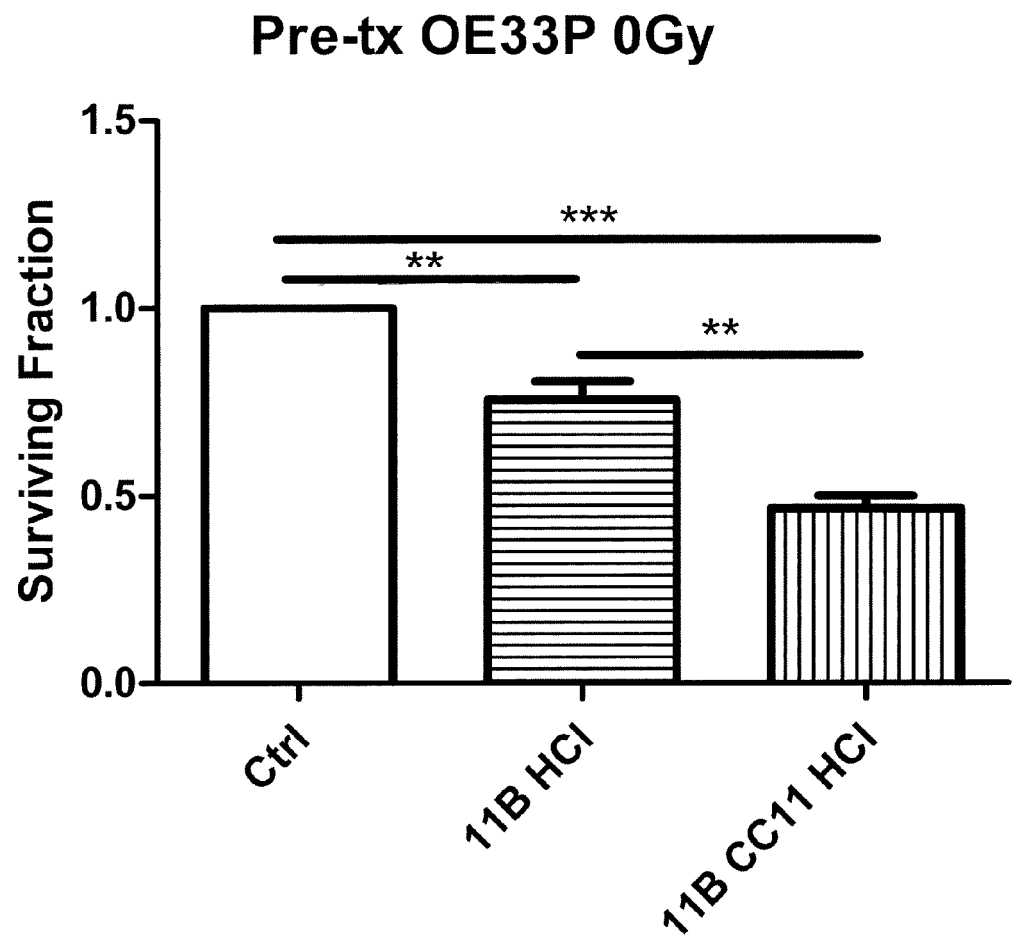
FIG. 7 is a graph showing that compounds 11B HCl and 11B_CC11_HCl significantly reduce the surviving fraction of OE33P radio-sensitive oesophageal adenocarcinoma cells. OE33P were treated with 10 μM of 11B HCl or 11B_CC11_HCl for 24 hours and left until control untreated colonies were sufficiently large enough to score.
Figure 8:
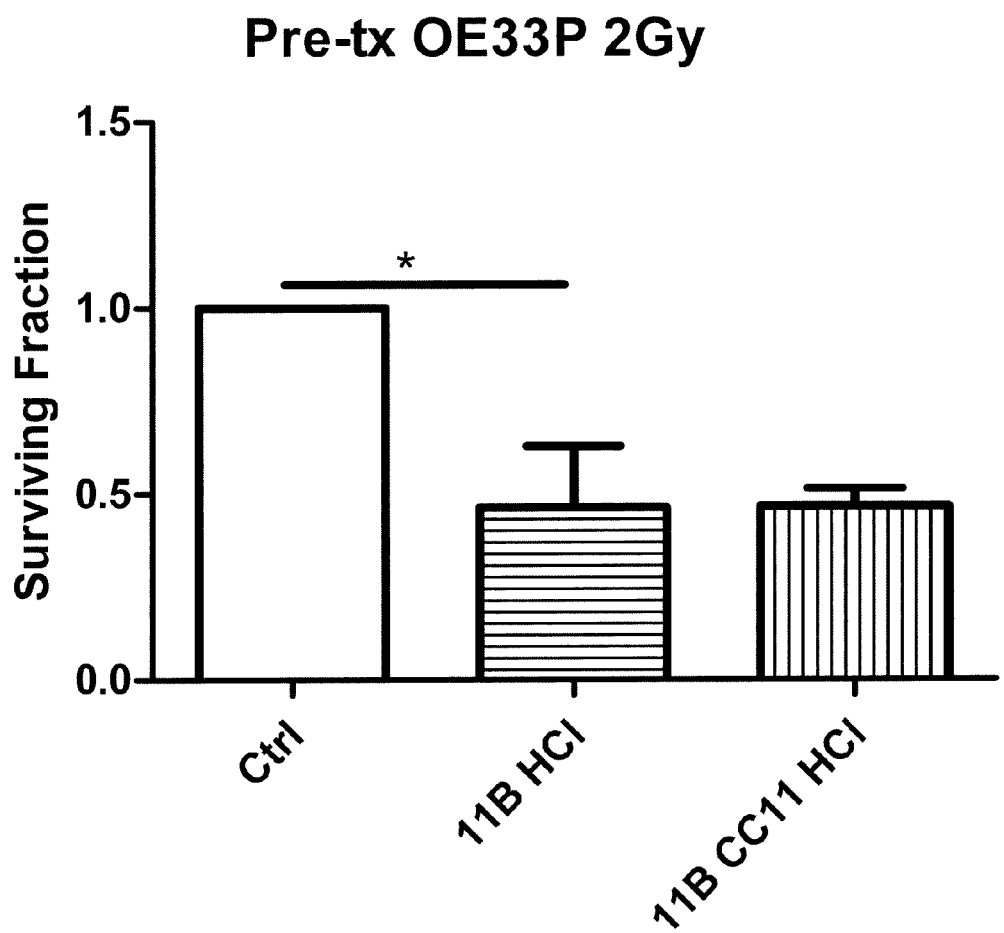
FIG. 8 is a graph showing that compound 11B HCl significantly reduces surviving fraction of OE33P radio-sensitive oesophageal adenocarcinoma cells when cells were treated prior to 2Gy irradiation. OE33P were treated with 10 μM of 11B HCl or 11B_CC11_HCl for 24 hours, irradiated and left until control untreated colonies were sufficiently large enough to score.
Figure 9:
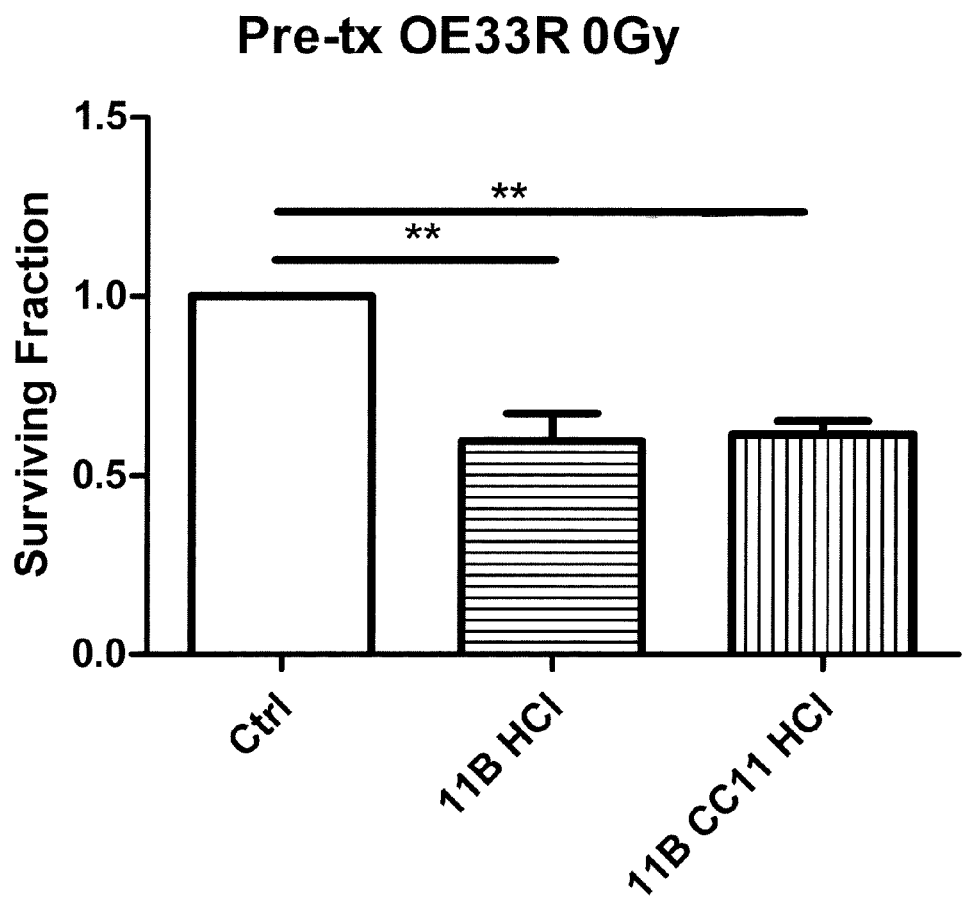
FIG. 9 is a graph showing that compounds 11B HCl and 11B_CC11_HCl significantly reduce surviving fraction of OE33R radio-resistant oesophageal adenocarcinoma cells. OE33R were treated with 10 μM of 11B HCl or 11B_CC11_HCl for 24 hours and left until control colonies were sufficiently large enough to score.
Figure 10:
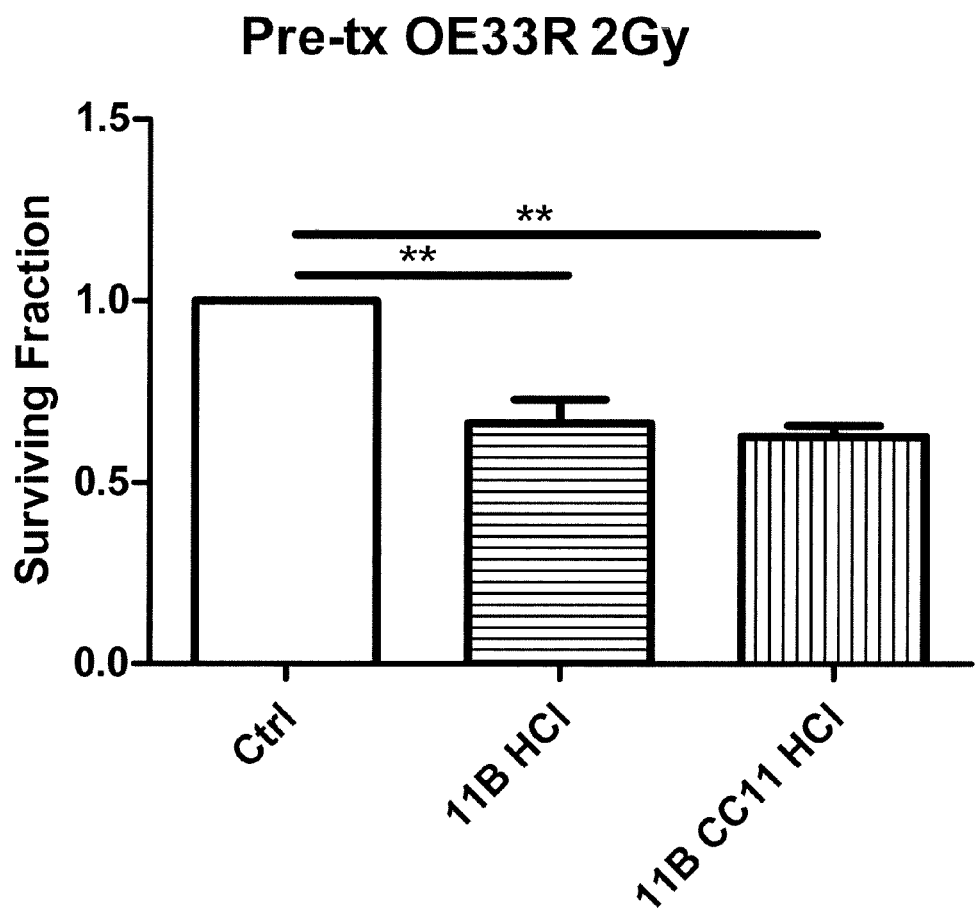
FIG. 10 is a graph showing that compounds 11B HCl and 11B_CC11_HCl significantly reduce the surviving fraction of OE33R radio-resistant oesophageal adenocarcinoma cells when cells were treated prior to 2Gy irradiation. OE33R were treated with 10 μM of 11B HCl or 11B_CC11_HCl for 24 hours, irradiated and left until control colonies were sufficiently large enough to score.
Figure 11:
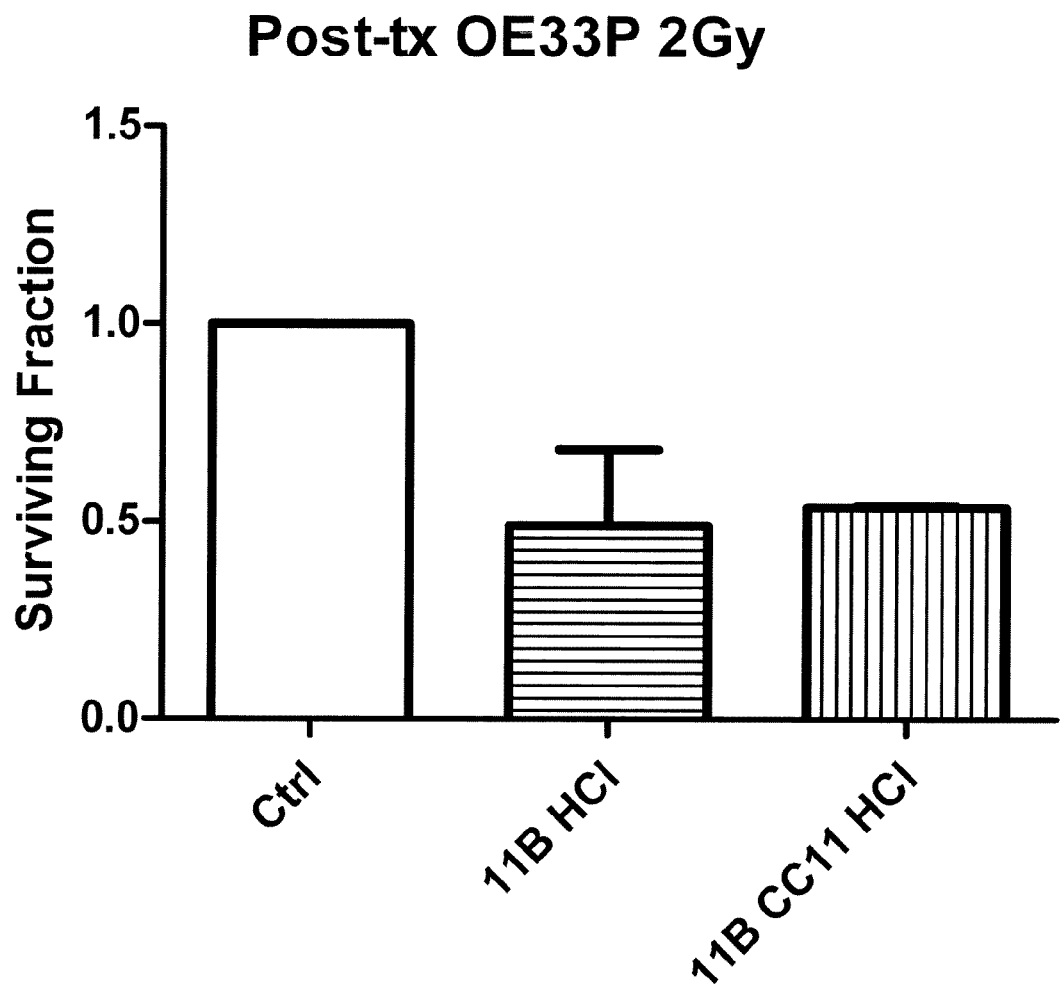
FIG. 11 is a graph showing the surviving fraction of OE33P radiosensitive oesophageal adenocarcinoma cells when cells were treated with 11B HCl and 11B_CC11_HCl following 2Gy irradiation. OE33P were irradiated, treated with 10 μM of 11B HCl or 11B_CC11_HCl for 24 hours and left until control colonies were sufficiently large enough to score.
Figure 12:
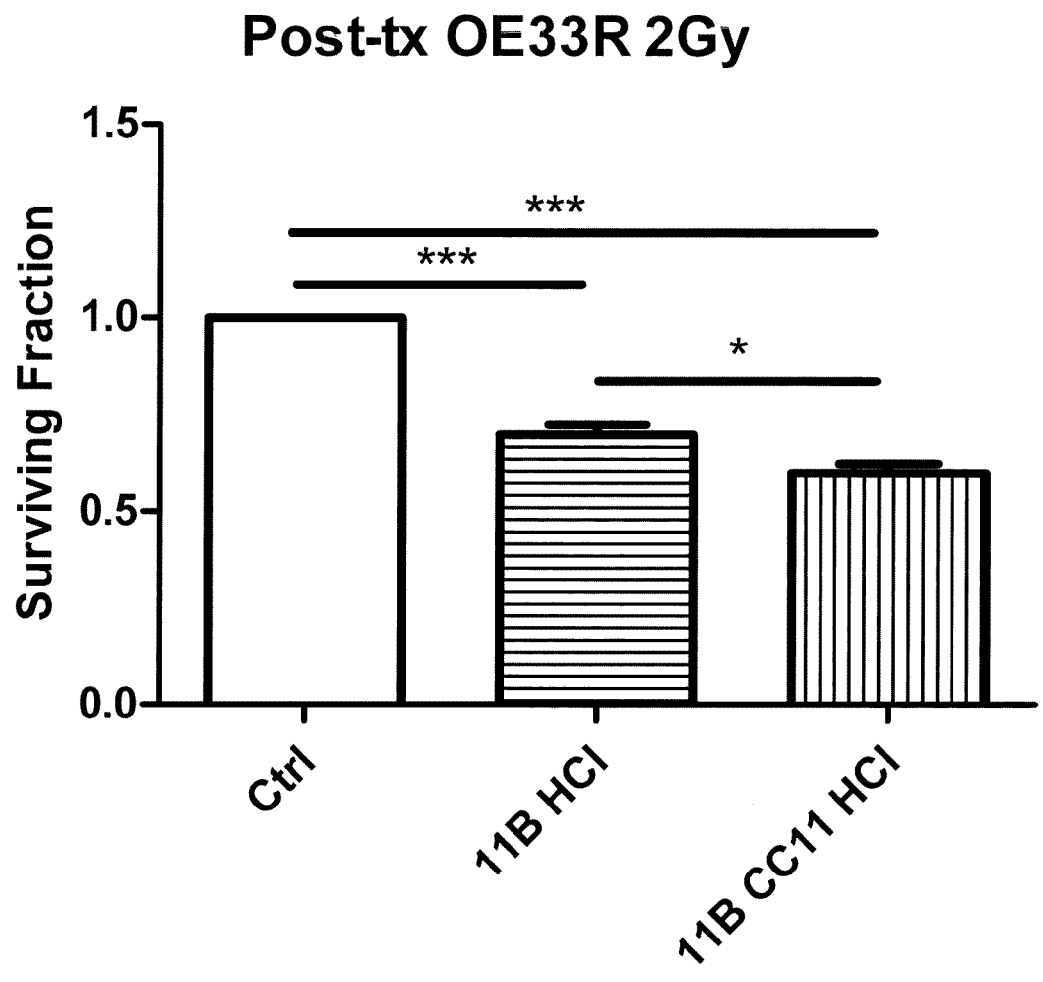
FIG. 12 is a graph showing that compounds 11B HCl and 11B_CC11_HCl significantly reduce the surviving fraction of OE33R radio-resistant oesophageal adenocarcinoma cells when cells were treated following 2Gy irradiation. OE33R were irradiated, treated with 10 μM of 11B HCl or 11B_CC11_HCl for 24 hours and left until control colonies sufficiently large enough to score.
Figure 13:
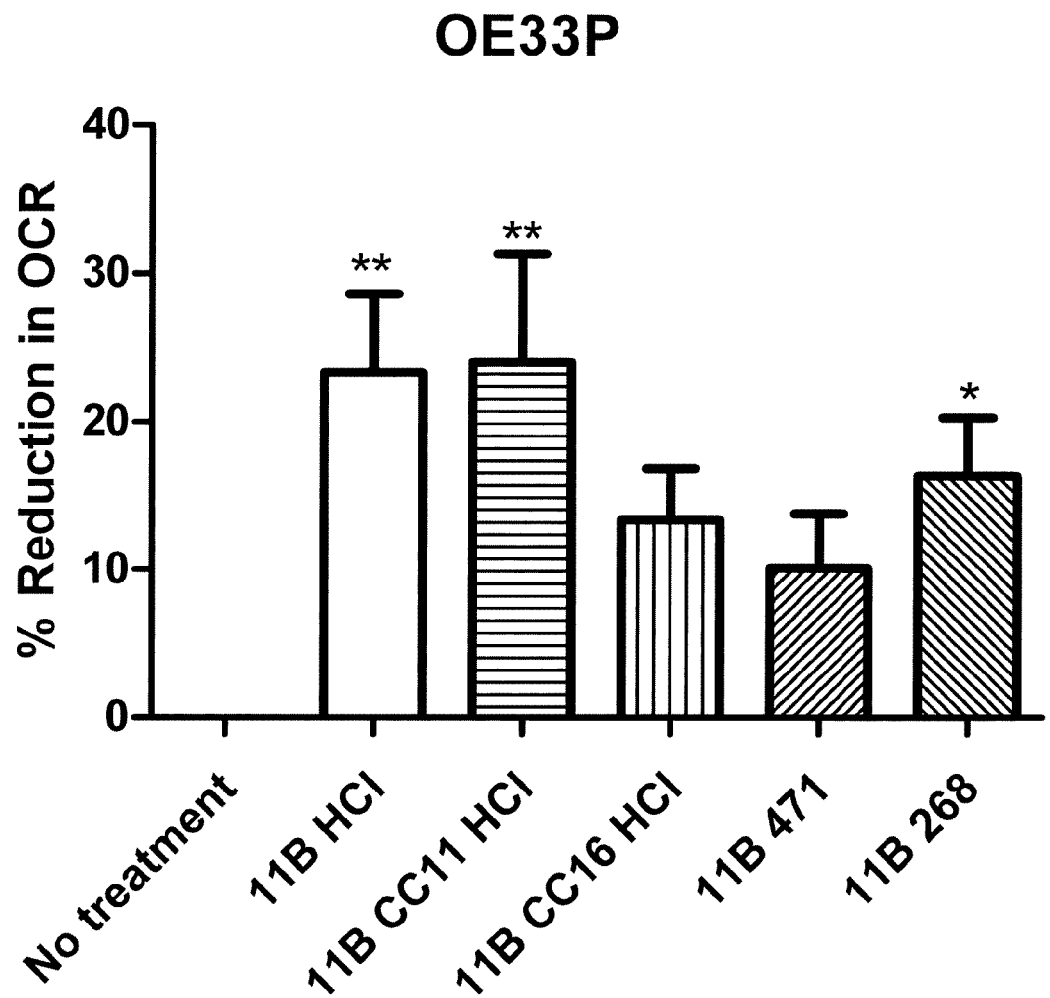
FIG. 13 is a graph showing that compounds 11B HCl, 11B_CC11_HCl and 11B 268 significantly reduce oxygen consumption rate (OCR), a measure of oxidative phosphorylation, in OE33P radiosensitive oesophageal adenocarcinoma cells. OE33P were treated with 10 μM of 11B HCl, 11B_CC11_HCl, 11B_CC16_HCl, 11B 471 or 11B 268 for 24 hours, then OCR measured using Seahorse Bioscience metabolism technology.
Figure 14:
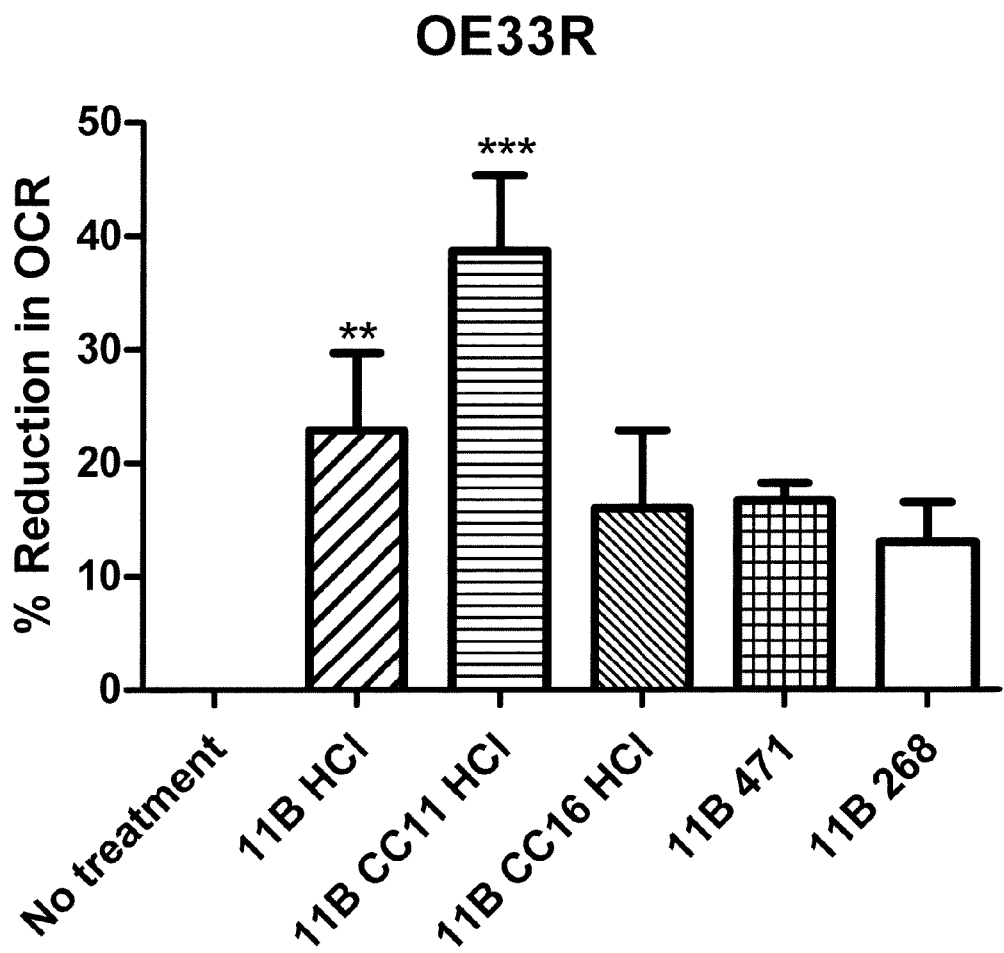
FIG. 14 is a graph showing that compounds 11B HCl and 11B_CC11_HCl significantly reduce oxygen consumption rate (OCR), a measure of oxidative phosphorylation, in OE33R radio-resistant oesophageal adenocarcinoma cells. OE33R were treated with 10 μM of 11B HCl, 11B_CC11_HCl, 11B_CC16_HCl, 11B 471 or 11B 268 for 24 hours, then OCR measured using Seahorse Bioscience metabolism technology.
Figure 16:
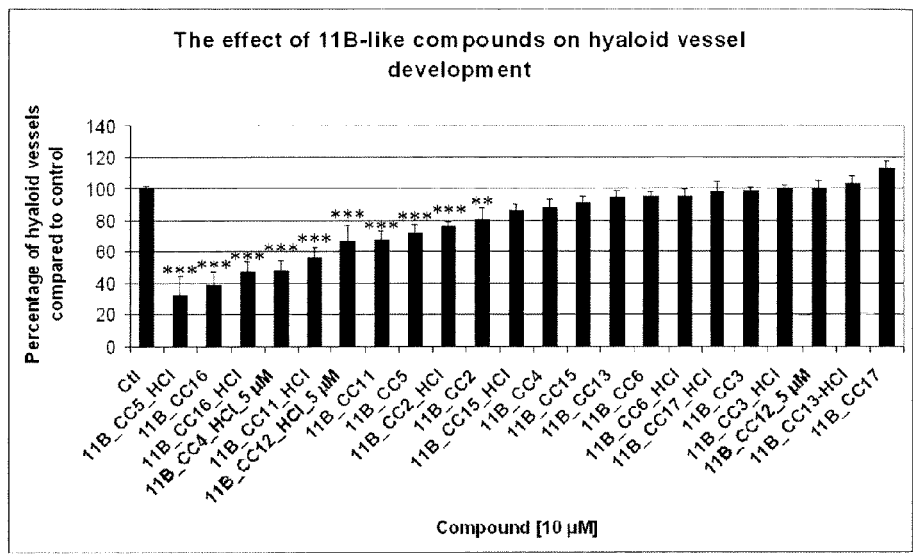
FIGS. 16 A and B are graphs showing the effect of 10 μM or 5 μM of an 11B-series of compounds on inhibiting developmental angiogenesis of the hyaloid vasculature in the zebrafish eye. n≥10 for all samples except 11B_CC5_HCl where n=5.* p-value ≤0.05,  p-value ≤0.01, * p-value ≤0.001.
Figure 16:
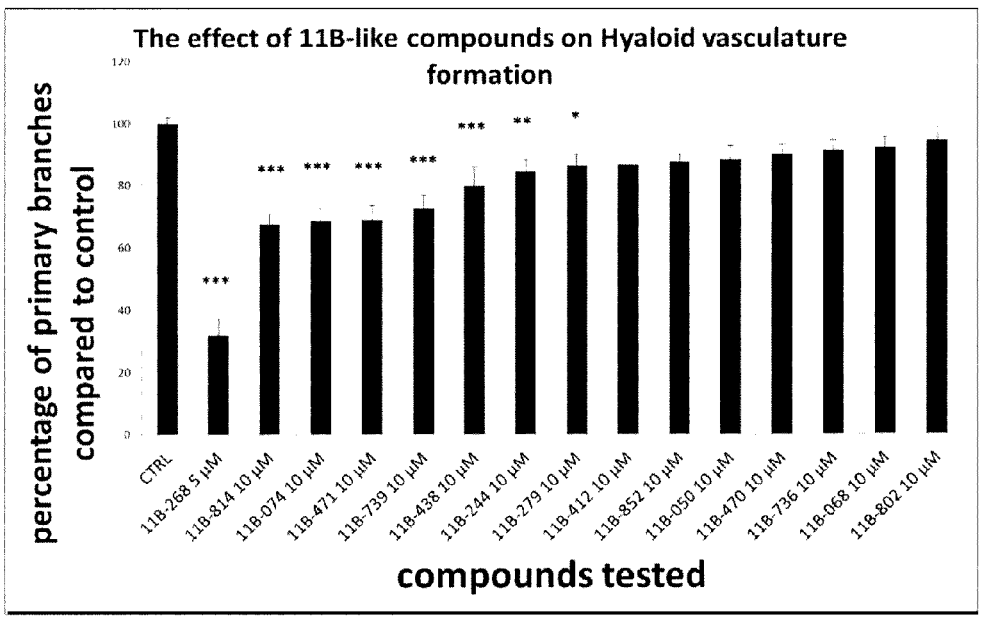
Figure 17:
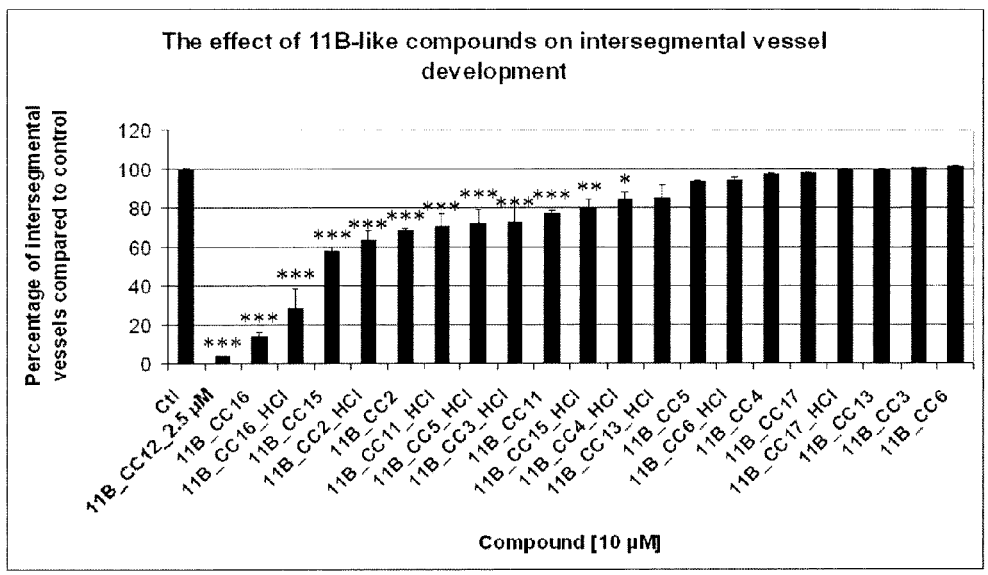
FIGS. 17 A and B are graphs showing the effect of 10 μM of 11B-series of compounds on inhibiting developmental angiogenesis of the intersegmental vasculature in zebrafish (exception is 11B_CC12 tested at 2.5 μM) n≥12 for all samples except 11B_CC12 where n=2. * p-value ≤0.05, ** p-value ≤0.01, * * * p-value ≤0.001.
Figure 17:
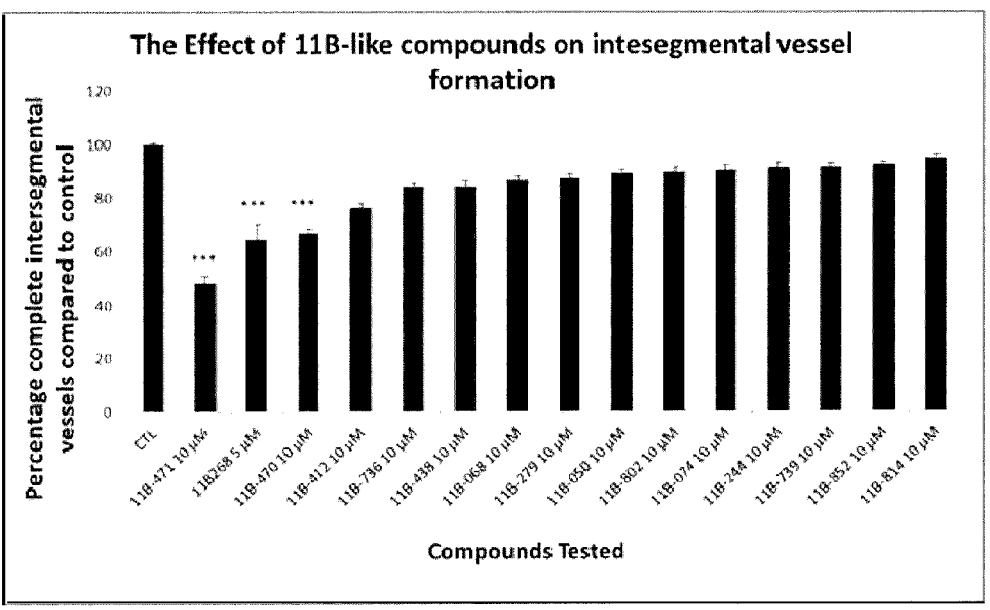
Figure 18:
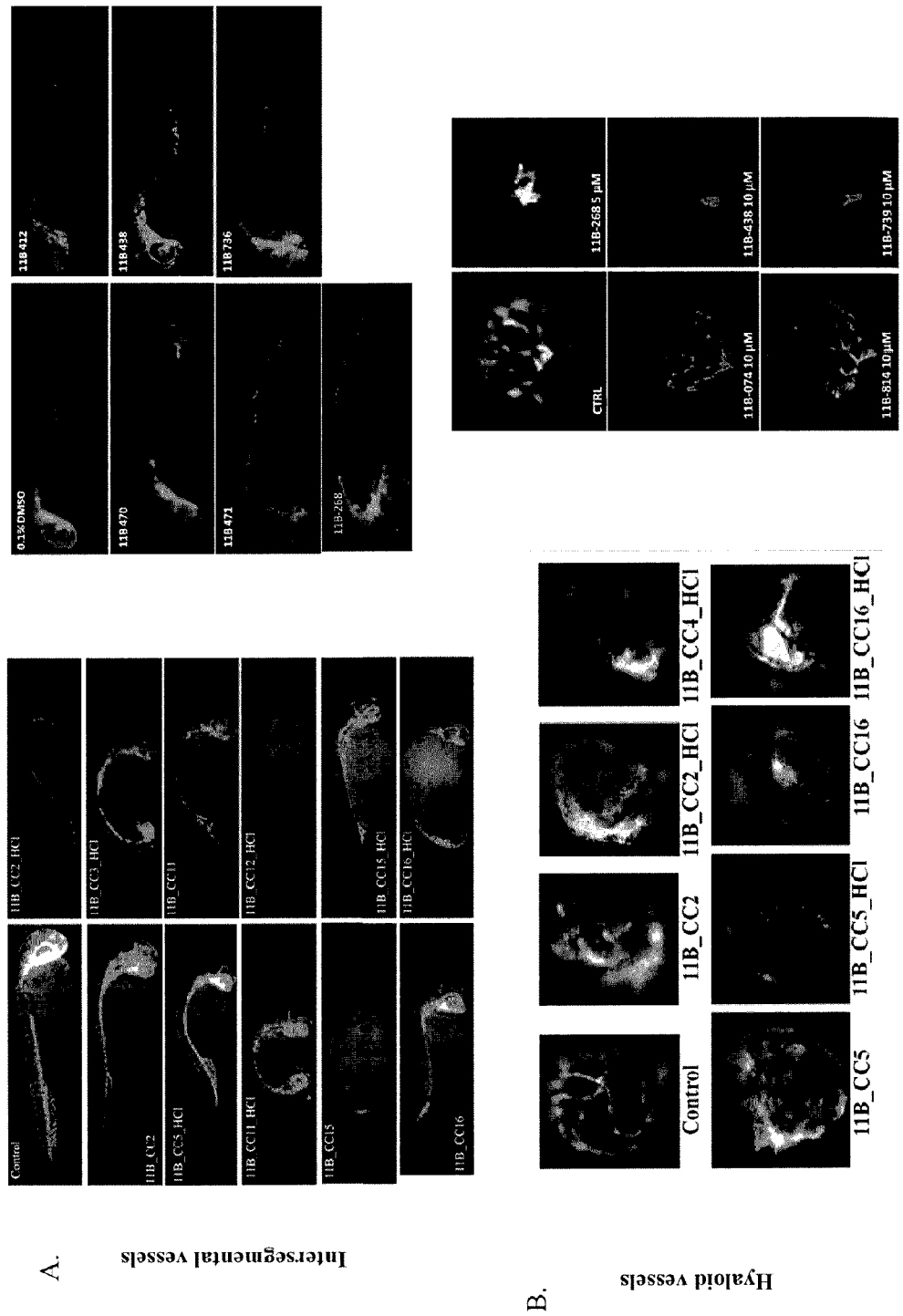
FIGS. 18 A and B are representative epi-fluorescent images of the intersegmental vessels observed in zebrafish larvae treated with 10 μM of an 11B-series of compounds: Control, 11B_CC2, 11B_CC2_HCl, 11B_CC3_HCl, 11B_CC5_HCl, 11B_CC11, 11B_CC11_HCl, 11B_CC12 HCl, 11B_CC15, 11B_CC15_HCl, 11B_CC16 and 11B_CC16_HCl and DMSO (control), 11B-412, 11B-470, 11B-438, 11B-471, 11B-736 and 11B-268.

| Structure | Code name | Chemical name |
|---|---|---|
|  | 11B-068 | 2-[(E)-2-(2-Hydroxyphenyl)vinyl]-4-quinolinol |
|  | 11B-244 | 2-[2-(4-ethoxyphenyl)vinyl]quinoline |
|  | 11B-050 | 2-[2-(2-aminophenyl)vinyl]-8-quinolinol |
| Structure XII | 11B-736 | 2-[2-(2-chlorophenyl)vinyl]-8-quinolinol |
| Structure XIII | 11B-739 | 2-[2-(2-ethoxyphenyl)vinyl]-8-quinolinol |
| Structure X | 11B-470 | 2-[(E)-2-(2-Hydroxyphenyl)vinyl]-4-quinolinol |
|  | 11B-852 | 2-[2-(2-methylphenyl)vinyl]-8-quinolinol |
| Structure IX | 11B-438 | 2-[(E)-2-(2-Hydroxy-3-methylphenyl)vinyl]-8-quinolinol |
| Structure VII | 11B-074 | 2-[2-(5-bromo-2-methoxyphenyl)vinyl]quinoline |
|  | 11B-802 | 2-[2-(2-bromo-5-ethoxyphenyl)vinyl]quinoline |
| Structure XI | 11B-471 | 2-[2-(3-pyridinyl)vinyl]quinoline |
| Structure VIII | 11B-412 | 2-[2-(5-iodo-2-methoxyphenyl)vinyl]quinoline |
|  | 11B-279 | 2-[2-(2-methoxyphenyl)vinyl]-8-quinolinol |
| Structure I | 11B-CC2 | 3-(2-Quinolin-2-yl-vinyl)-phenol |
|  | 11B-CC2-HCl | 3-(2-Quinolin-2-yl-vinyl)-phenol HCl salt |
|  | 11B-CC3 | 4-(2-Quinolin-2-yl-vinyl)-phenol |
|  | 11B-CC3-HCl | 4-(2-Quinolin-2-yl-vinyl)-phenol HCl salt |
| Structure II | 11B-CC4 | 2-(2-Quinolin-2-yl-ethyl)-phenol |
|  | 11B-CC4-HCl | 2-(2-Quinolin-2-yl-ethyl)-phenol HCl salt |
| Structure III | 11B-CC5 | 3-(2-Quinolin-2-yl-ethyl)-phenol |
|  | 11B-CC5-HCl | 3-(2-Quinolin-2-yl-ethyl)-phenol HCl salt |
|  | 11B-CC6 | 4-(2-Quinolin-2-yl-ethyl)-phenol |
|  | 11B-CC6-HCl | 4-(2-Quinolin-2-yl-ethyl)-phenol HCl salt |
| Structure IV | 11B-CC11 | (E)-2-(2-Quinolin-2-yl-propenyl)-phenol |
|  | 11B-CC11-HCl | (E)-2-(2-Quinolin-2-yl-propenyl)-phenol HCl salt |
|  | 11B-CC12 | (E)-2-(2-Quinolin-2-yl-vinyl)- -benzene-1,4-diol |
|  | 11B-CC12-HCl | (E)-2-(2-Quinolin-2-yl-vinyl)- -benzene-1,4-diol HCl salt |
|  | 11B-CC13 | (E)-2-(2-Quinolin-2-yl-vinyl)- -benzene-2,4-diol |
|  | 11B-CC13-HCl | (E)-2-(2-Quinolin-2-yl-vinyl)-benzene-2,4-diolHCl salt |
| Structure V | 11B-CC15 | 3-Quinolin-2-yl-ylethynyl-phenol |
|  | 11B-CC15-HCl | 3-Quinolin-2-yl-ylethynyl-phenol HCl salt |
| Structure VI | 11B-CC16 | 2-Quinolin-2-yl-ylethynyl-phenol |
|  | 11B-CC16-HCl | 2-Quinolin-2-yl-ylethynyl-phenol HCl salt |
|  | 11B-268 | 2-(2-(2-Methoxyphenyl)vinyl)quinoline |
|  | 11B-814 | 3-[(E)-2-(6-Methyl-2-quinolinyl)vinyl]phenol |
|  | 11B_Z | (Z)-2-(2-(Quino lin-2-yl)vinyl) phenol |
|  | 11B_Z_HCl | (Z)-2-(2-(Quinolin-2-yl)vinyl) phenol HCl salt |

Synthesis of Analogues of 11B

The regioisomers of 11B, with the —OH functionality in different locations, were prepared by condensing 2-methylquinoline with the corresponding hydroxybenzaldehyde in acetic anhydride as solvent followed by basic hydrolysis of the resulting acetates (Scheme 1).

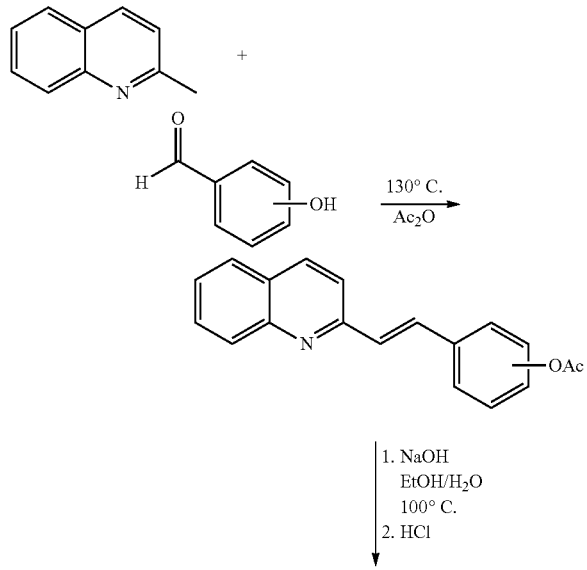

All analogues of 11B were made as both the free base and its HCl salt.

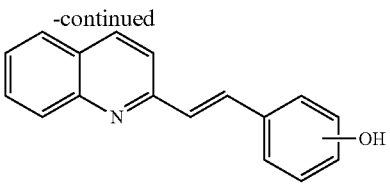

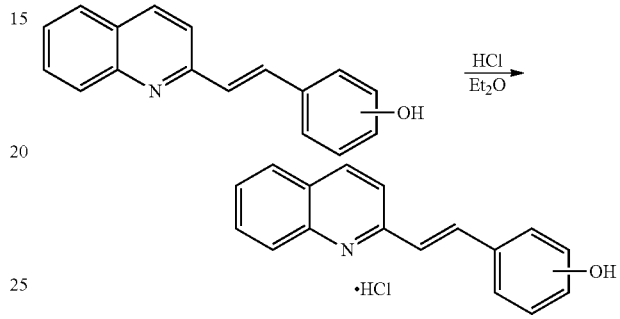

The single bond analogues were prepared by hydrogenating the acetylated alkene compounds over a catalytical amount of palladium metal on carbon under an atmosphere of hydrogen. After hydrolysis to remove the acetate the desire products were formed in high yields (Scheme 3).

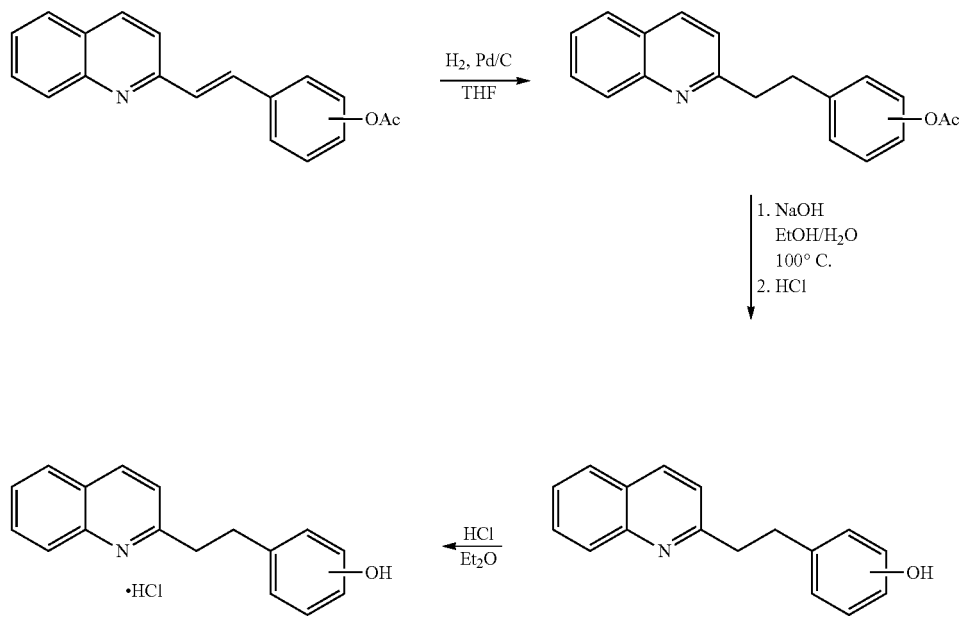

Bromination of the acetylated alkene, followed by base induced elimination yielded the acetyl protected alkynes (Scheme 4). The alkynes are then converted into HCl salts.

Quinoline analogues of 11B are made by a cis-selective hydrogenation of the corresponding acetylated alkyne, using the Lindlar catalyst, followed by hydrolysis. The compound

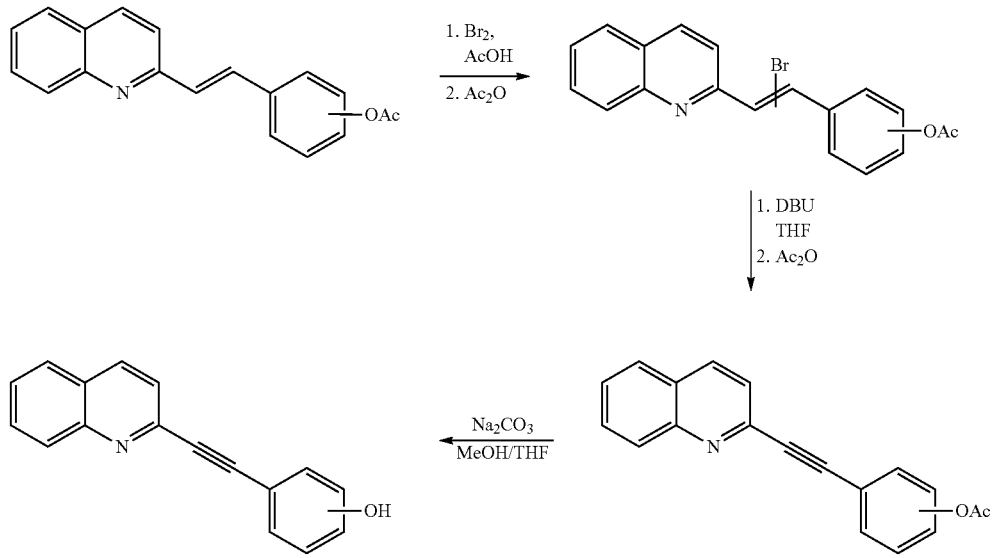

The 2,5-, 3,5-, 2,4-, and 3,4-dihydroxy analogues were prepare from condensation of the appropriate dihydroxy benzaldehyde compound with 2-methylquinoline followed by hydrolysis (Scheme 5).

with a methyl group on the double bond has been synthesised by converting 2-methylquinoline into 2-ethylquinoline followed by condensation with salicylic aldehyde and hydrolysis (Scheme 6).

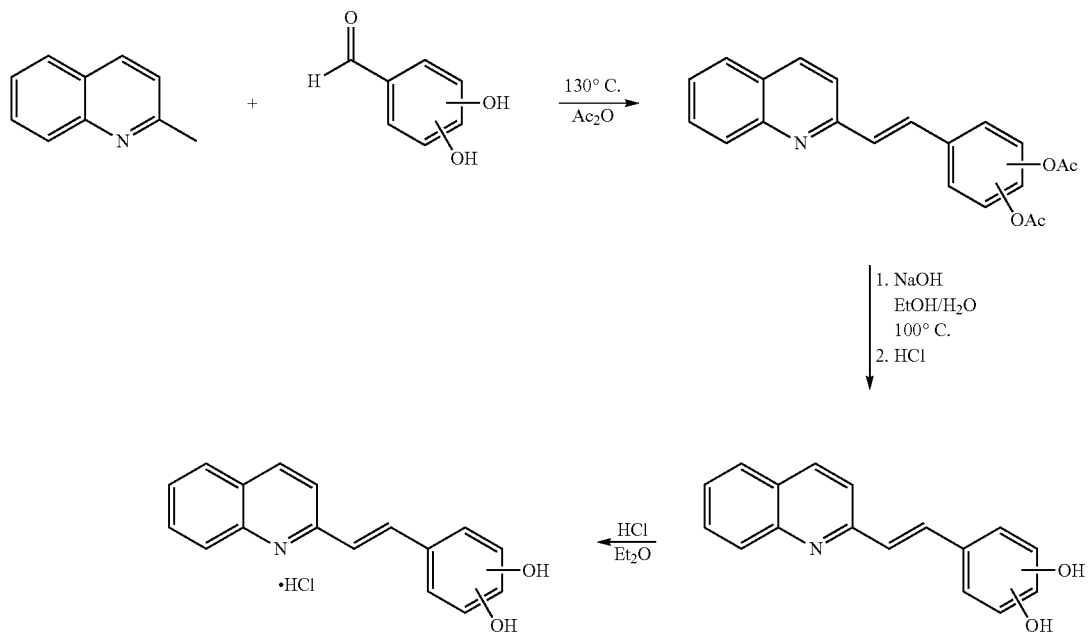

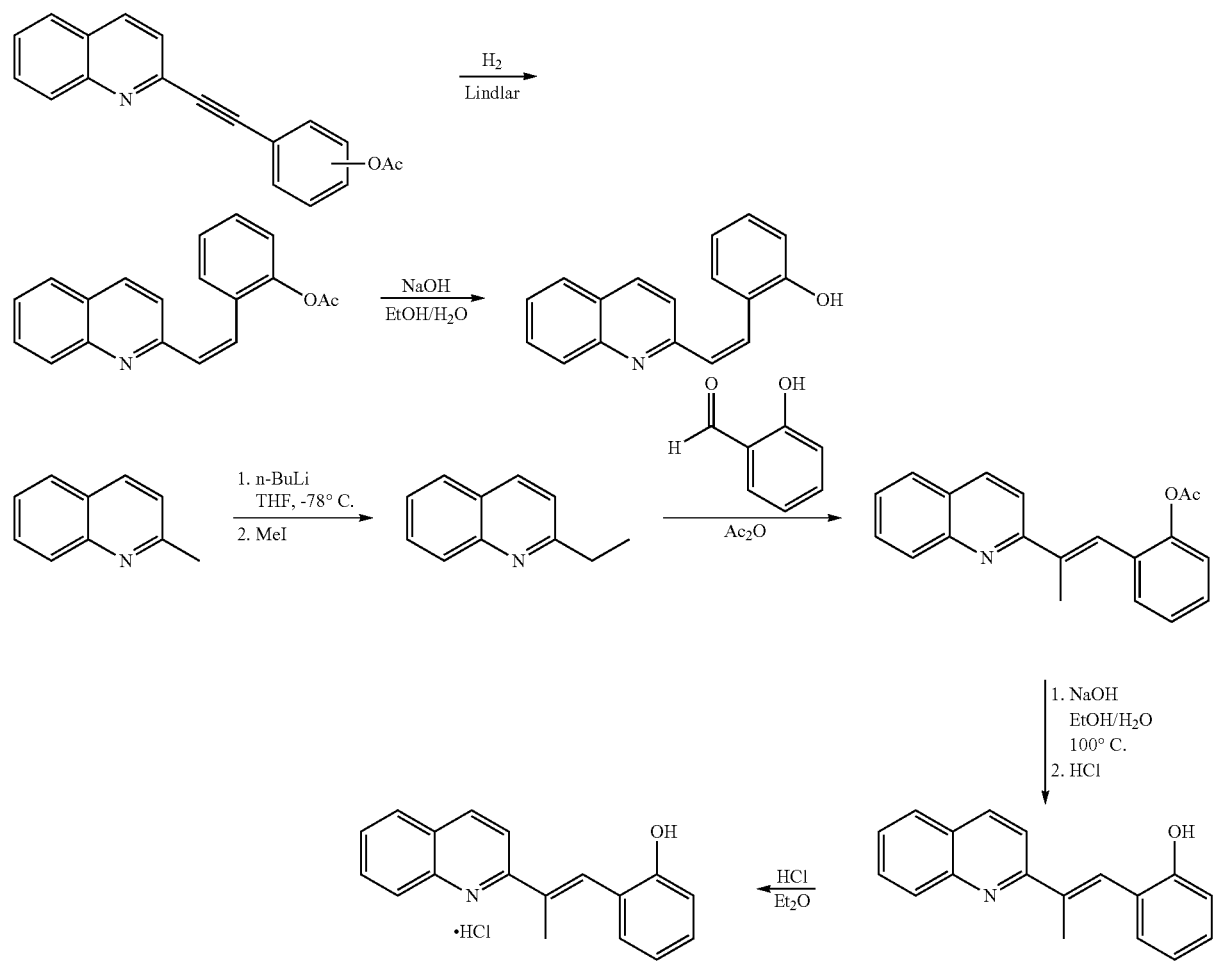
Synthesis of Compound CC11
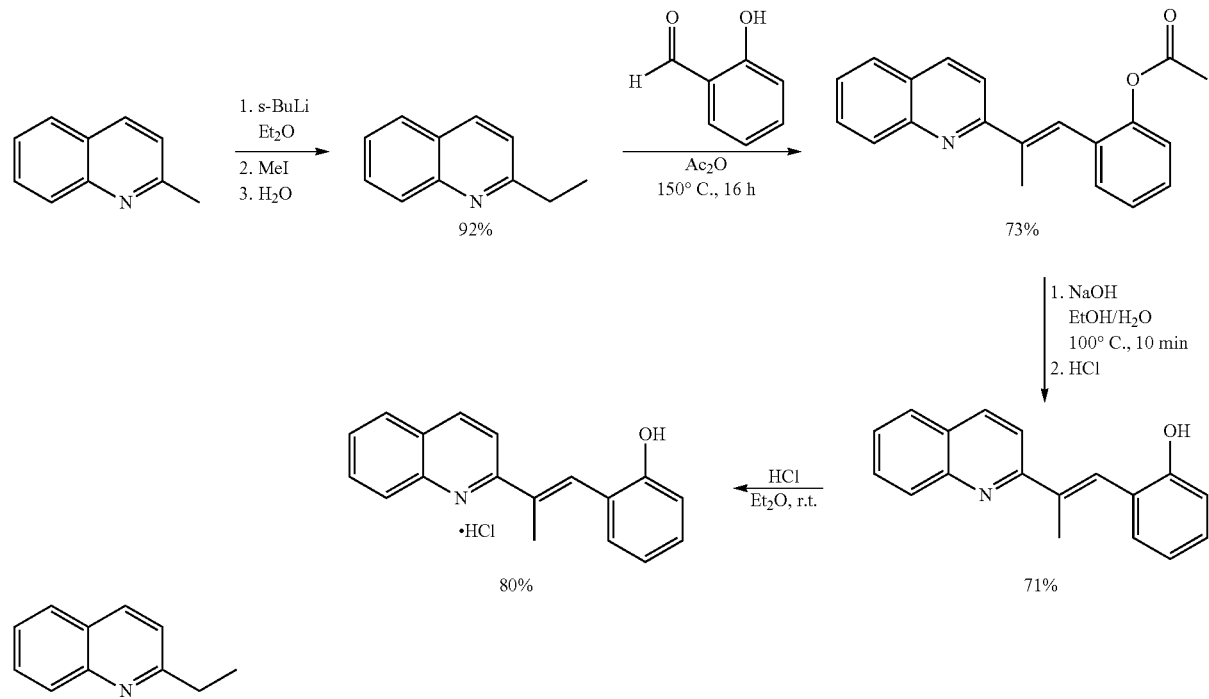

2-Ethylquinoline sec-Butyllithium (1.3 M in cyclohexane, 19.3 mL, 25.1 mmol, 1.2 eq.) was added dropwise to a 0° C. solution of 2-methylquinoline (2.84 mL, 3.0 g, 21.0 mmol, 1.0 eq.) in dry diethyl ether (75 mL). After the addition was complete the cooling bath was removed and the mixture was stirred at r.t. for 1.5 h. The reaction mixture was cooled to 0° C. and methyl iodide (1.96 mL, 4.46 g, 31.4 mmol, 1.5 eq.) was added dropwise. After the addition was complete the cooling bath was removed and the reaction was stirred at r.t. for 3 h. Water (50 mL) was added and the layers were separated. The aqueous layer was extracted with ethyl acetate (2×30 mL). The combined organic extracts were washed with brine (50 mL) and were dried over sodium sulfate and concentrated under reduced pressure which gave the crude product (4.82 g) as an orange oil. The crude product was purified by column chromatography (SiO$_2$, 1:5 ethyl acetate-cyclohexane) which yielded the product (3.03 g, 92% yield) as a clear yellow oil; $^1$H NMR (500 MHz, CDCl$_3$) δ 1.41 (t, J=7.5 Hz, 3H, CH$_3$), 3.01 (q, J=7.5 Hz, 2H, CH$_2$), 7.31 (d, J=8.5 Hz, 1H, Ar), 7.48 (t, J=7.5 Hz, 1H, Ar), 7.68 (t, J=7.5 Hz, 1H, Ar), 7.77 (d, J=8.0 Hz, 1H, Ar), 8.04 (d, J=8.5 Hz, 1H, Ar), 8.07 (d, J=8.5 Hz, 1H, Ar).

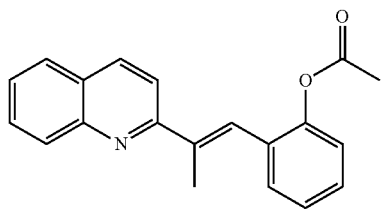 [SMILES: CC(=O)Oc1ccccc1/C=C(\C)c1ccc2ccccc2n1]

(E)-2-(2-(Quinolin-2-yl)prop-1-enyl)phenyl Acetate

2-Ethylquinoline (1.57 g, 10.0 mmol, 1.0 eq.) and 2-hydroxybenzaldehyde (1.06 mL, 1.22 g, 10.0 mmol, 1.0 eq.) were dissolved in acetic anhydride (1.89 mL, 2.04 g, 20.0 mmol, 2.0 eq.). The resulting mixture was heated at 150° C. for 16 h. The mixture was allowed to cool down to r.t. and was poured onto water (100 mL) and was stirred vigorously. The mixture was extracted with ethyl acetate (3×30 mL). The combined organic extracts were washed with brine (25 mL), dried over sodium sulfate and concentrated under reduced pressure which gave the crude product (3.63 g) as a clear orange oil. The crude product was purified by column chromatography (SiO$_2$, 1:5 ethyl acetate-cyclohexane) twice, which yielded the product (2.22 g, 73% yield) as a clear colourless oil.

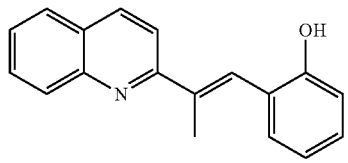 [SMILES: C/C(=C\c1ccccc1O)c1ccc2ccccc2n1]

(E)-2-(2-(Quinolin-2-yl)prop-1-enyl)phenol

Aqueous sodium hydroxide (5%, 8.8 g), followed by water (88 mL) were added to a stirred solution of (E)-2-(2-(quinolin-2-yl)prop-1-enyl)phenyl acetate (2.2 g, 7.3 mmol, 1.0 eq.) in ethanol (110 mL). The resulting mixture was heated at 100° C. for 10 min. The mixture was allowed to cool down a little and the pH was adjusted to 7.0 by careful addition of aqueous hydrochloric acid (10%). The mixture was allowed to cool down to r.t. and was then placed in a freezer (−18° C.) over night. The precipitation formed was isolated by filtration yielding the product (1.35 g, 71%) as a tan solid; $^1$H NMR (400 MHz, DMSO-d$_6$) δ 2.38 (s, 3H, CH$_3$), 6.87 (t, J=7.5 Hz, 1H, Ar), 6.92 (d, J=7.5 Hz, 1H, Ar), 7.16 (t, J=7.5 Hz, 1H, Ar), 7.36 (d, J=7.0 Hz, 1H, Ar), 7.56 (t, J=7.0 Hz, 1H, Ar), 7.61 (s, 1H, C=CH), 7.74 (t, J=7.0 Hz, 1H, Ar), 7.95 (d, J=8.5 Hz, 2H, Ar), 8.00 (d, J=8.5 Hz, 1H, Ar), 8.34 (d, J=8.5 Hz, 1H, Ar), 9.66 (br s, 1H, OH).

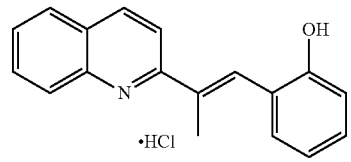 [SMILES: C/C(=C\c1ccccc1O)c1ccc2ccccc2n1 ; Cl]

(E)-2-(2-(Quinolin-2-yl)prop-1-enyl)phenol Hydrochloride

A solution of hydrochloric acid (2.0 M in diethyl ether, 0.19 mL, 0.38 mmol, 1.0 eq.) was added dropwise to a stirred suspension of (E)-2-(2-(quinolin-2-yl)prop-1-enyl)phenol (100 mg, 0.38 mmol, 1.0 eq.) in dry diethyl ether (5 mL). The mixture was stirred at r.t. for 30 min and was filtered. The solids were washed with diethyl ether (2×5 mL) and were dried under reduced pressure yielding the product (90 mg, 80% yield) as a bright yellow solid; $^1$H NMR (400 MHz, DMSO-d$_6$) δ 2.41 (s, 3H, CH$_3$), 6.89 (t, J=7.5 Hz, 1H, Ar), 6.94 (d, J=7.5 Hz, 1H, Ar), 7.20 (t, J=7.5 Hz, 1H, Ar), 7.39 (d, J=7.5 Hz, 1H, Ar), 7.64 (s, 1H, C=CH), 7.72 (t, J=7.5 Hz, 1H, Ar), 7.92 (t, J=7.5 Hz, 1H, Ar), 8.13 (d, J=8.5 Hz, 2H, Ar), 8.27 (d, J=7.5 Hz, 1H, Ar), 8.71 (d, J=7.5 Hz, 1H, Ar), 9.88 (br s, 1H, OH).

Figure 33:
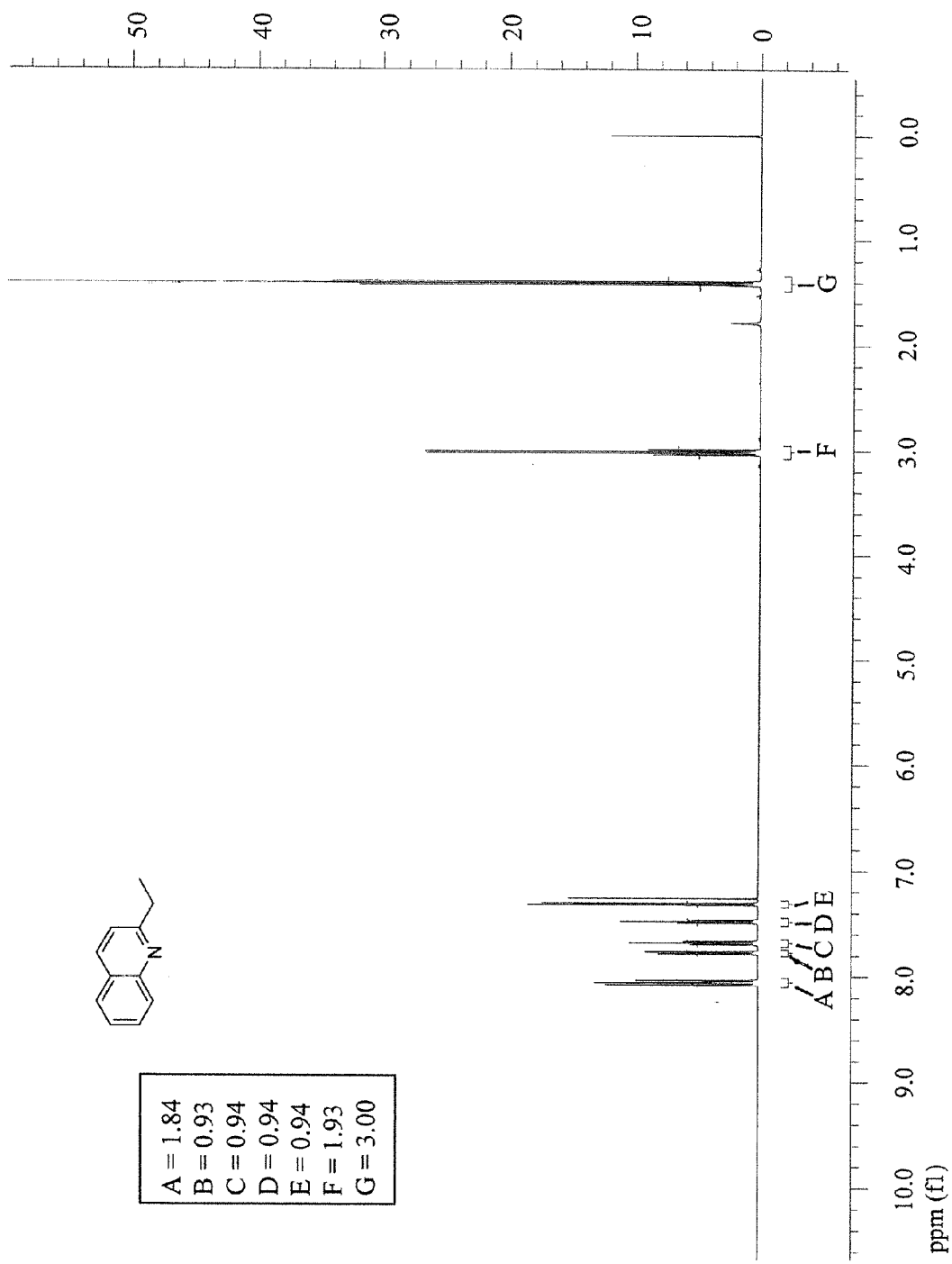
FIGS. 33 to 46 are NMR graphs for compounds according to the invention.
Figure 34:
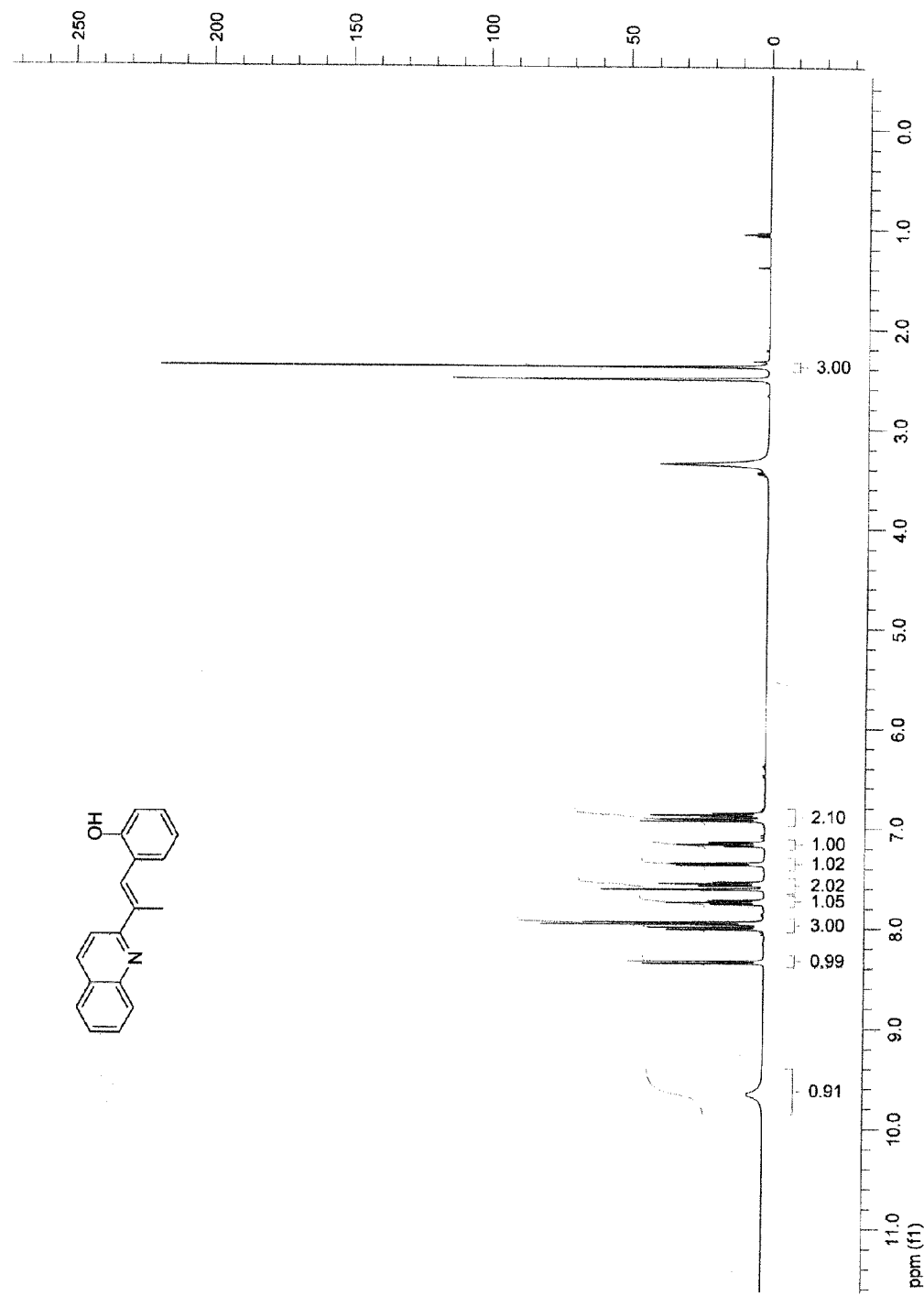
Figure 35:
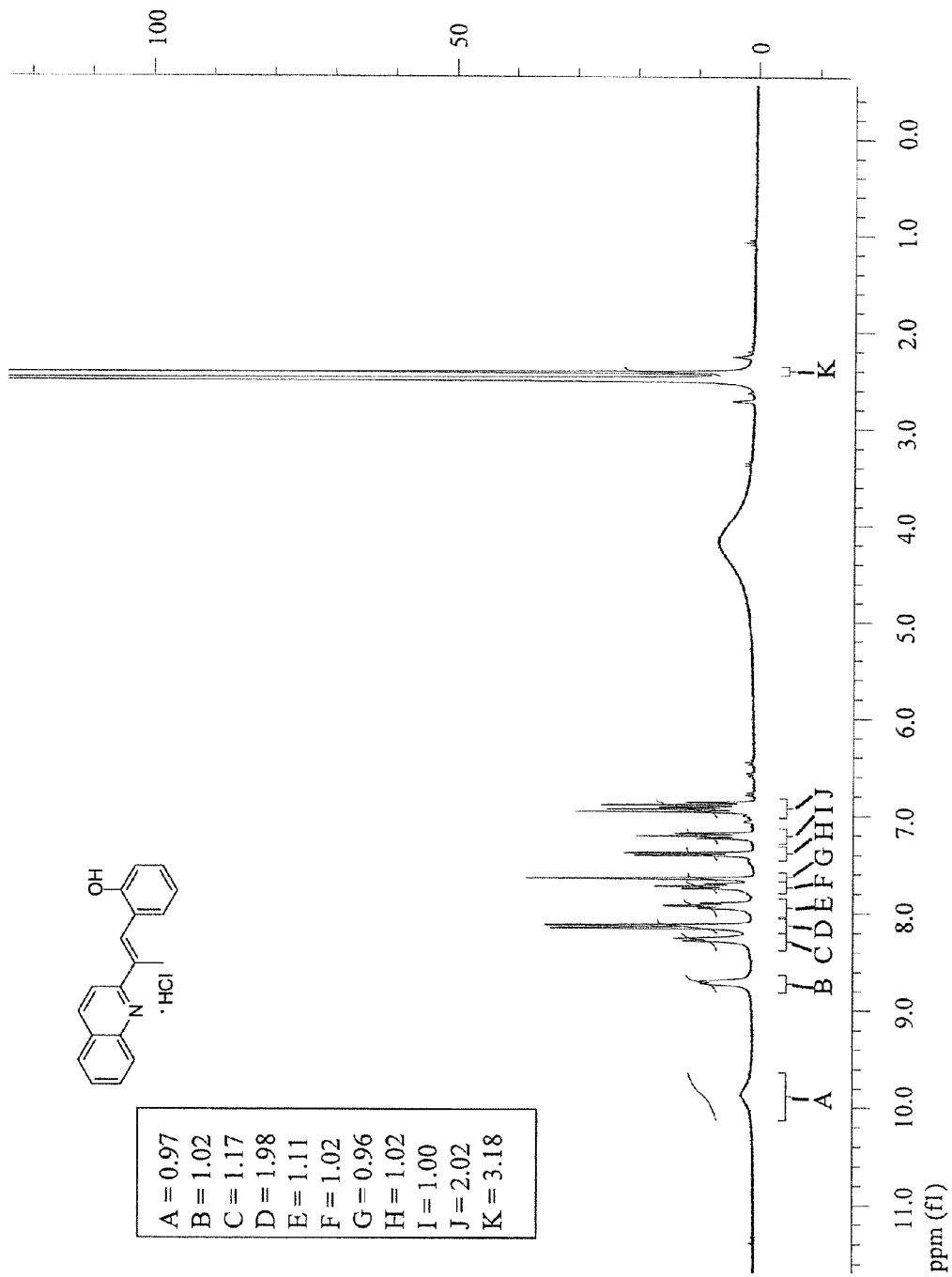

NMR data is also provided in the graphs FIGS. 33 to 35.

Synthesis of Compound CC16

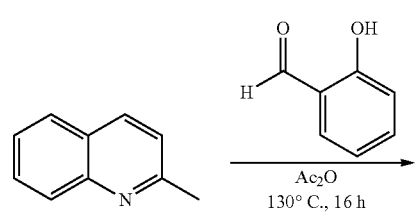

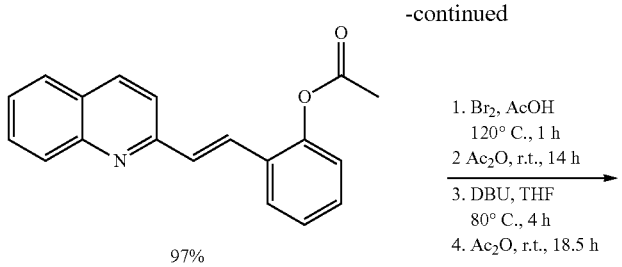

97%

1. Br₂, AcOH
   120° C., 1 h
2. Ac₂O, r.t., 14 h
3. DBU, THF
   80° C., 4 h
4. Ac₂O, r.t., 18.5 h

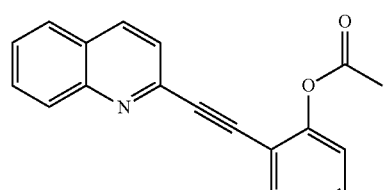

36%

1. K₂CO₃
   MeOH/THF
   r.t., 3 h
2. HCl

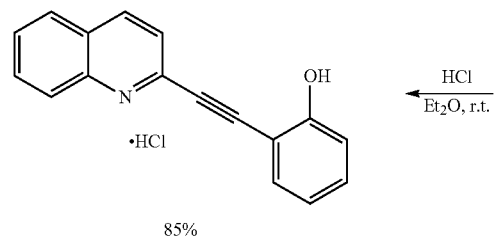

85%

HCl
Et₂O, r.t.

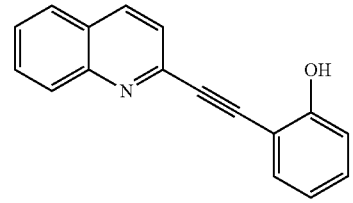

95%

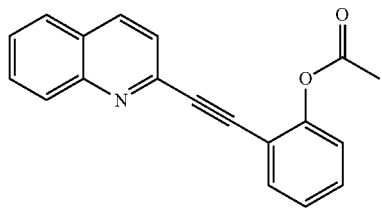 [SMILES: CC(=O)Oc1ccccc1C#Cc1ccc2ccccc2n1]

(E)-2-(2-(Quinolin-2-yl)vinyl)phenyl Acetate

Quinaldine (2.84 mL, 3.00 g, 21.0 mmol, 1.0 eq.) and 2-hydroxybenzaldehyde (2.23 mL, 2.56 g, 21.0 mmol, 1.0 eq.) were dissolved in acetic anhydride (25 mL). The resulting mixture was heated at 130° C. for 16 h. The mixture was allowed to cool down to r.t. and was poured onto water (150 mL) and was stirred vigorously. The mixture was extracted with ethyl acetate (3×75 mL). The combined organic extracts were washed with saturated aqueous ammonium acetate (2×75 mL) and brine (75 mL), dried over sodium sulfate and concentrated under reduced pressure which gave the crude product as a red oil. The crude product was purified by column chromatography (SiO₂, 1:4 ethyl acetate-cyclohexane) which yielded the product (5.88 g, 97% yield) as a clear yellow oil which crystallised upon standing.

2-(Quinolin-2-ylethynyl)phenyl Acetate

1. A solution of bromine (1.09 mL, 3.40 g, 21.3 mmol, 1.1 eq.) in acetic acid (3.0 mL) was added dropwise to a stirred solution of (E)-2-(2-(quinolin-2-yl)vinyl)phenyl acetate (5.60 g, 19.4 mmol, 1.0 eq.) in acetic acid (27 mL). The resulting mixture was heated at 120° C. for 1 h. The reaction was allowed to cool down to r.t. the reaction mixture was poured onto water (150 mL). The pH was adjusted to 7.0 by careful addition of aqueous sodium hydroxide (2 M). The mixture was extracted with ethyl acetate (3×100 mL) and the combined organic extracts were washed with brine (100 mL), dried over sodium sulfate and concentrated under reduced pressure which yielded a red viscous oil. The oil was dissolved in acetic anhydride (30 mL) and the mixture was stirred at r.t. for 14 h. The reaction mixture was poured onto water (150 mL) and the pH was carefully adjusted to 7.0. The mixture was extracted with ethyl acetate (3×100 mL) and the combined organic extracts were washed with brine (10 mL). The organic layer was dried over sodium sulfate and was concentrated under reduced pressure which gave a red semi-solid. The crude product was purified by column chromatography (SiO₂, 1:3 ethyl acetate-toluene) which gave the product (5.64 g) as a mixture of monobrominated compounds which was used without any further purification in the next step.

2. 1,8-Diazabicyclo[5.4.0]undec-7-ene (4.58 mL, 4.66 g, 30.6 mmol, 2.0 eq.) was added to a stirred solution of monobrominated 2-(quinolin-2-ylethynyl)phenyl acetate (5.64 g, 15.3 mmol, 1.0 eq.) in tetrahydrofuran (75 mL). The resulting mixture was heated at 80° C. for 4 h. The mixture was poured on water (200 mL) containing concentrated hydrochloric acid (37% in water, 1.55 g, 15.3 mmol, 1.0 eq.). The pH of the mixture was adjusted to 7.0 and was extracted with ethyl acetate (3×75 mL). The combined organic extracts were washed with brine (75 mL), dried over sodium sulfate and concentrated under reduced pressure. The residue was dissolved in acetic anhydride (30 mL) and the mixture was stirred at r.t. for 18 h. The reaction mixture was poured onto water (150 mL) and the pH was adjusted to 7.0 by careful addition of aqueous sodium hydroxide (5%). The mixture was extracted with ethyl acetate (3×75 mL). The combined organic extracts were washed with brine (100 mL), dried over sodium sulfate and were concentrated under reduced pressure which gave the crude product as a viscous red oil. The crude product was purified by column chromatography (SiO$_2$, 1:9 ethyl acetate-toluene) yielding the product (2.02 g, 36% yield) as an orange oil; $^1$H NMR (400 MHz, DMSO-d$_6$) δ 2.44 (s, 3H, CH$_3$), 7.32 (d, J=8.0 Hz, 1H, Ar), 7.39 (t, J=7.5 Hz, 1H, Ar), 7.56 (t, J=8.0 Hz, 1H, Ar), 7.66 (t, J=8.0 Hz, 1H, Ar), 7.69 (d, J=8.5 Hz, 1H, Ar), 7.76 (d, J=7.5 Hz, 1H, Ar), 7.83 (t, J=7.0 Hz, 1H, Ar), 8.02 (d, J=8.5 Hz, 1H, Ar), 8.03 (d, J=8.5 Hz, 1H, Ar), 8.44 (d, J=8.5 Hz, 1H, Ar).

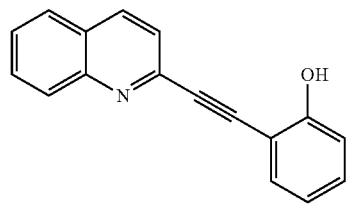 [SMILES: Oc1ccccc1C#Cc1ccc2ccccc2n1]

2-(Quinolin-2-ylethynyl)phenol

Potassium carbonate (0.48 g, 3.48 mmol, 2.0 eq.) was added to a stirred solution of 2-(quinolin-2-ylethynyl)phenyl acetate (0.50 g, 1.74 mmol, 1.0 eq.) in a 1:1 mixture of methanol-water (10 mL). The resulting mixture was stirred at r.t. for 3 h. The reaction was poured onto water (50 mL) and the pH was adjusted to 7.0 by careful addition of aqueous hydrochloric acid (10%). The mixture was extracted with ethyl acetate (3×25 mL). The combined organic extracts were washed with brine (25 mL), dried over sodium sulfate and were concentrated under reduced pressure yielding the product (0.42 g, 95%) as a pale yellow solid; $^1$H NMR (500 MHz, DMSO-d$_6$) δ 6.87 (t, J=7.5 Hz, 1H, Ar), 6.97 (d, J=8.0 Hz, 1H, Ar), 7.30 (t, J=8.0 Hz, 1H, Ar), 7.50 (d, J=7.5 Hz, 1H, Ar), 7.63 (t, J=7.5 Hz, 1H, Ar), 7.69 (d, J=8.5 Hz, 1H, Ar), 7.81 (t, J=7.0 Hz, 1H, Ar), 8.00 (d, J=7.0 Hz, 1H, Ar), 8.01 (d, J=7.0 Hz, 1H, Ar), 8.40 (d, J=8.5 Hz, 1H, Ar), 10.23 (s, 1H, OH).

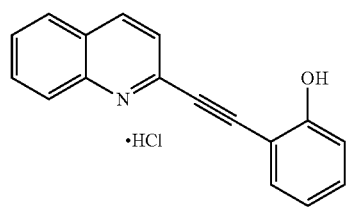 [SMILES: Oc1ccccc1C#Cc1ccc2ccccc2n1 ; Cl]

2-(Quinolin-2-ylethynyl)phenol Hydrochloride

A solution of hydrochloric acid (2.0 M in diethyl ether, 0.40 mL, 0.82 mmol, 1.0 eq.) was added dropwise to a stirred suspension of 2-(quinolin-2-ylethynyl)phenol (200 mg, 0.82 mmol, 1.0 eq.) in dry diethyl ether (10 mL). The mixture was stirred at r.t. for 30 min and was filtered. The solids were washed with diethyl ether (3×5 mL) and were dried under reduced pressure yielding the product (197 mg, 85% yield) as a bright yellow solid; $^1$H NMR (400 MHz, DMSO-d$_6$) δ 6.89 (t, J=7.5 Hz, 1H, Ar), 7.03 (d, J=8.0 Hz, 1H, Ar), 7.33 (t, J=8.0 Hz, 1H, Ar), 7.54 (d, J=7.5 Hz, 1H, Ar), 7.71 (t, J=7.5 Hz, 1H, Ar), 7.81 (d, J=8.5 Hz, 1H, Ar), 7.90 (t, J=7.0 Hz, 1H, Ar), 8.09 (d, J=8.0 Hz, 1H, Ar), 8.10 (d, J=8.0 Hz, 1H, Ar), 8.59 (d, J=8.5 Hz, 1H, Ar), 10.42 (br s, 1H, OH).

Figure 36:
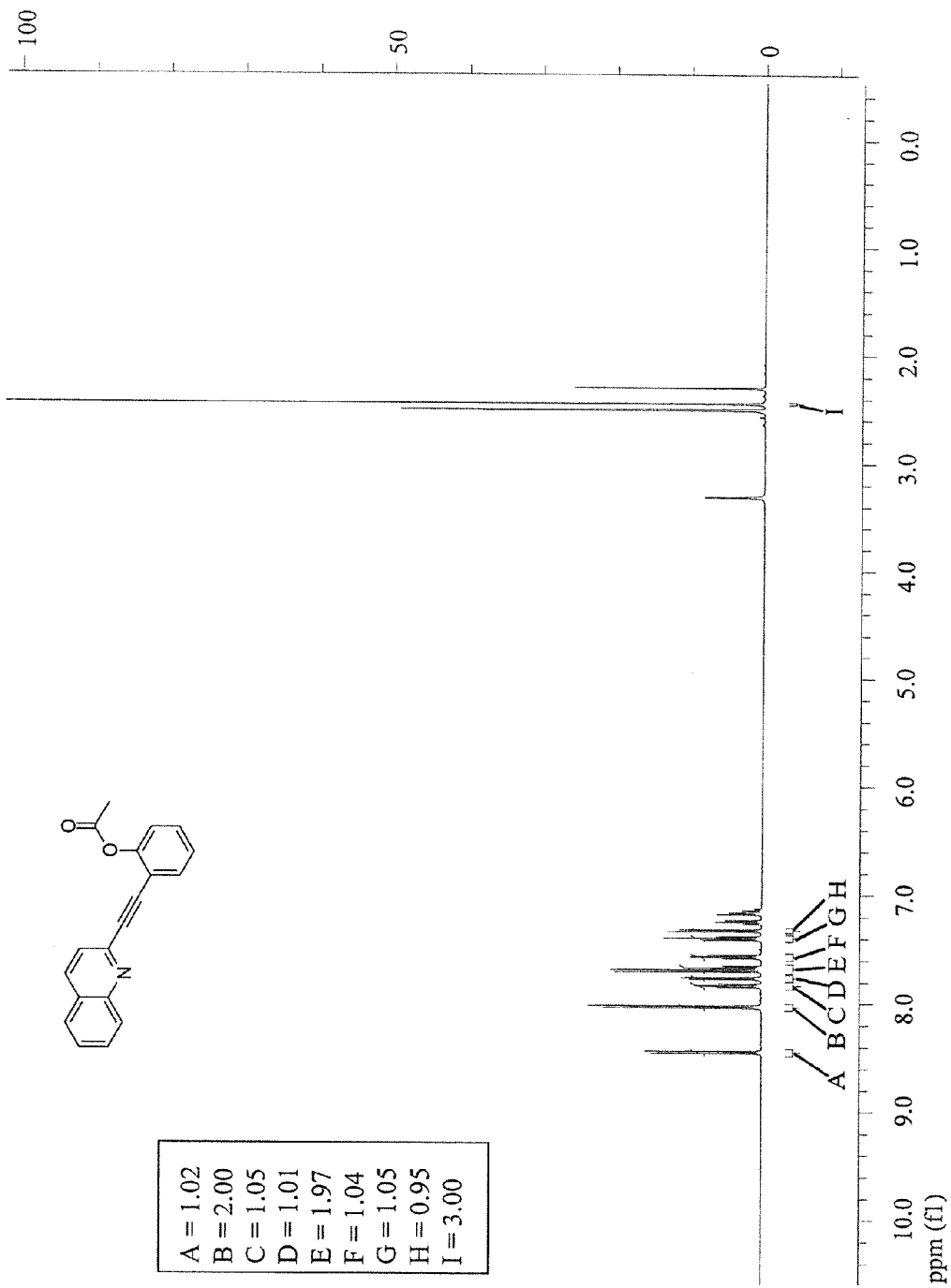
Figure 37:
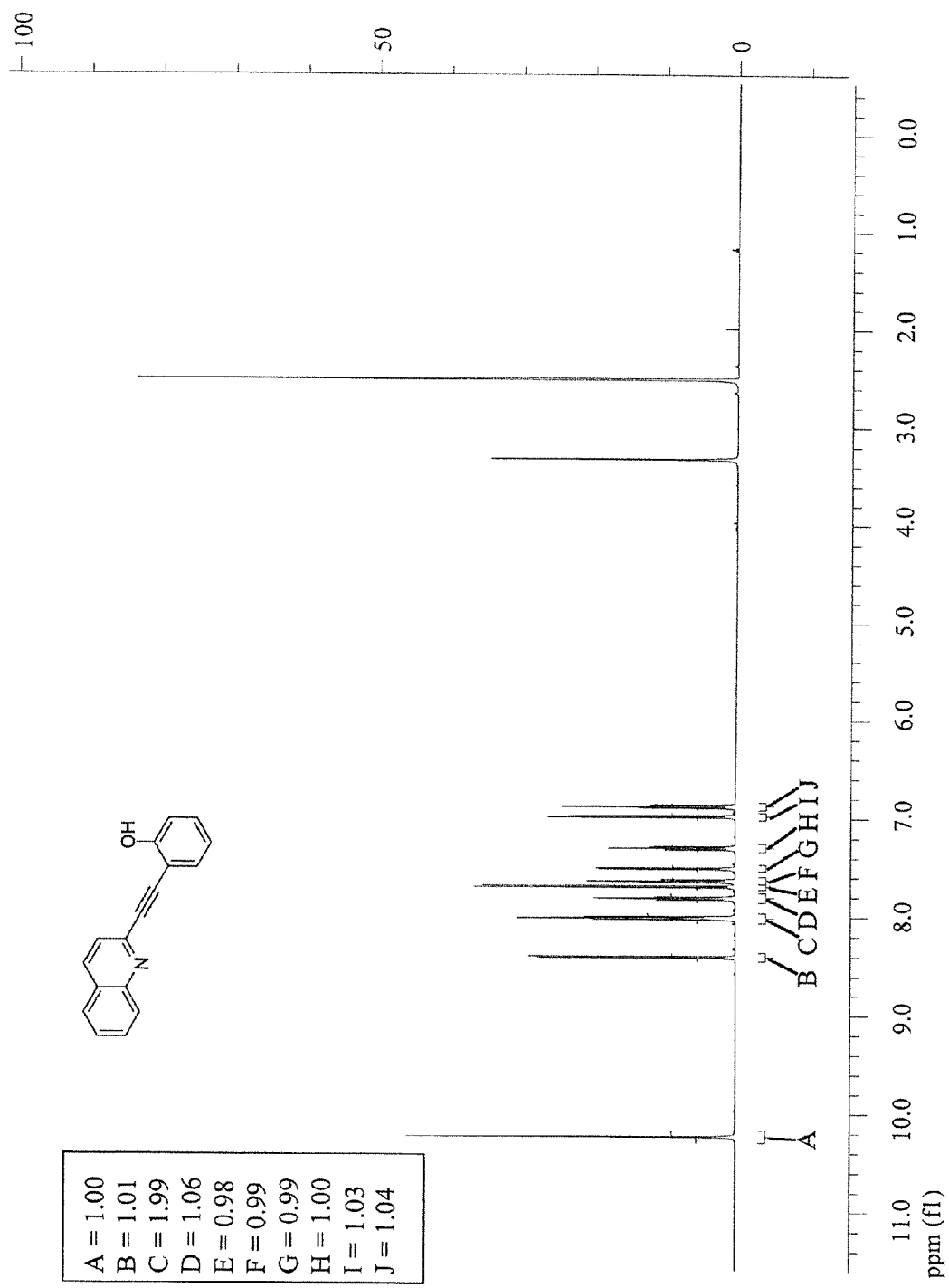
Figure 38:
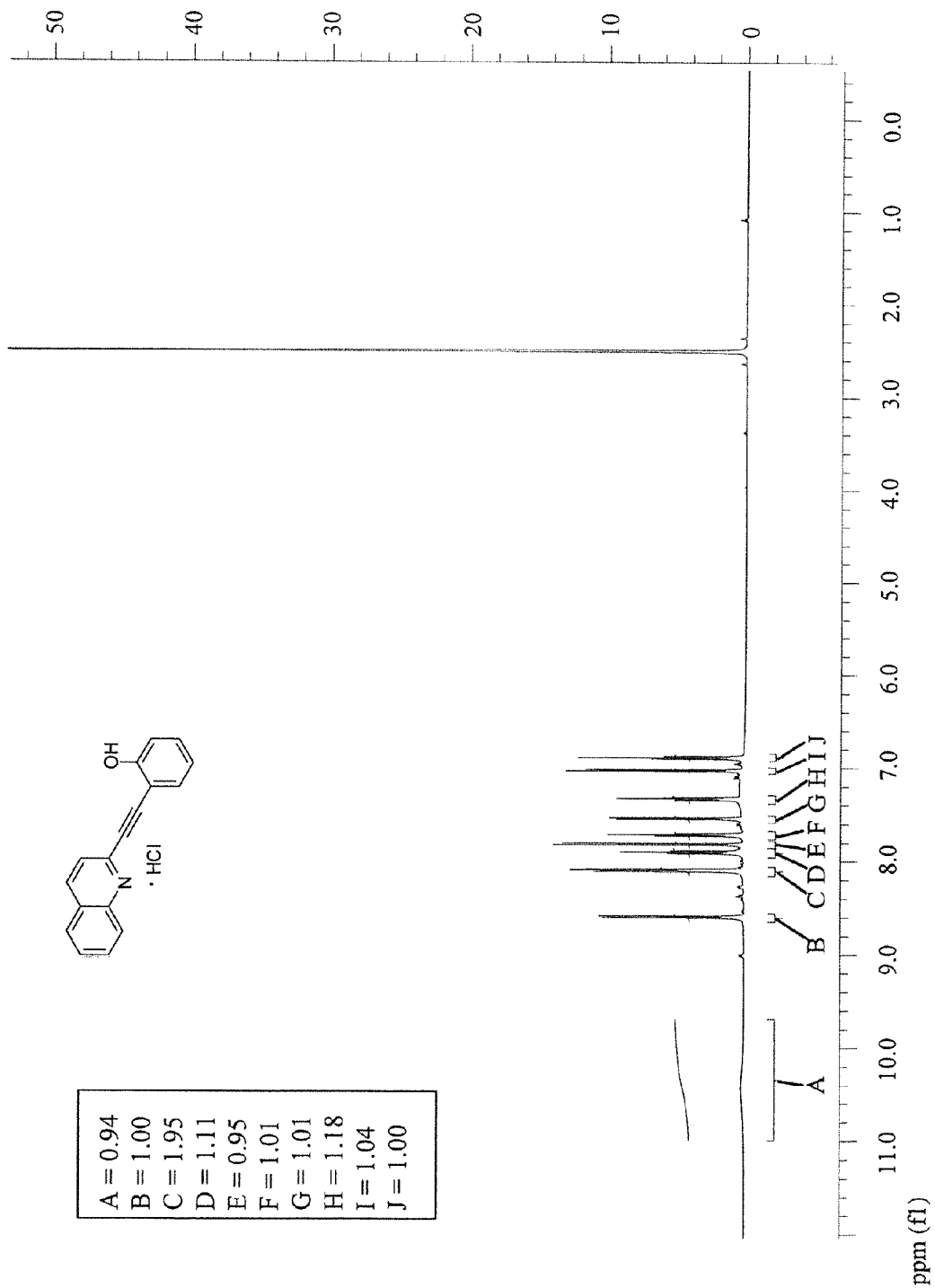

NMR data is also provided in the graphs FIGS. 36 to 38.

Synthesis of CC15

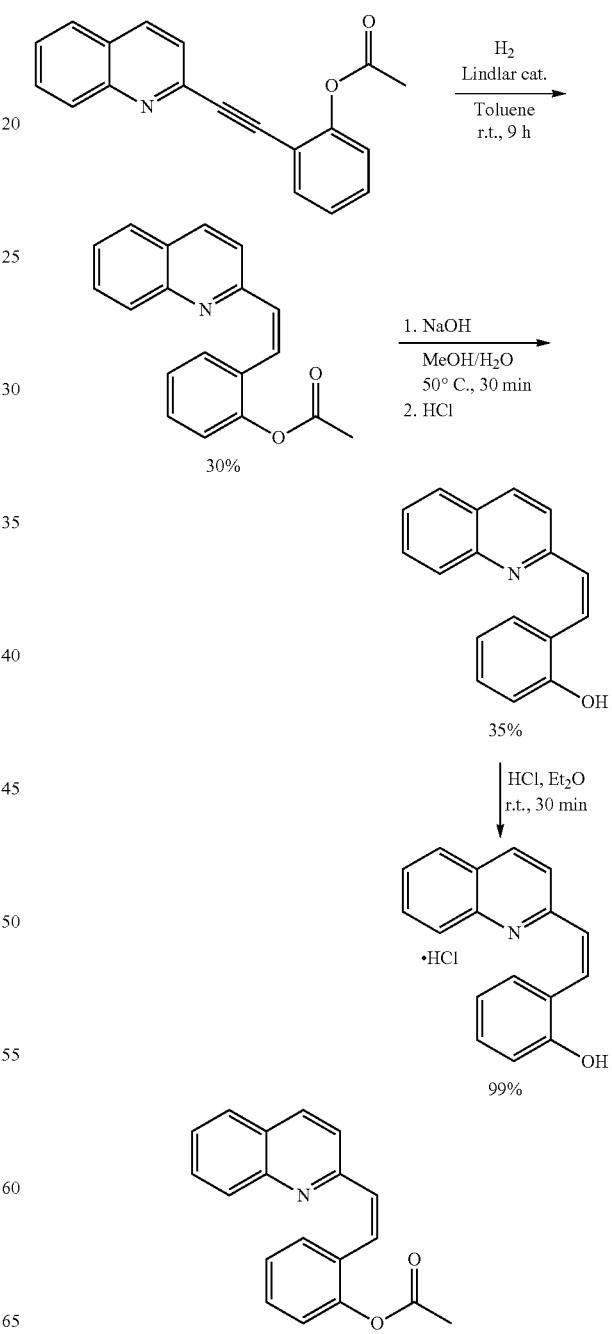

(Z)-2-(2-(Quinolin-2-yl)vinyl)phenyl Acetate

In an autoclave, 2-(quinolin-2-ylethynyl)phenyl acetate (0.40 g, 1.4 mmol, 1.0 eq.) was dissolved in degassed toluene (15 mL). Lindlar catalyst (5% Pd on $CaCO_3$, 80 mg) was added and the vessel was sealed. The mixture was hydrogenated under 4 bar pressure for 9 h at r.t. The mixture was filtered through a pad of Celite to remove the Pd catalyst and concentrated under reduced pressure which gave the crude product. The product was purified by column chromatography ($SiO_2$, 98.75:1:0.25 dichloromethane-methanol-ammonia) which yielded the product (0.12 g, 30% yield) as a tan solid.

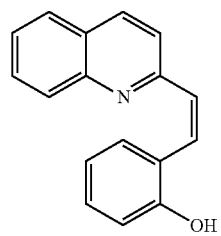 [SMILES: Oc1ccccc1/C=C\c1ccc2ccccc2n1]

(Z)-2-(2-(Quinolin-2-yl)vinyl)phenol.

Figure 39:
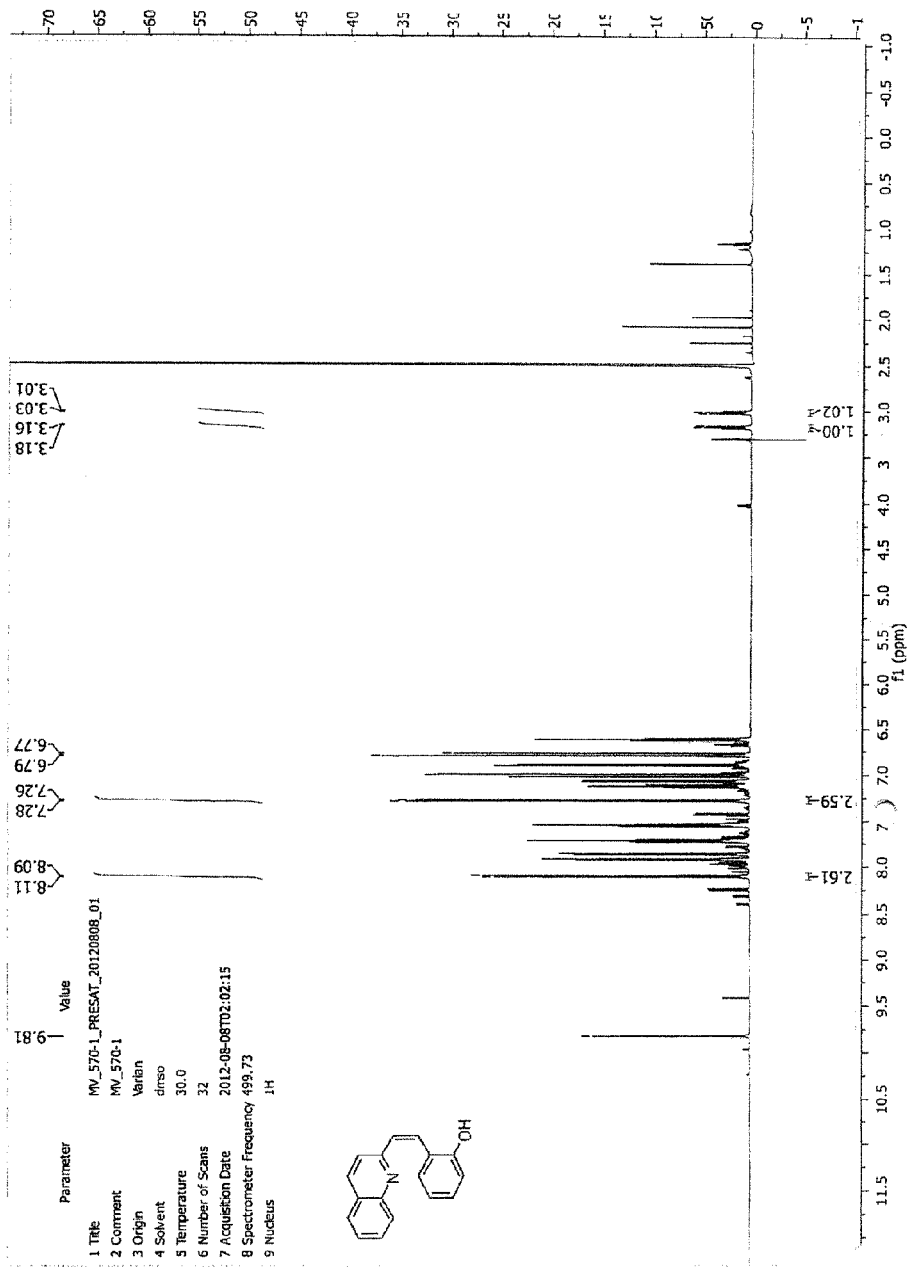

NMR data is presented in FIG. 39.

(Z)-2-(2-(Quinolin-2-yl)vinyl)phenyl acetate (0.12 g, 0.41 mmol, 1.0 eq.) was suspended in a mixture of methanol (2 mL) and water (2 mL). Aqueous sodium hydroxide (5 M, 1 mL) was added and the mixture was stirred at 50° C. for 30 min. The pH was adjusted to 6.5 by careful addition of aqueous hydrochloric acid (2 M). The mixture was extracted with ethyl acetate (3×mL), and the combined organic extracts were dried over sodium sulfate and concentrated under reduced pressure which yielded the product (40 mg, 35%) as a yellow solid.

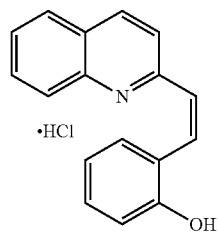 [SMILES: Oc1ccccc1/C=C\c1ccc2ccccc2n1 ; Cl]

(Z)-2-(2-(Quinolin-2-yl)vinyl)phenol Hydrochloride.

Figure 40:
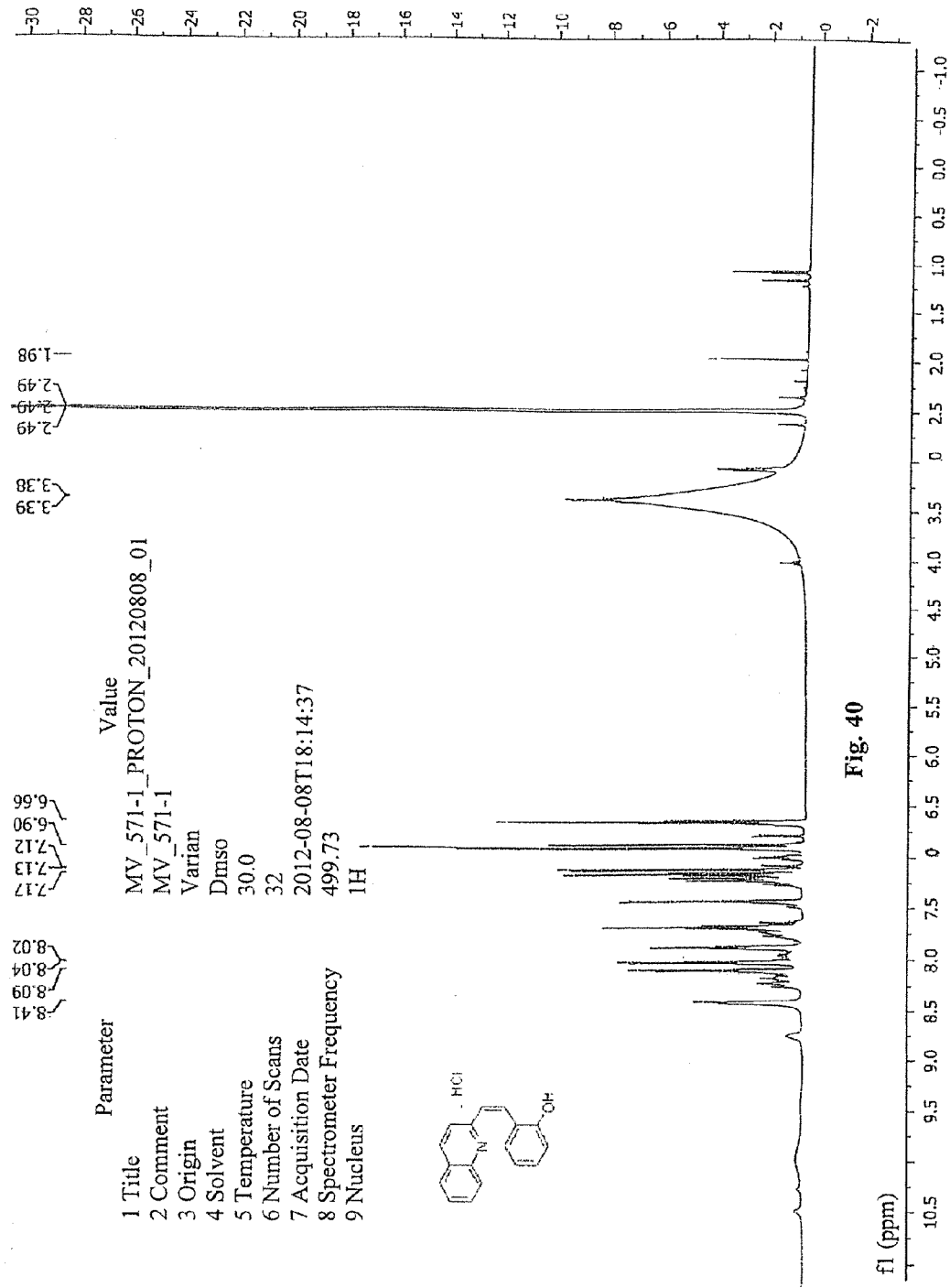

NMR data is presented in FIG. 40.

A solution of hydrochloric acid (2.0 M in diethyl ether, 0.12 mL, 0.24 mmol, 2.0 eq.) was added dropwise to a stirred suspension of (Z)-2-(2-(quinolin-2-yl)vinyl)phenol (30 mg, 0.12 mmol, 1.0 eq.) in dry diethyl ether (3 mL). The mixture was stirred at r.t. for 30 min and was filtered. The solids were washed with diethyl ether (2×1 mL) and were dried under reduced pressure yielding the product (36 mg, 99% yield) as a bright yellow solid.

Synthesis of CC4

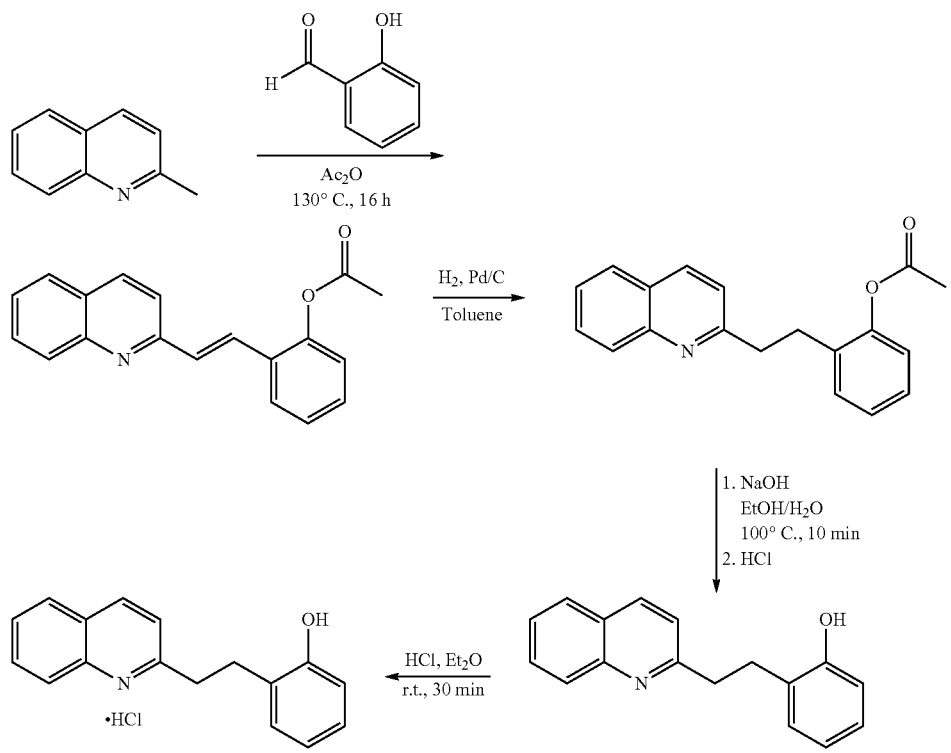

Figure 41:
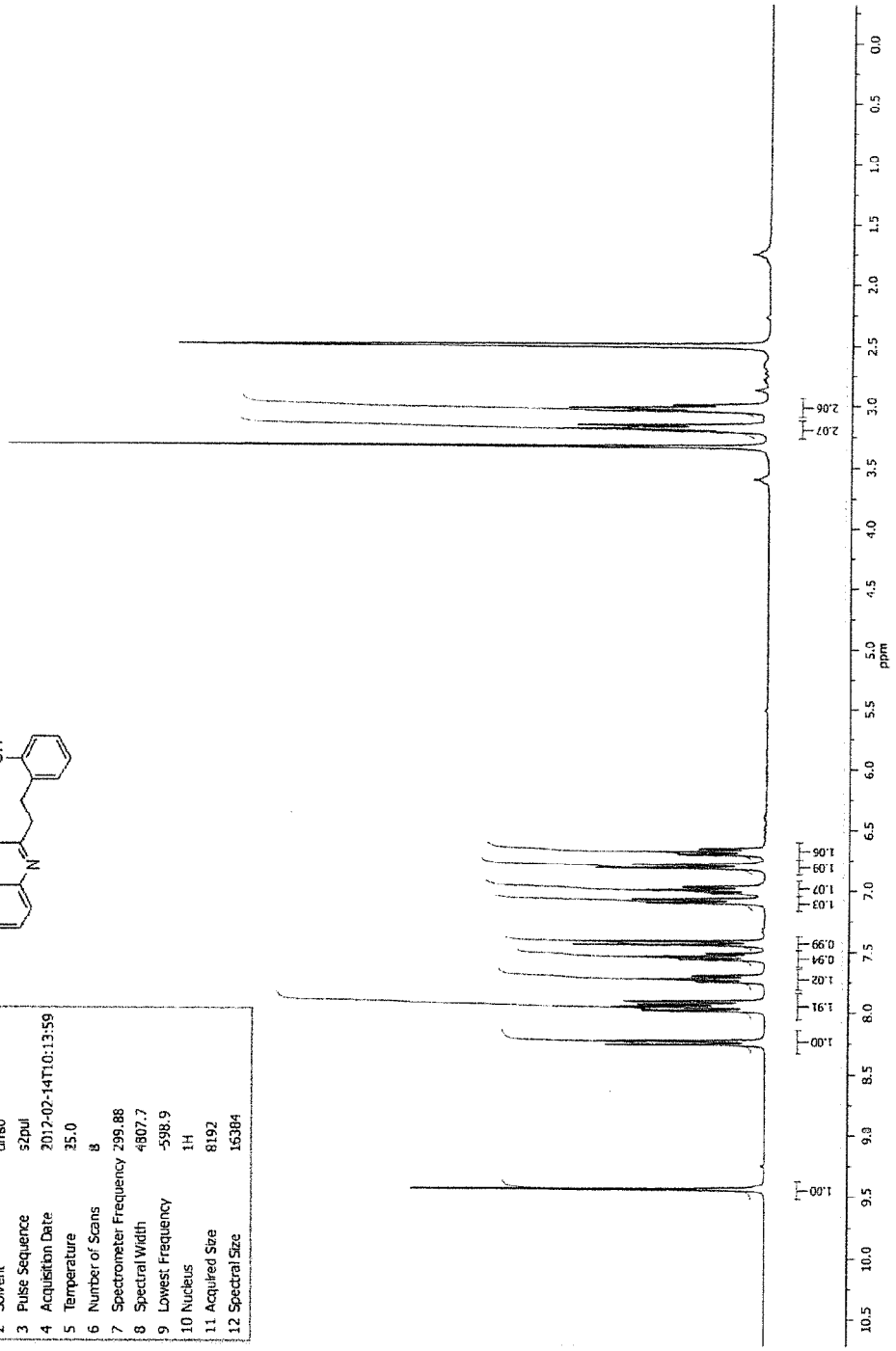
Figure 42:
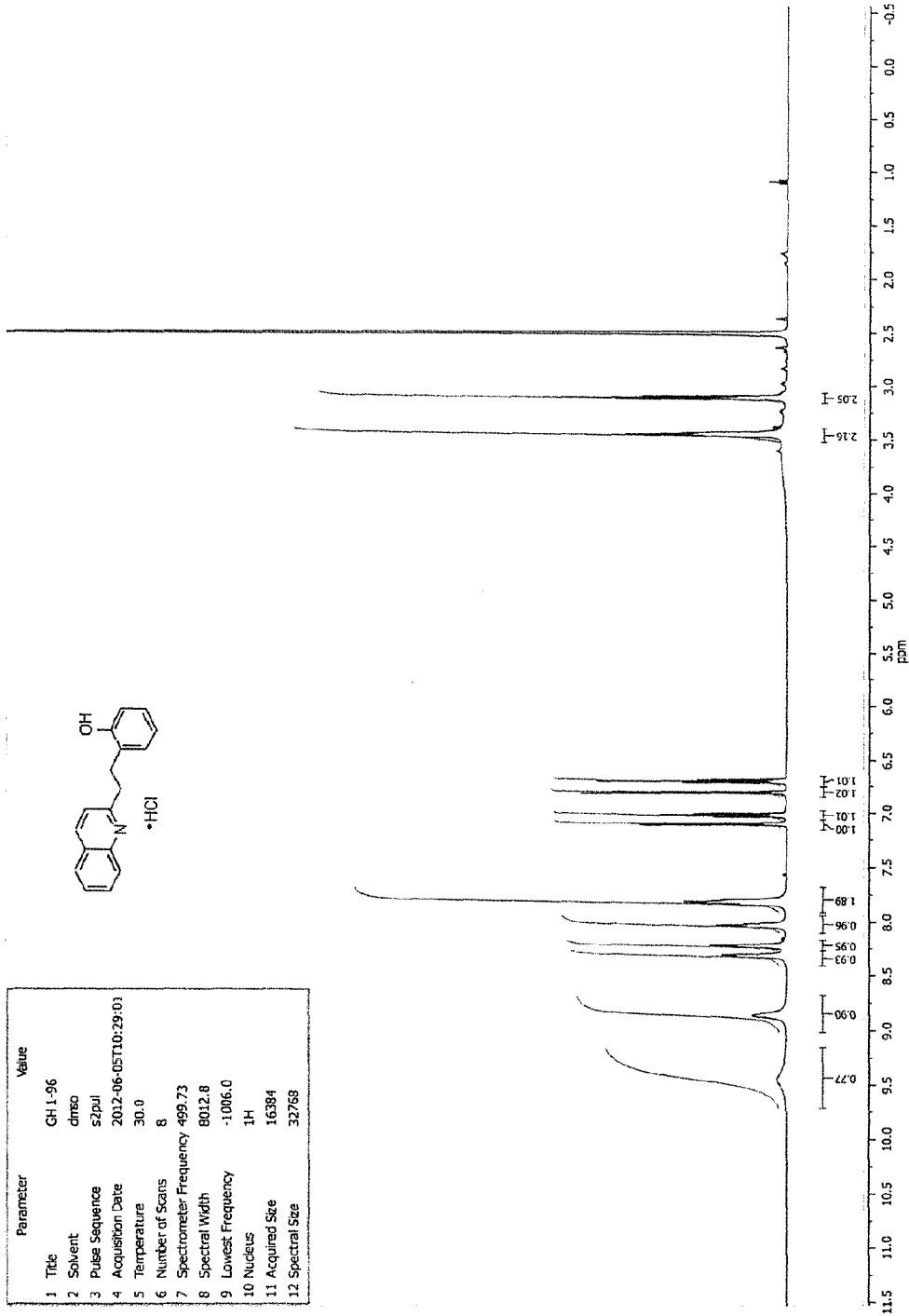

NMR data is presented in FIGS. 41 and 42.

Figure 43:
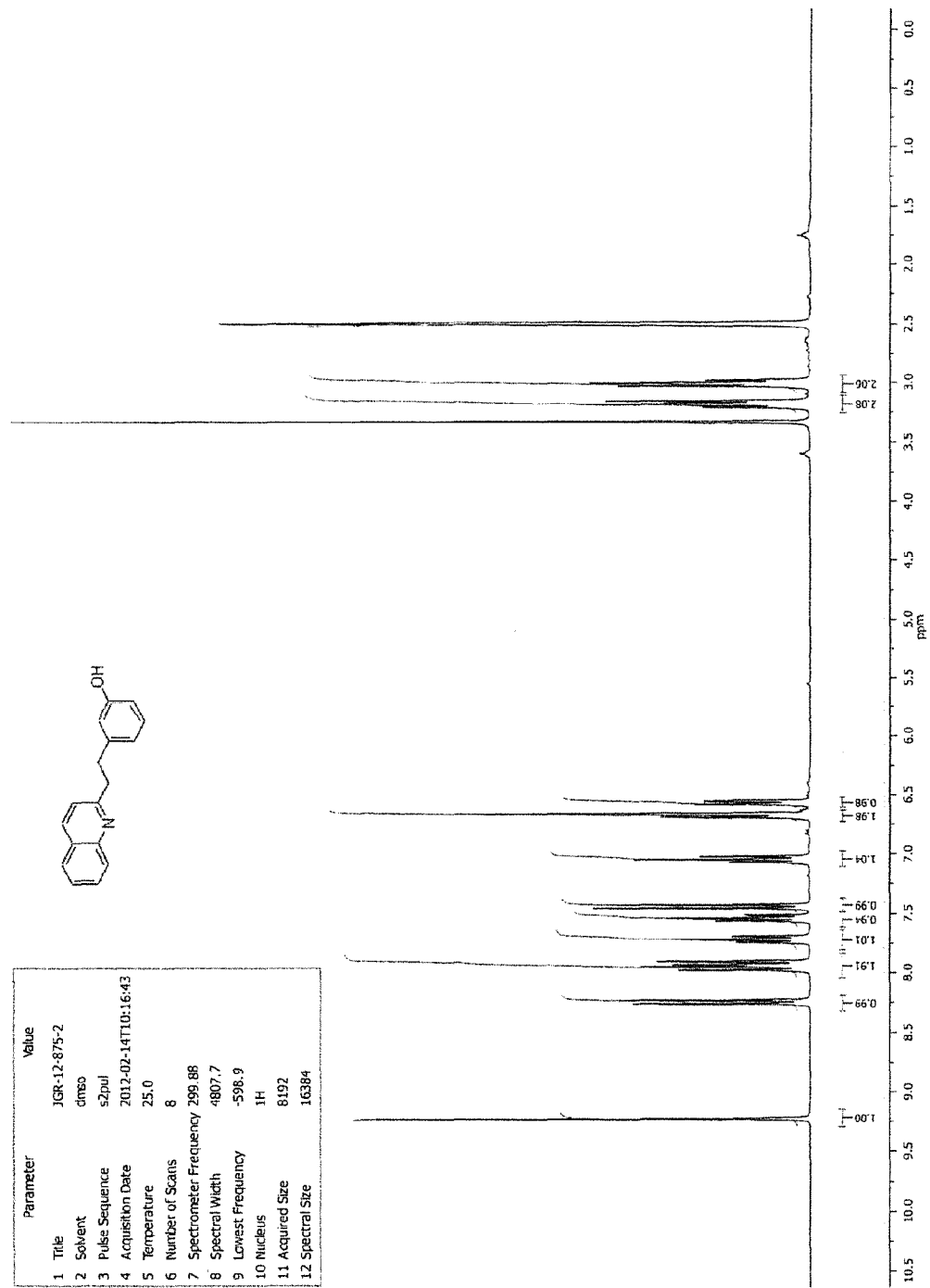
Figure 44:
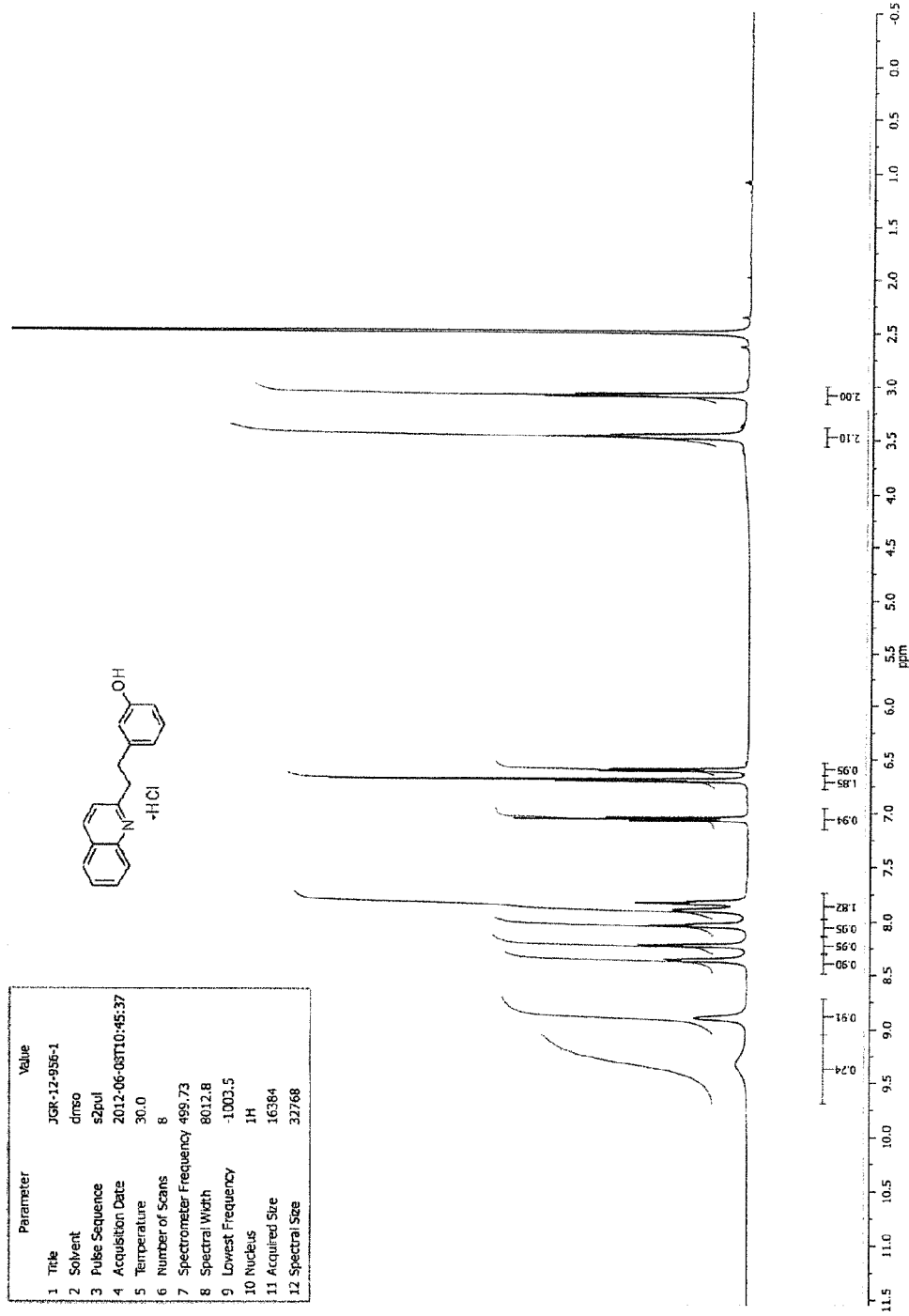
Figure 45:
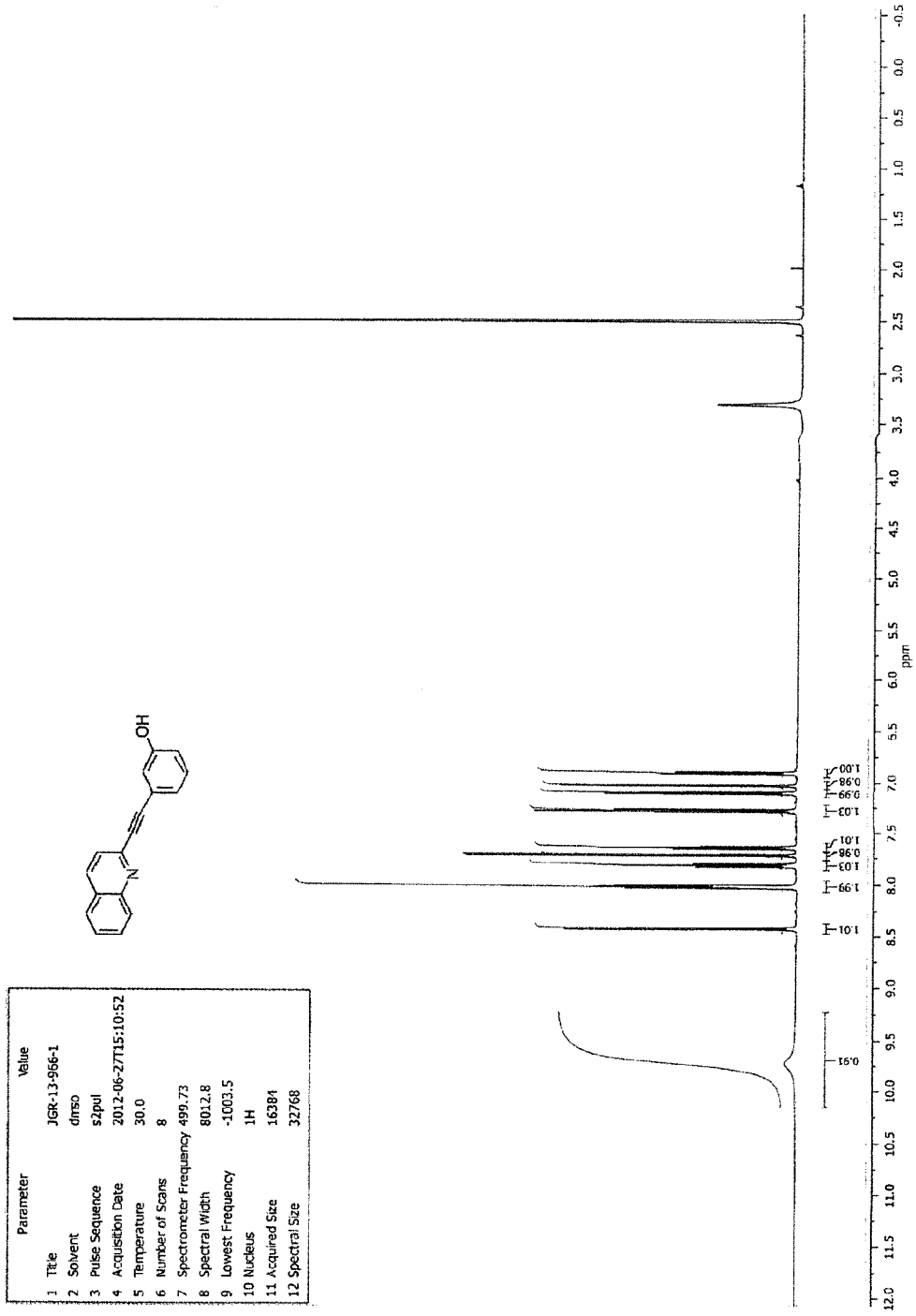
Figure 46:
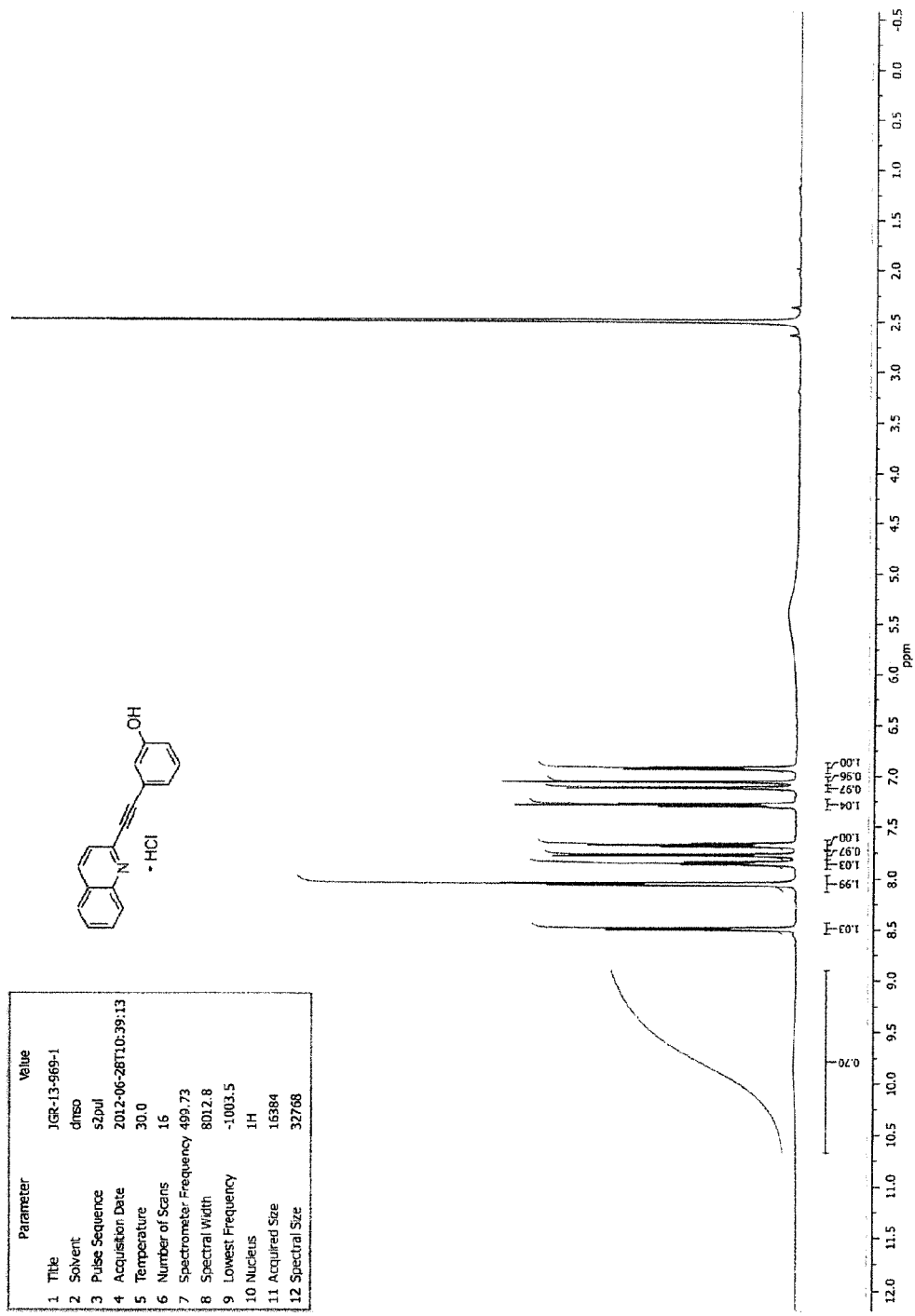

Synthesis of CC5
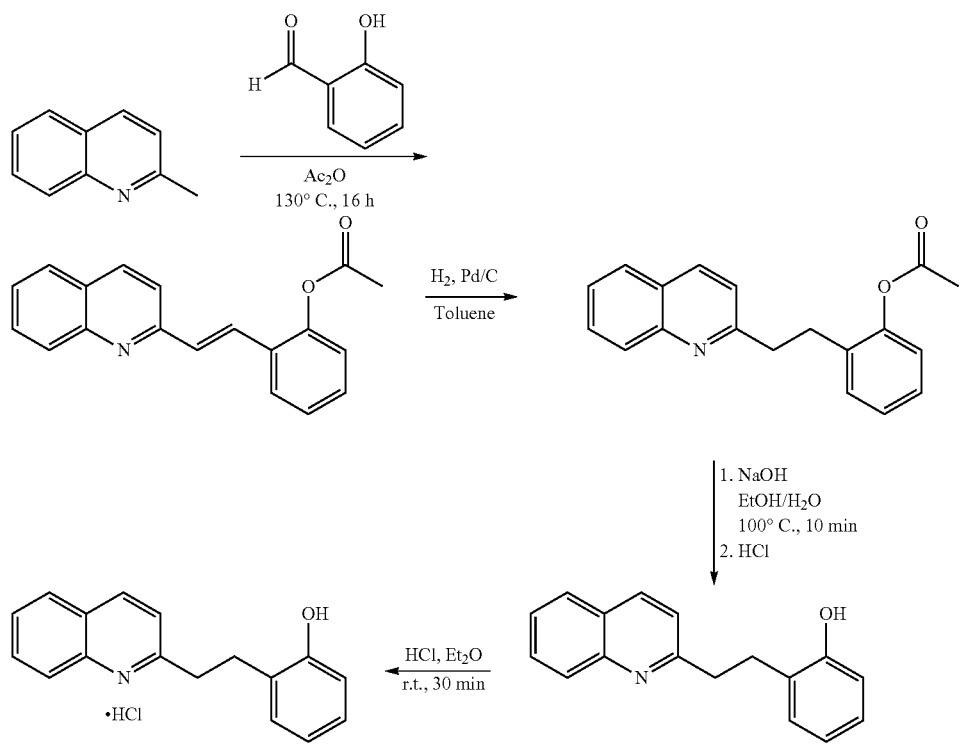
NMR data is presented in FIGS. 43 and 44.
Synthesis of CC15
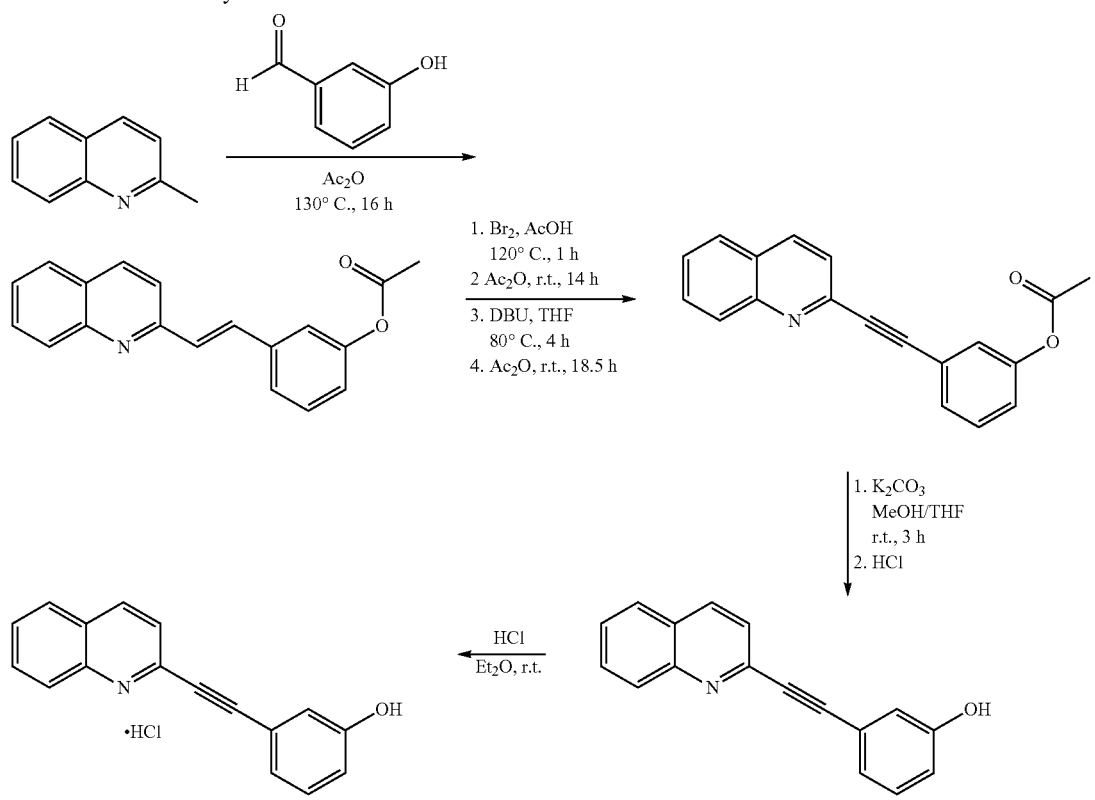
NMR data is presented in FIGS. 45 and 46.

Compound 11B_Z-isomer has CAS #1036287-19-0

Reference 1: Homology modeling and site-directed mutagenesis to identify selective inhibitors of endothelin-converting enzyme-2. Gagnidze K, Sachchidanand, Rozenfeld R, Mezei M, Zhou M M, Devi L A. J Med Chem. 2008 Jun. 26; 51(12):3378-87.

Reference 2: Spectral and photochemical properties of hydroxylated 2-styrylquino line derivatives. Budyka, M. F., Potashova, N. I., Gavrishova, T. N., Lee, V. M. High Energy Chemistry. July 2011, Vol. 45 Issue 4, p 281-286.

Reference 3: High Energy Chemistry. July 2011, Vol. 45 Issue 4, p 273-280. Quantum-chemical study of photoisomerization and photoinduced proton transfer in hydroxystyrylquinolines. Budyka, M. F.

Compound 11B_CC2 has CAS#143816-40-4.

Reference: J Med Chem. 1992 Oct. 16; 35(21):3832-44. Development of a novel series of styrylquino line compounds as high-affinity leukotriene D4 receptor antagonists: synthetic and structure-activity studies leading to the discovery of (+-)-3-[[[3-[2-(7-chloro-2-quinolinyl)-(E)-ethenyl]phenyl][[3-(dimethylamino)-3-oxopropyl]thio]methyl]thio]propionic acid. Zamboni R, Belley M, Champion E, Charette L, DeHaven R, Frenette R, Gauthier J Y, Jones T R, Leger S, Masson P, et al.

Compound 11B-268 has CAS #77669-18-2

Reference 1. A Catalyst-Free Benzylic C—H Bond Olefination of Azaarenes for Direct Mannich-like Reactions Yan, Yizhe; Xu, Kun; Fang, Yang; Wang, Zhiyong Journal of Organic Chemistry (2011), 76(16), 6849-6855.

Reference 2. Photophysics and excited-state proton transfer of 2'-hydroxy-2-trans-styrylquinoline Wang, Shun-Li; Yeh, Tzu-Wei; Ho, Tong-Ing Chemical Physics Letters (2006), 418(4-6), 397-401.

Reference 3. IR-, 1H-NMR- and TLC examination of new 2-styrylquinolines with antibacterial activity Chervenkov, S. K.; Pavlov, A. I.; Slavova, S. T. Analytical Letters (1995), 28(1), 59-70.

Reference 4. Di- and tri-methoxystyryl derivatives of heterocyclic nitrogen compounds Bahner, C. T.; Rives, L. M.; McGaha, S. W.; Rutledge, D.; Ford, D.; Gooch, E.; Westberry, D.; Ziegler, D.; Ziegler, R. Arzneimittel-Forschung (1981), 31(3), 404-6.

Compound 11B-438 has CAS #77669-18-2
Compound 11B-814 has CAS #853725-50-5
Compound 11B-470 has CAS #190437-90-2

Reference 1, Experimental and quantum chemical investigation of photochemical properties of a covalently bound bis(styrylquinoline) dyad Budyka, M. F.; Potashova, N. I.; Gavrishova, T. N.; Lee, V. M. High Energy Chemistry (2012), 46(5), 309-322.

Reference 2. Energy transfer, fluorescence and photoisomerization of styrylquinoline-naphthol dyads with dioxypolymethylene bridges Budyka, Mikhayl F.; Sadykova, Kristina F.; Gavrishova, Tatiana N. Journal of Photochemistry and Photobiology, A: Chemistry (2012), 241, 38-44.

Reference 3. Spectral-Luminescent properties of the dioxytetramethylene-bridged naphthol-styrylquinoline dyad Budyka, M. F.; Sadykova, K. F.; Gavrishova, T. N.; Gak, V. Yu. High Energy Chemistry (2012), 46(1), 38-43.

Reference 4. A general protocol for the solvent- and catalyst-free synthesis of 2-styrylquinolines under focused microwave irradiation Staderini, Matteo; Cabezas, Nieves; Bolognesi, Maria Laura; Menendez, J. Carlos Synlett (2011), (17), 2577-2579.

Reference 5. A Catalyst-Free Benzylic C—H Bond Olefination of Azaarenes for Direct Mannich-like Reactions Yan, Yizhe; Xu, Kun; Fang, Yang; Wang, Zhiyong Journal of Organic Chemistry (2011), 76(16), 6849-6855.

Reference 6. Highly Enantioselective Iridium-Catalyzed Hydrogenation of 2-Benzylquinolines and 2-Functionalized and 2,3-Disubstituted Quinolines Wang, Da-Wei; Wang, Xiao-Bing; Wang, Duo-Sheng; Lu, Sheng-Mei; Zhou, Yong-Gui; Li, Yu-Xue Journal of Organic Chemistry (2009), 74(7), 2780-2787.

Reference 7. Substituent effects on intramolecular charge-transfer behavior of styrylheterocycles Wang, S.-L.; Ho, T.-I. Journal of Photochemistry and Photobiology, A: Chemistry (2000), 135(2-3), 119-126.

Reference 8. Compositions and methods for treating bone deficit conditions Orme, Mark W.; Baindur, Nand; Robbins, Kirk G.; et al. PCT Int. Appl. (1998), WO 9817267 A1 19980430.

Reference 9. Preparation of (hetero)aromatic compounds for treating bone deficit conditions. Petrie, Charles; Orme, Mark W.; Baindur, Nand; Robbins, Kirk G.; Harris, Scott M.; Kontoyianni, Maria; Hurley, Laurence H.; Kerwin, Sean M.; Mundy, Gregory R. PCT Int. Appl. (1997), WO 9715308 A1 19970501.

Compound 11B-074 has CAS #701255-10-9
Compound 11B-471 has CAS #143816-38-0

Reference 1. Synthesis and antifungal activity of diverse C-2 pyridinyl and pyridinylvinyl substituted quinolines Kouznetsov, Vladimir V.; Melendez Gomez, Carlos M.; Derita, Marcos G.; Svetaz, Laura; del Olmo, Esther; Zacchino, Susana A. Bioorganic & Medicinal Chemistry (2012), 20(21), 6506-6512.

Reference 2. Microwave-assisted solvent-free synthesis of 2-styrylquinolines in the presence of zinc chloride Li, V. M.; Gavrishova, T. N.; Budyka, M. F. Russian Journal of Organic Chemistry (2012), 48(6), 823-828.

Reference 3. Development of a novel series of styrylquinoline compounds as high-affinity leukotriene D4 receptor antagonists: synthetic and structure-activity studies leading to the discovery of (±)-3-[[[3-[2-(7-chloro-2-quinolinyl)-(E)-ethenyl]phenyl][[3-(dimethylamino)-3-oxopropyl]thio]methyl]thio]propionic acid. Zamboni, R.; Belley, M.; Champion, E.; Charette, L.; DeHaven, R.; Frenette, R.; Gauthier, J. Y.; Jones, T. R.; Leger, S.; et al. Journal of Medicinal Chemistry (1992), 35(21), 3832-44.

Compound 11B-739 has CAS #1422255-33-1

Reference 1. Contribution to investigation of antimicrobial activity of styrylquinolines Cieslik, Wioleta; Musiol, Robert; Nycz, Jacek E.; Jampilek, Josef; Vejsova, Marcela; Wolff, Mariusz; Machura, Barbara; Polanski, Jaroslaw Bioorganic & Medicinal Chemistry (2012), 20(24), 6960-6968.

Compound 11B has CAS #143816-42-6

Reference 1. Contribution to investigation of antimicrobial activity of styrylquinolines. Cieslik, Wioleta; Musiol, Robert; Nycz, Jacek E.; Jampilek, Josef; Vejsova, Marcela; Wolff, Mariusz; Machura, Barbara; Polanski, Jaroslaw. Bioorganic & Medicinal Chemistry (2012), 20(24), 6960-6968.

Reference 2. Microwave-assisted solvent-free synthesis of 2-styrylquinolines in the presence of zinc chloride. Li, V. M.; Gavrishova, T. N.; Budyka, M. F. Russian Journal of Organic Chemistry (2012), 48(6), 823-828.

Reference 3. Quantum-chemical study of photoisomerization and photoinduced proton transfer in hydroxystyrylquinolines. Budyka, M. F. High Energy Chemistry (2011), 45(4), 273-280.

Reference 4. Spectral and photochemical properties of hydroxylated 2-styrylquinoline derivatives. Budyka, M. F.;

Potashova, N. I.; Gavrishova, T. N.; Lee, V. M. High Energy Chemistry (2011), 45(4), 281-286.

Reference 5. Homology Modeling and Site-Directed Mutagenesis To Identify Selective Inhibitors of Endothelin-Converting Enzyme-2. Gagnidze, Khatuna; Sachchidanand; Rozenfeld, Raphael; Mezei, Mihaly; Zhou, Ming-Ming; Devi, Lakshmi A. Journal of Medicinal Chemistry (2008), 51(12), 3378-3387.

Reference 6. Photophysics and excited-state proton transfer of 2'-hydroxy-2-trans-styrylquinoline. Wang, Shun-Li; Yeh, Tzu-Wei; Ho, Tong-Ing. Chemical Physics Letters (2006), 418(4-6), 397-401.

Reference 7. Development of a novel series of styrylquinoline compounds as high-affinity leukotriene D4 receptor antagonists: synthetic and structure-activity studies leading to the discovery of (±)-3-[[[3-[2-(7-chloro-2-quinolinyl)-(E)-ethenyl]phenyl][[3-(dimethylamino)-3-oxopropyl]thio]methyl]thio]propionic acid. Zamboni, R.; Belley, M.; Champion, E.; Charette, L.; DeHaven, R.; Frenette, R.; Gauthier, J. Y.; Jones, T. R.; Leger, S.; et al. Journal of Medicinal Chemistry (1992), 35(21), 3832-44.

Compound 11B HCl has CAS #1379458-56-6

TABLE 3

Compounds 4H, 11A and 11C

| Structure | Code name | Chemical name |
|---|---|---|
| Structure XVIII | 4H | N'-[1-(2,4-dimethylphenyl)-2,5-dioxo-3-pyrrolidinyl]benzohydrazide |
| Structure XIX | 11A | (5-bromo-N'-[2-(trifluromethyl)benzylidene]-2-furohydrazide) |
| Structure XX | 11C | (3-(1,3-benzodioxol-5-yl-N-(3-pyridinylmethyl)acrylamide) |

TABLE 2

11F-522 Series Compounds

| Structure | Code name | Chemical name |
|---|---|---|
| | 11F-325 | 2-(1,3benzodioxol-5-ylmethyl)-1,2,3,4-tetrahydroisoquinoline |
| | 11F-199 | 2-(1,3benzodioxol-5-ylmethyl)-6,7-dimethoxy-1,2,3,4-tetrahydroisoquinoline |
| Structure XVI | 11F-708 | 2-[(7-methoxy-1,3-benzodioxol-5-yl)methyl]-1,2,3,4-tetrahydroisoquinoline |
| | 11F-050 | 6,7-dimethoxy-2-[(7-methoxy-1,3-benzodioxol-5-yl)methyl]-1,2,3,4-tetrahydroisoquinoline |
| | 11F-330 | 1-(3-chlorophenyl)-6,7-dimethoxy-2-[(7-methoxy-1,3-benzodioxol-5-yl)methyl]-1,2,3,4-tetrahydroisoquinoline |
| | 11F-393 | 2,3-dimethoxy-6-methyl-5,7,8,15-tetrahydrobenzo[c][1,3]benzodioxolo[5,6,g]azecin-14(6H)-one |
| | 11F-289 | 1-(1,3-benzodioxol-5-ylcarbonyl)-6-fluoro-2-methyl-1,2,3,4-tetrahydroquinoline |
| Structure XV | 11F-978 | 4-(1,3-benzodioxol-5-yl)-2-(3,4-dihydro-2(1H)-isoquinolinylmethyl)phenol |
| | 11F-412 | 7-(3,4-dimethylphenyl)-7,8-dihydro-6H-[1,3]dioxolo[4,5-g][1,3]benzoxazine |
| Structure XIV | 11F-001 | 1-(6-bromo-1,3-benzodioxol-5-yl)-6,7-diethoxy-1,2,3,4-tetrahydroisoquinoline |
| | 11F-5199 | 3-(1,3-benzodioxol-5-yl)-6-chloro-5,7-dimethyl-3,4-dihydro-2H-1,3-benzoxazine |
| | 11F-205 | 7-(1,3-benzodioxol-5-yl)-7,8-dihydro-6H-[1,3]dioxolo[4,5-g][1,3]-benzoxazine |
| | 11F-053 | 1-(1,3-benzodioxol-5-yl)-6,7-diethoxy-3,4-dihydro-1H-isochromene |
| | 11F-794 | 1-(1,3-benzodioxol-5-ylmethyl)-4-(3,4,5-trimethoxybenzyl)piperazine |
| | 11F-CC2 | (rac)-6,7-Dimethoxy-1-phenyl-1,2,3,4-tetrahydro-isoquinoline |
| | 11F-CC2-HCl | (rac)-6,7-Dimethoxy-1-phenyl-1,2,3,4-tetrahydro-isoquinoline HCl salt |
| | 11F-CC3 | (rac)-1-Benzo[1,3]dioxol-5-yl-6,7-dimethoxy-1,2,3,4-tetrahydro-isoquinoline |
| | 11F-CC4 | (rac)-6,7-Dimethoxy-2-methyl-1-phenyl-1,2,3,4-tetrahydro-isoquinoline |
| | 11F-CC5 | (rac)-3-(6,7-Dimethoxy-1,2,3,4-tetrahydroisoquinolin-1-yl)-phenol |
| | 11F-CC6 | (rac)-4-(6,7-Dimethoxy-1,2,3,4-tetrahydroisoquinolin-1-yl)-benzene-1,2-diol |
| | 11F-CC7 | (rac)-4-(6,7-Dimethoxy-1,2,3,4-tetrahydroisoquinolin-1-yl)-phenol |
| | 11F-CC8 | (rac)-1-(3,4-Dichloro-phenyl)-6,7-dimethoxy-1,2,3,4-tetrahydro-isoquinoline |
| | 11F-CC9 | (rac)-3-(6,7-Dimethoxy-2-methyl-1,2,3,4-tetrahydro-isoquinolin-1-yl)-phenol |
| Structure XVII | 11F-CC10 | (rac)-1-Benzo[1,3]dioxol-5-yl-6,7-dimethoxy-2-ethyl-1,2,3,4-tetrahydro-isoquinoline |
| | 11F-CC11 | (rac)-1-Benzo[1,3]dioxol-5-yl-6,7-dimethoxy-2-propyl-1,2,3,4-tetrahydro-isoquinoline |
| | 11F-CC12 | (rac)-1-(3,4-Dihydroxy-phenyl)-1,2,3,4-tetrahydro-isoquinoline-6,7-diol |

TABLE 2-continued

11F-522 Series Compounds

| Structure | Code name | Chemical name |
|---|---|---|
| | 11F-CC13 | (rac)-1-Benzo[1,3]dioxol-5-yl-6,7-dimethoxy-2-acetyl-)-1,2,3,4-tetrahydro-isoquinoline |
| | 11F-CC14 | (rac)-1-(3,4-Dichloro-phenyl)-6,7-dimethoxy-2-methyl-1,2,3,4-tetrahydro-isoquinoline |
| | 11F-CC15 | (rac)-4-(6,7-Dimethoxy-2-methyl-1,2,3,4-tetrahydro-isoquinoline-1-yl)-phenol |
| | 11F-CC16 | (rac)-1-(benzo[d][1,3]dioxol-5-yl)-1,2,3,4-tetrahydroisoquinoline-6,7-diol |
| | 11F-CC17 | (rac)-1-Cyclohexyl-6,7-dimethoxy-1,2,3,4-tetrahydro-isoquinoline |
| | 11F-CC18 | (rac)-4-(6,7-Dimethoxy-2-methyl-1,2,3,4-tetrahydro-isoquinoline-1-yl)-benzene-1,2-diol |
| | 11F-CC19 | (rac)-1-Benzo[1,3]dioxol-5-yl-6,7-dimethoxy-2-allyl-1,2,3,4-tetrahydro-isoquinoline |
| | 11F-CC20 | (rac)-1-Benzo[1,3]dioxol-5-yl-6,7-dimethoxy-2-benzyl-1,2,3,4-tetrahydro-isoquinoline |
| | 11F-CC21 | (rac)-1-Cyclohexyl-6,7-dimethoxy-2-methyl-1,2,3,4-tetrahydro-isoquinoline |

Synthesis of Analogues of 11F-522

The individual enantiomers of 11F-522 were synthesised by first generating the racemic tetrahydroisoquinoline precursor via a Pictet-Spengler reaction. The obtained material was split into two halves which were combined with one enantiomer of tartaric acid each. The resulting salts were recyrstallised twice and the tartaric acid remove by treatment with base yielding both enantiomers of the precursors of 11F-522. The intermediates were then methylated using an Eshweiler-Clark reaction yielding both enantiomers of 11F-522 (Scheme 9). The optical purity was determined by measuring the optical rotation of the compounds.

Scheme 9.

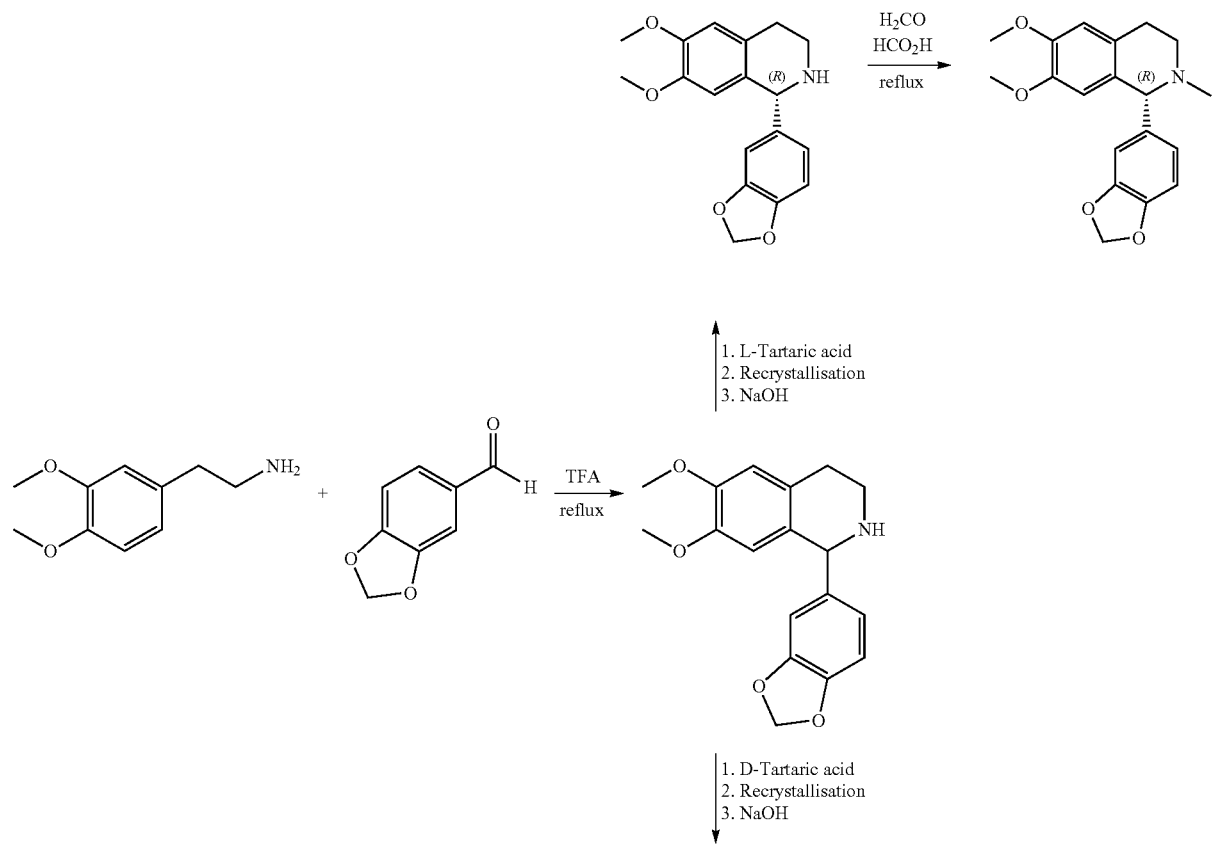

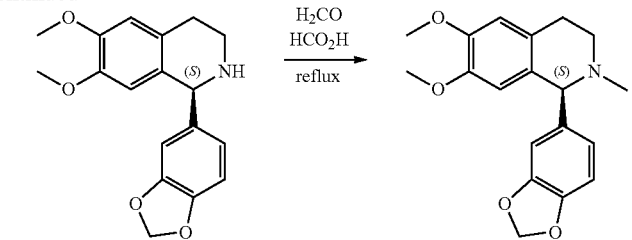
The analogues with different substituents on the nitrogen were all derived from the compound formed from the Pictet-Spengler reaction between 2-(3,4-dimethoxyphenyl)ethylamine and piperonal by either alkylating or acetylating followed by reduction of the amine (Scheme 10).
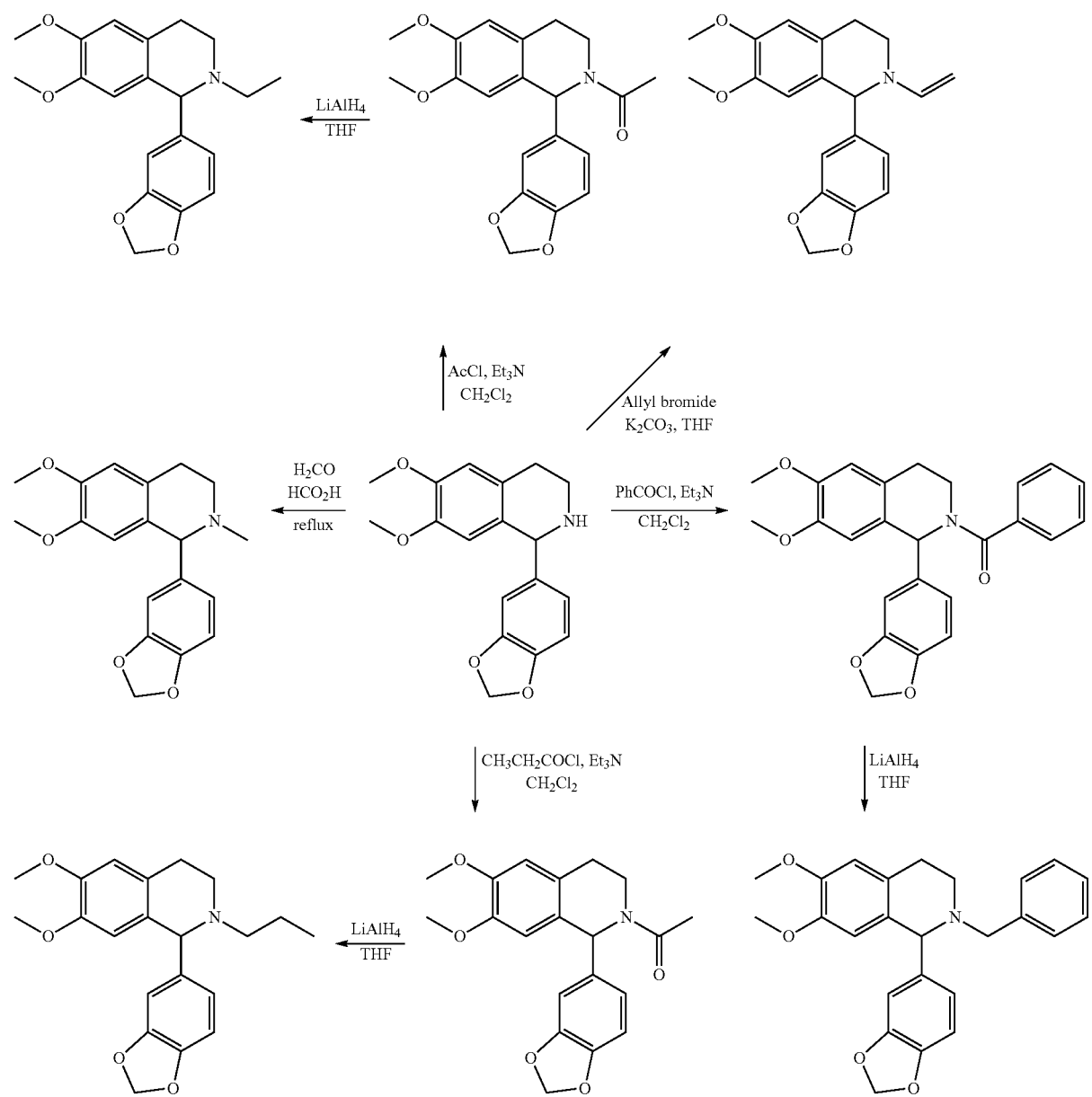

The analogues with varied substitutions on the aromatic ring as outlined below were all prepared via an initial Pictet-Spengler reaction between the appropriate amine and aldehyde followed by an Eschweiler-Clark methylation (Scheme 11).

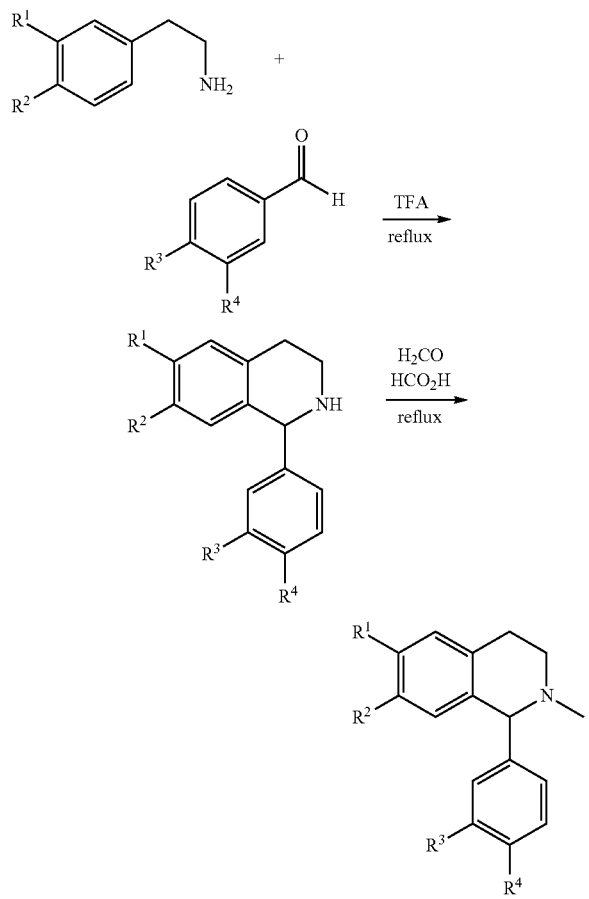

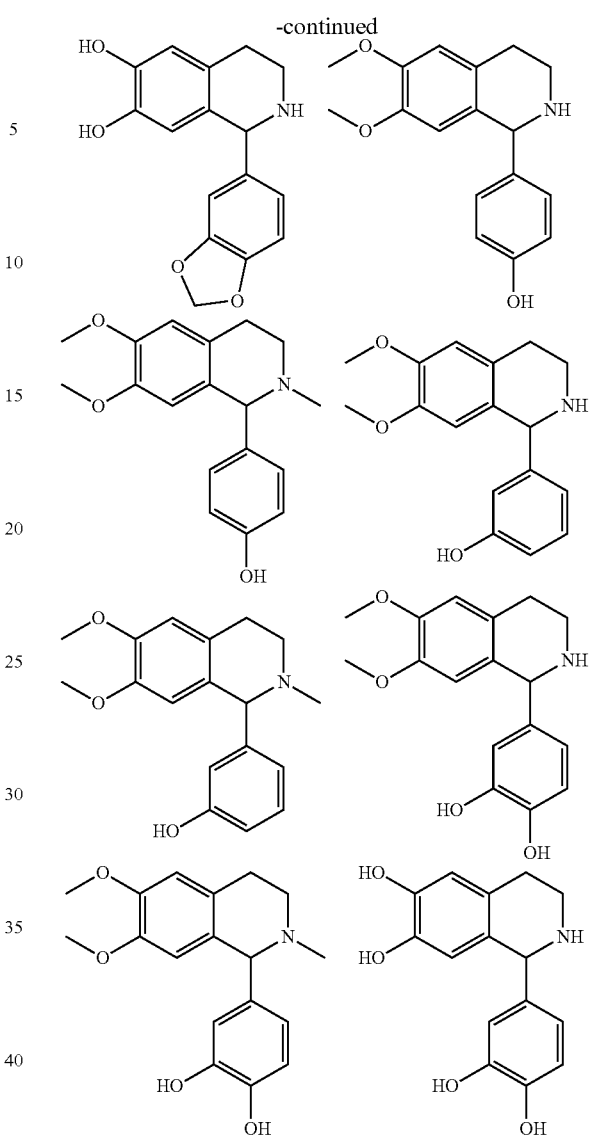

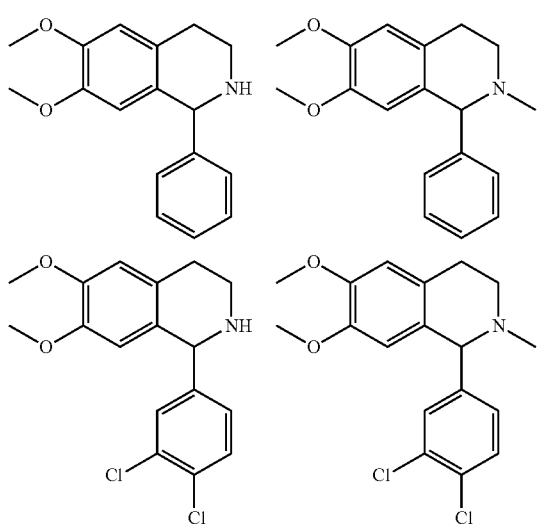

Compound 11F-708 has CAS#331978-30-4
Compound 11F-978 has CAS#1070341-31-9
Compound 11F-001 has CAS#447448-88-6

We have identified small molecule compounds that exhibit an anti-angiogenic effect, in vivo. The anti-angiogenic compounds may be used to treat inappropriate blood vessel formation (neovascularisation) such as the neovascularisation associated with debilitating forms of human blindness, including age-related macular degeneration (AMD) and diabetic retinopathy (DR). Additionally, these compounds may have therapeutic benefits in cancer, by cutting off the blood supply to tumours or by inhibiting the secretion of angiogenic and/or inflammatory factors from a tumour.

The compound may be administered to patients with diseases characterised by neovascularisation such as forms of progressive blindness that would benefit from stunting the growth of inappropriate new blood vessels, or cancer patients in which tumour growth can be halted by cutting off blood supply or by inhibiting the secretion of angiogenic and/or inflammatory factors from the tumour.

The anti-angiogenic compounds described herein have the potential to offer patients effective, easily administered, safe and cost-effective treatments to prevent vision loss and tumour growth The compounds described herein effectively inhibit new vessel growth. In the case of anti-angiogenic treatments for the eye, the compounds have the potential to be administered in the conventional manner as an injection or as eye drops as their small chemical size facilitates absorption from the cornea, unlike antibodies which require intravitreal injection. Similar-sized small molecules have been shown to exhibit anti-angiogenic efficacy in the eye upon topical administration (Doukas et al., 2008).

Topical administration of the compound, such as through eye drops, will eliminate the repeated injections that are required for the administration VEGF antibodies will reduce the safety risks associated with repeated intra vitreal injections. Furthermore, small molecule compounds will be cheaper to manufacture than antibodies and unlike antibodies, no potentially hazardous biological components are required to synthesise the compounds which will reduce the manufacturing costs and regulatory safety requirements.

We have used the zebrafish model as an in vivo screen of chemical compounds as the small size and transparency of the zebra fish enables high-content screens in multi-well plate formats (MacRae and Peterson, 2003; Pichler et al., 2003; Peterson et al., 2004; den Hertog, 2005; Zon and Peterson, 2005). Furthermore, many drugs have been shown to have comparable actions in humans and zebrafish including aspirin, warfarin, L-NAME, carbachol and diazepam (Goldsmith, 2004). To identify anti-angiogenic compounds we used a transgenic line of zebrafish that expresses a fluorescent reporter (EGFP) specifically in vasculature (Tg(fli1:efgp)). This line was obtained from the Zebrafish International Resource Center. Our assay involved screening the effect of compounds on the development of blood vessels in zebrafish. Specifically, we looked at the integrity of vessels developing in the eye (hyaloid vessels attached to the lens) and in the trunk. From these screens we have identified compounds that exhibited reproducible anti-angiogenic activity in vivo. Our characterisation of compounds was based on significant inhibition of hyaloid vessel formation in terms of pattern or primary branch number.

The invention will be more clearly understood from the following examples thereof.

EXAMPLES

Compounds Tested

Figure 19:
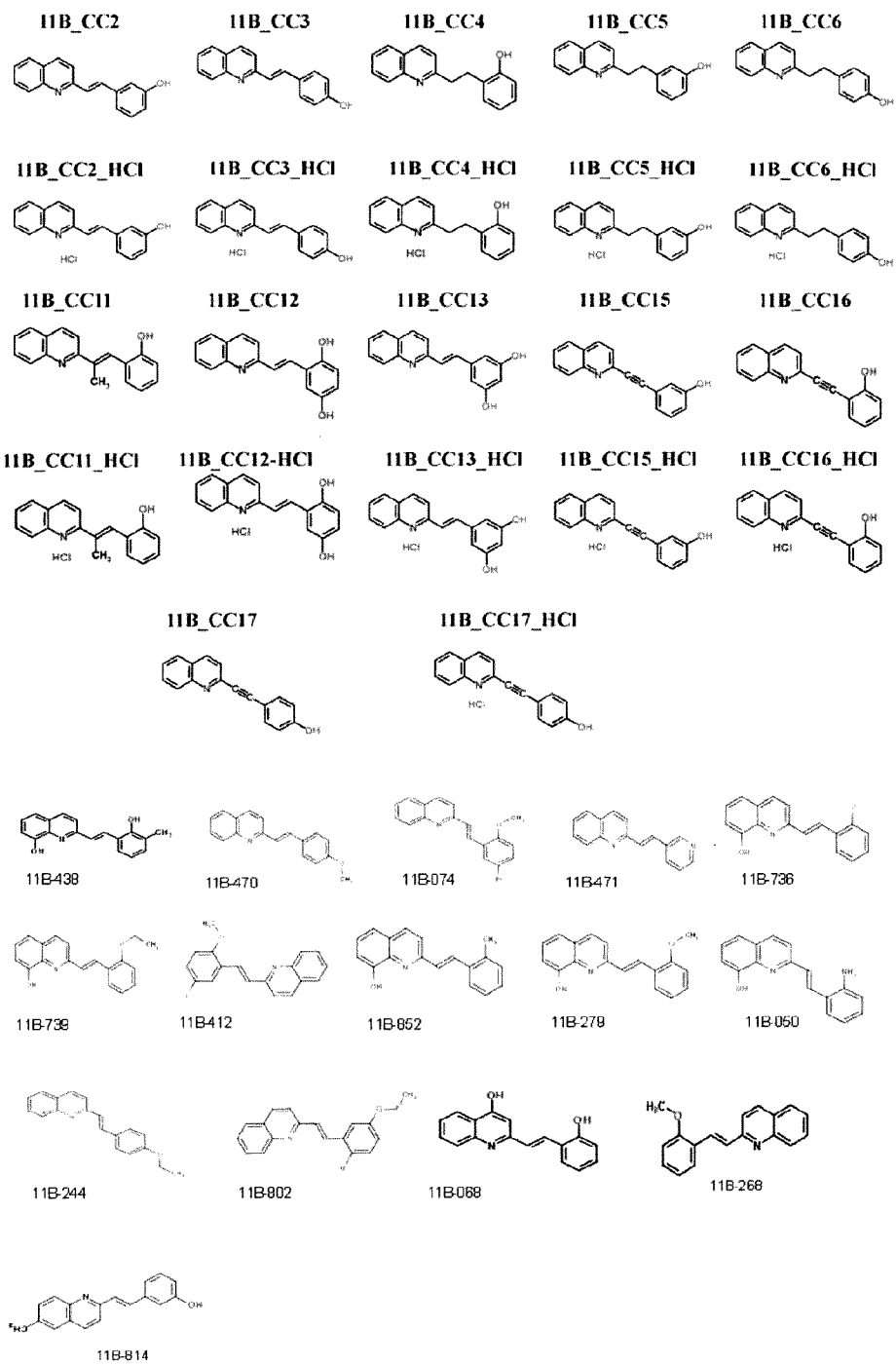
FIG. 19 shows the chemical structures of the 11B series of compounds.
Figure 20:
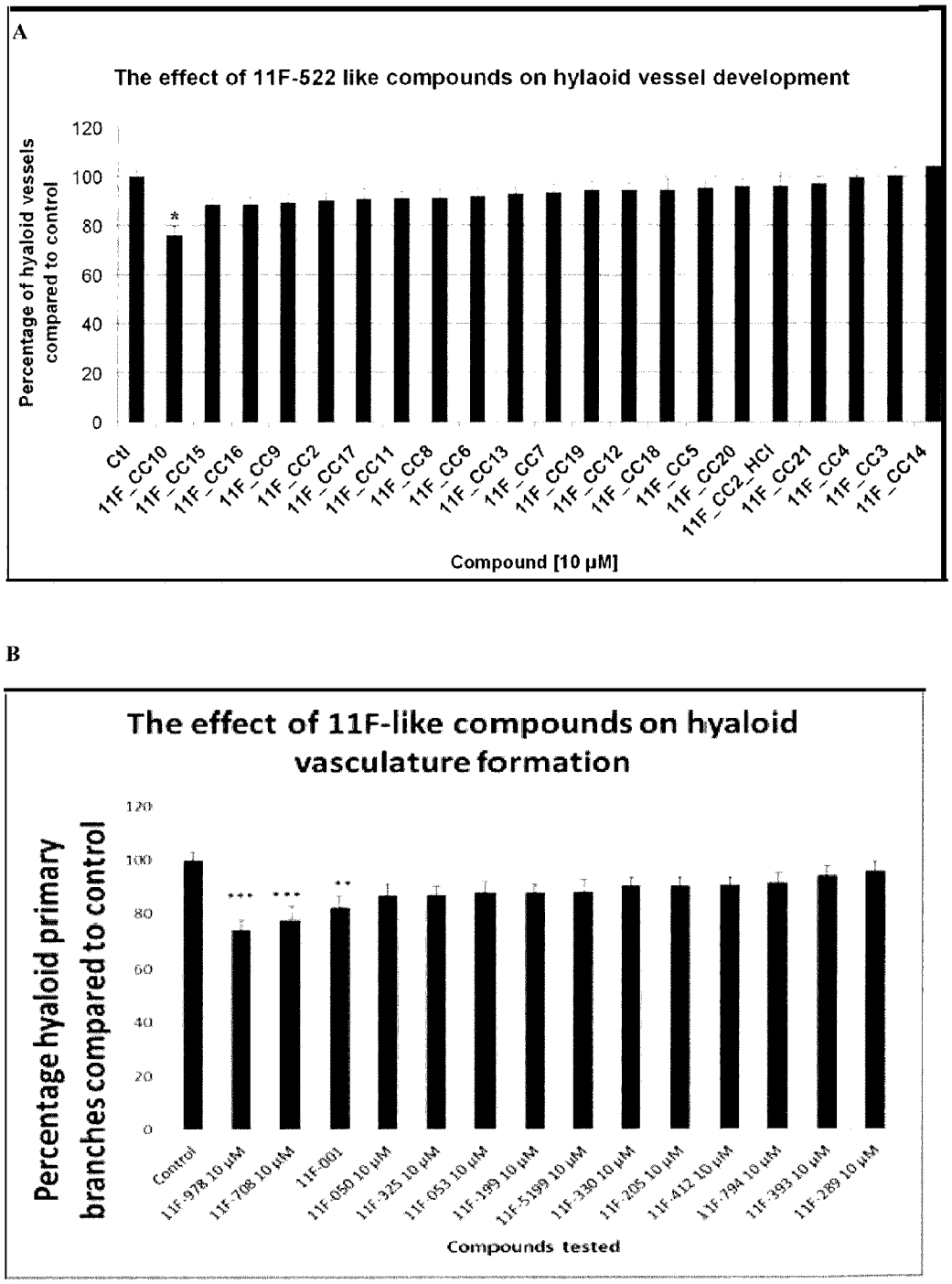
FIGS. 20 A and B are graphs showing the effect of 10 μM of 11F-522-series of compounds on inhibiting developmental angiogenesis of the hyaloid vasculature in the zebrafish eye. n≥10 for all samples * p-value ≤0.05, *** p-value ≤0.001.
Figure 21:
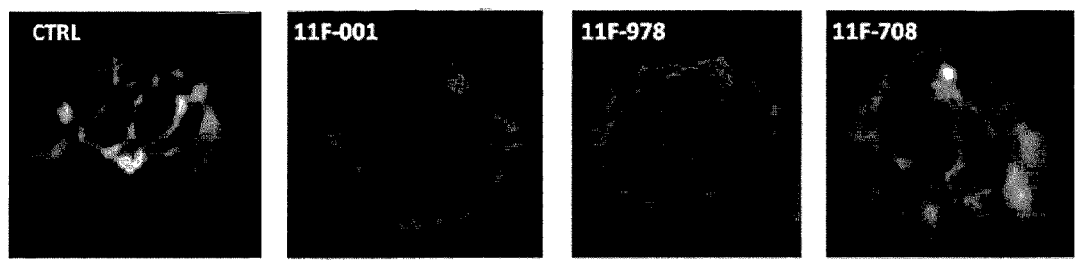
FIG. 21 shows representative epi-fluorescent images of the hyaloid vessels on dissected zebrafish lenses, depicting the patterns of hyaloid vasculature observed in zebrafish larvae treated with 10 μM of control, 11F-001, 11F-978 and 11F-708 compounds.
Figure 23:
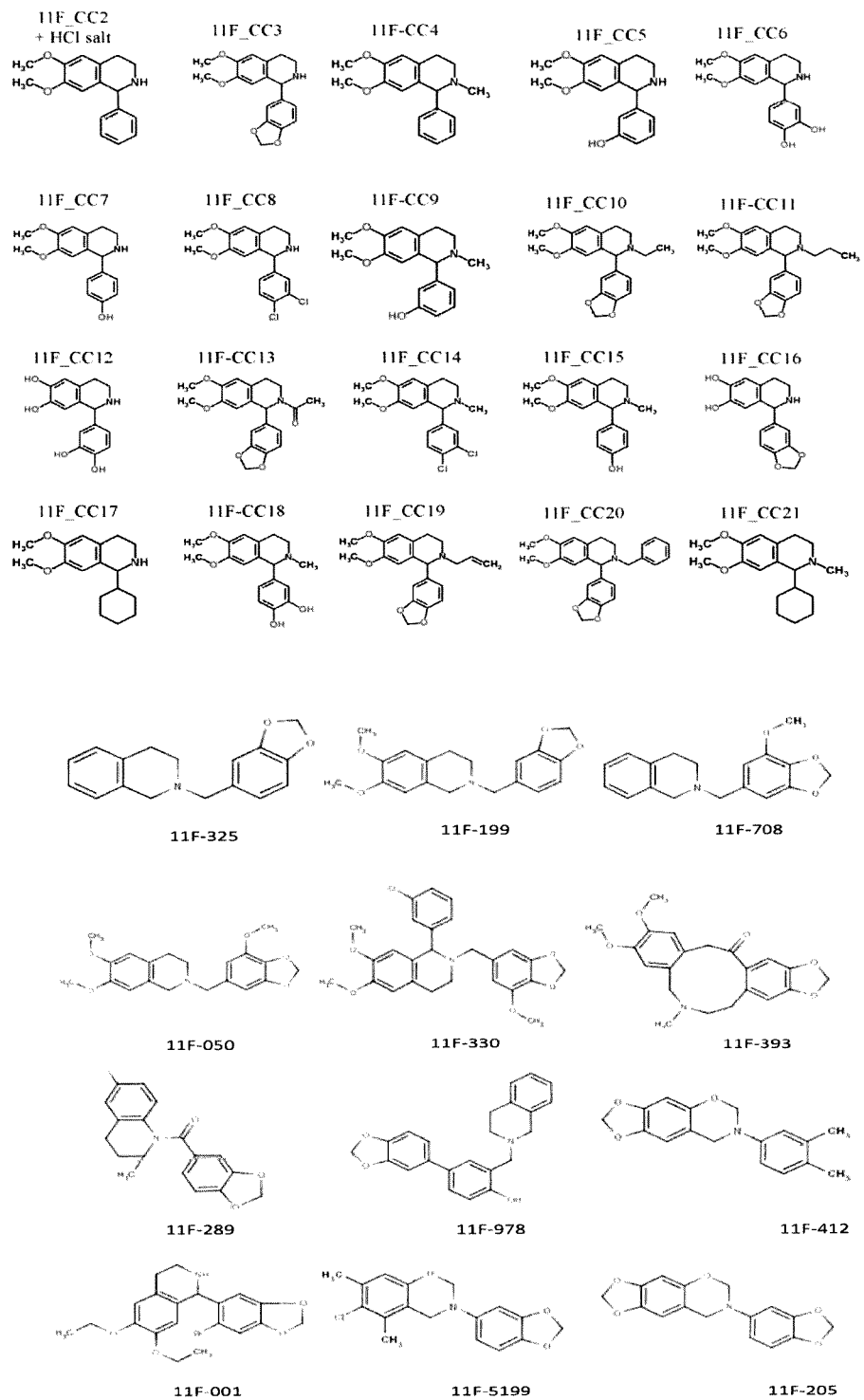
FIG. 23 shows the chemical structures of the 11F-522 series of compounds.
Figure 24:
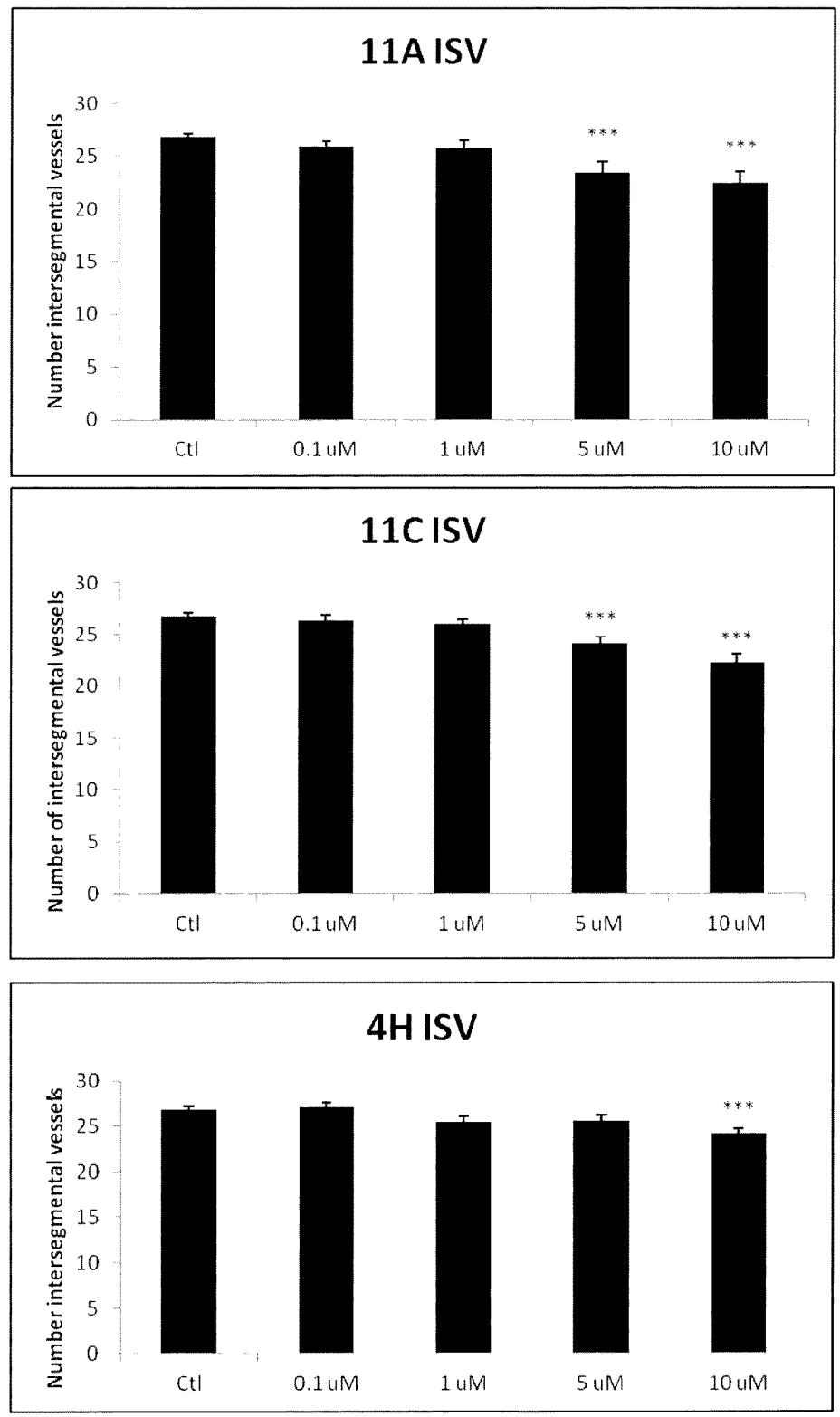
FIGS. 24 A, B and C are graphs showing the dose-dependent effect of compounds 4H, 11A and 11C on inhibiting developmental angiogenesis of the intersegmental vasculature in zebrafish. 10 μM of 4H, 5 and 10 μM of 11A and 5 and 10 μM of 11C results in a significant inhibition of the number of intersegmental vessels that develop. *** p-value ≤0.001.
Figure 25:
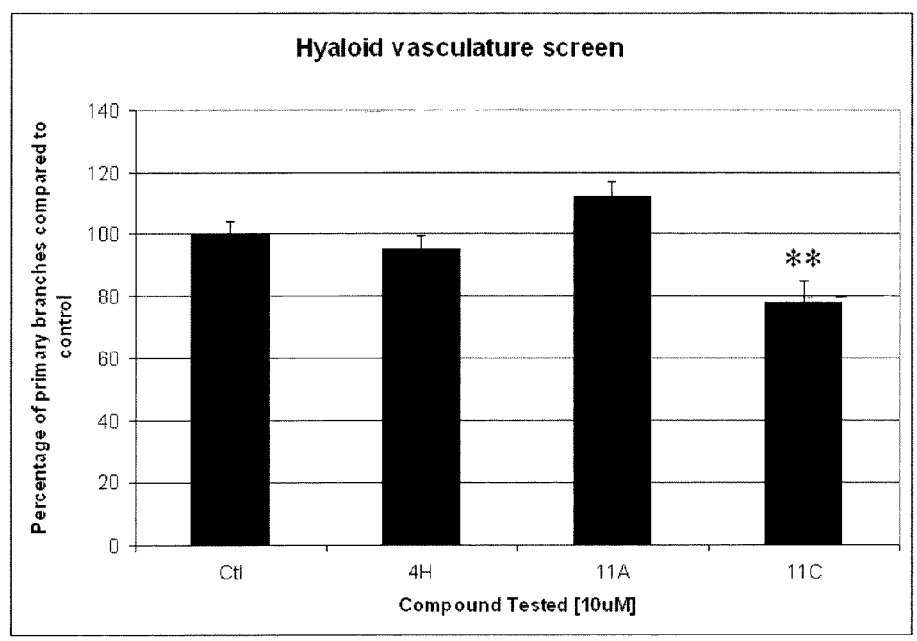
FIG. 25 is a graph showing the effect of compounds 4H, 11A and 11C in inhibiting developmental angiogenesis of the hyaloid vasculature in the zebrafish eye. 10 μM of 11C results in a significant inhibition of the number of primary hyaloid vessels that develop. n≥20 for all samples. ** p-value ≤0.01.
Figure 28:
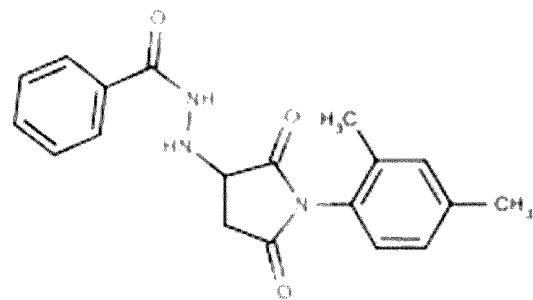
FIG. 28 shows the chemical structures and full chemical name of compounds 4H, 11A and 11C.
Figure 28:
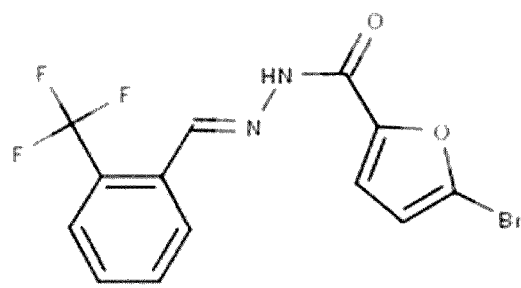
Figure 28:
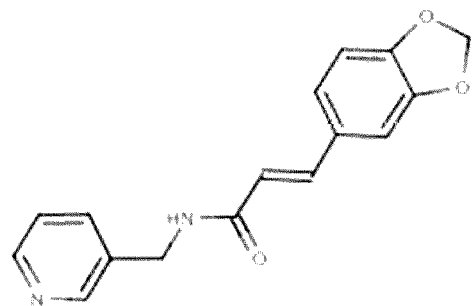
Figure 29:
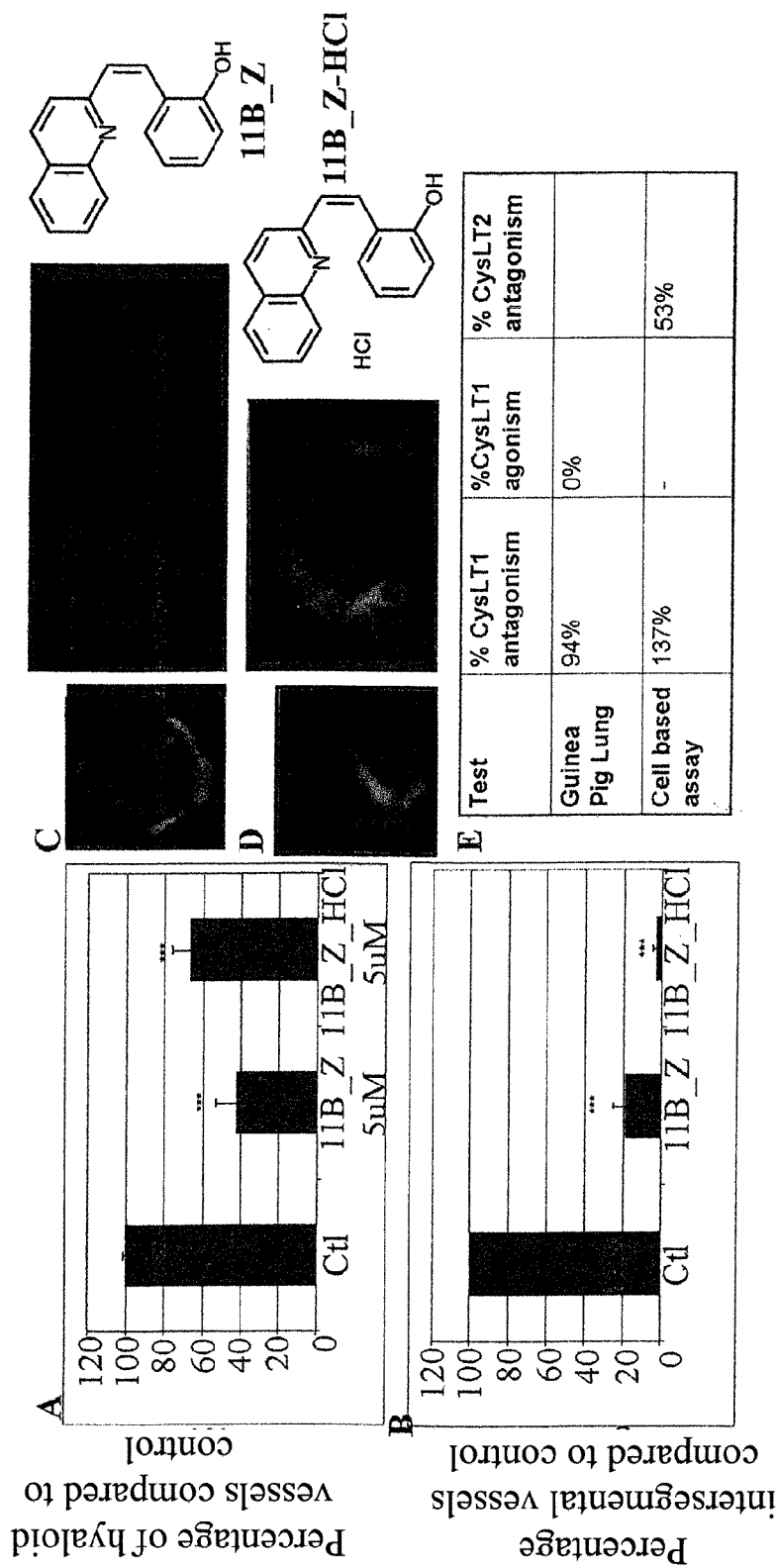
FIGS. 29 A, B, C, D and E shows graphs, representative images, chemical structures and tables relating to the Z-isomer.
Figure 30:
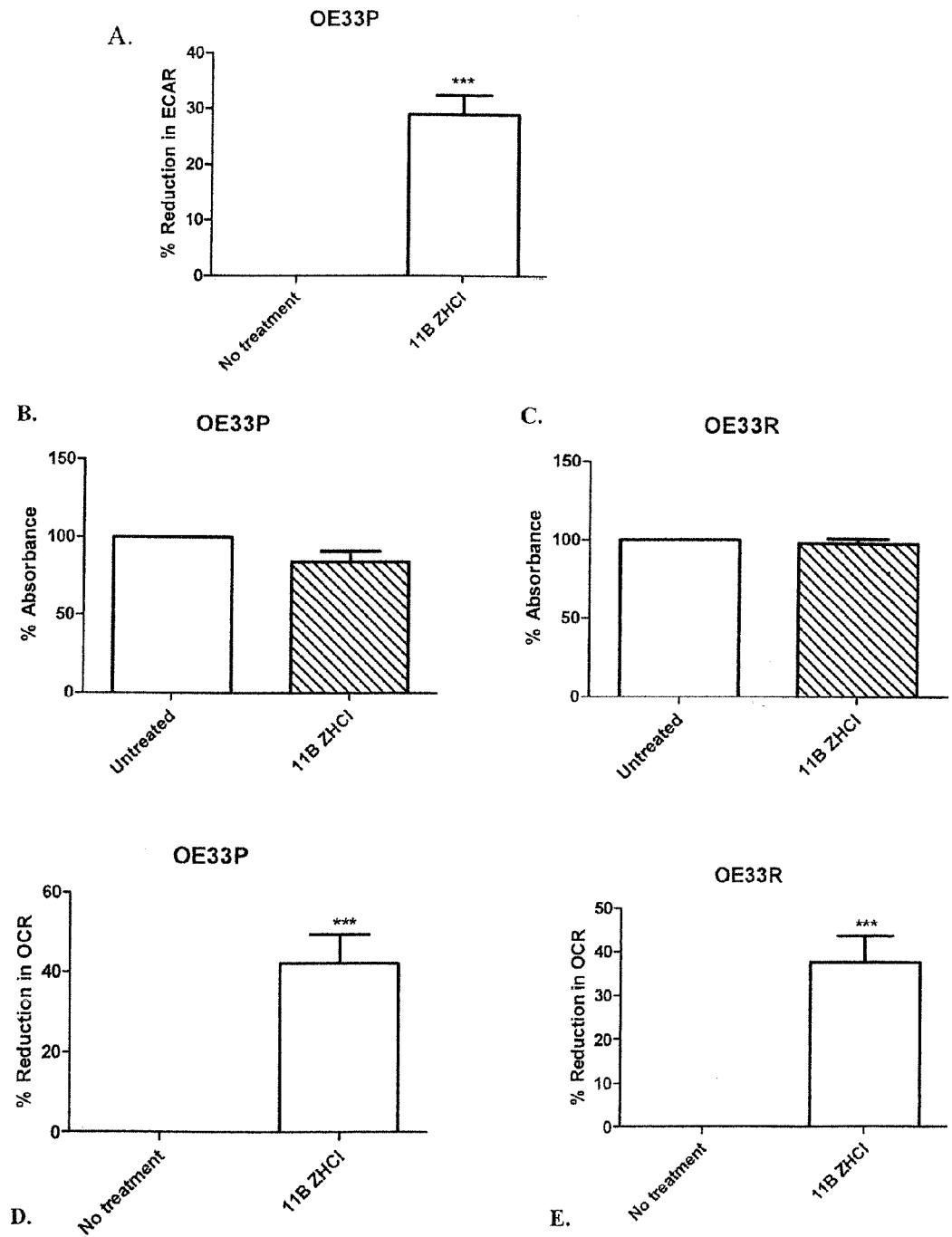
FIG. 30. A is a graph showing that compound 11B_Z_HCl significantly reduces extracellular acidification rate (ECAR), a measure of glycolysis, in OE33P radiosensitive oesophageal adenocarcinoma cells. OE33R were treated with 10 μM of 11B_Z_HCl for 24 hours, then EACR levels measured using Seahorse Bioscience metabolism technology. B and C are graphs showing that compound 11B_Z_HCl did not significantly reduce cell number, measured by % absorbance, in OE33P radiosensitive oesophageal adenocarcinoma cells (panel A) and OE33R radioresistant oesophageal adenocarcinoma cells (panel B). OE33P and OE33R were treated with 10 μM of 11B_Z_HCl for 24 hours, fixed with glutaraldehyde, stained with crystal violet, resuspended with TritonX-100 and absorbance measured at 590 nm. Panels D and E show that compound 11B_Z_HCl significantly reduces oxygen consumption rate (OCR), a measure of oxidative phosphorylation, in OE33P radiosensitive oesophageal adenocarcinoma cells (panel D) and in OE33R radioresistant oesophageal adenocarcinoma cells (panel E). OE33P and OE33R were treated with 10 μM of 11B_Z_HCl for 24 hours, the levels of OCR were measured using Seahorse Bioscience metabolism technology.
Figure 31:
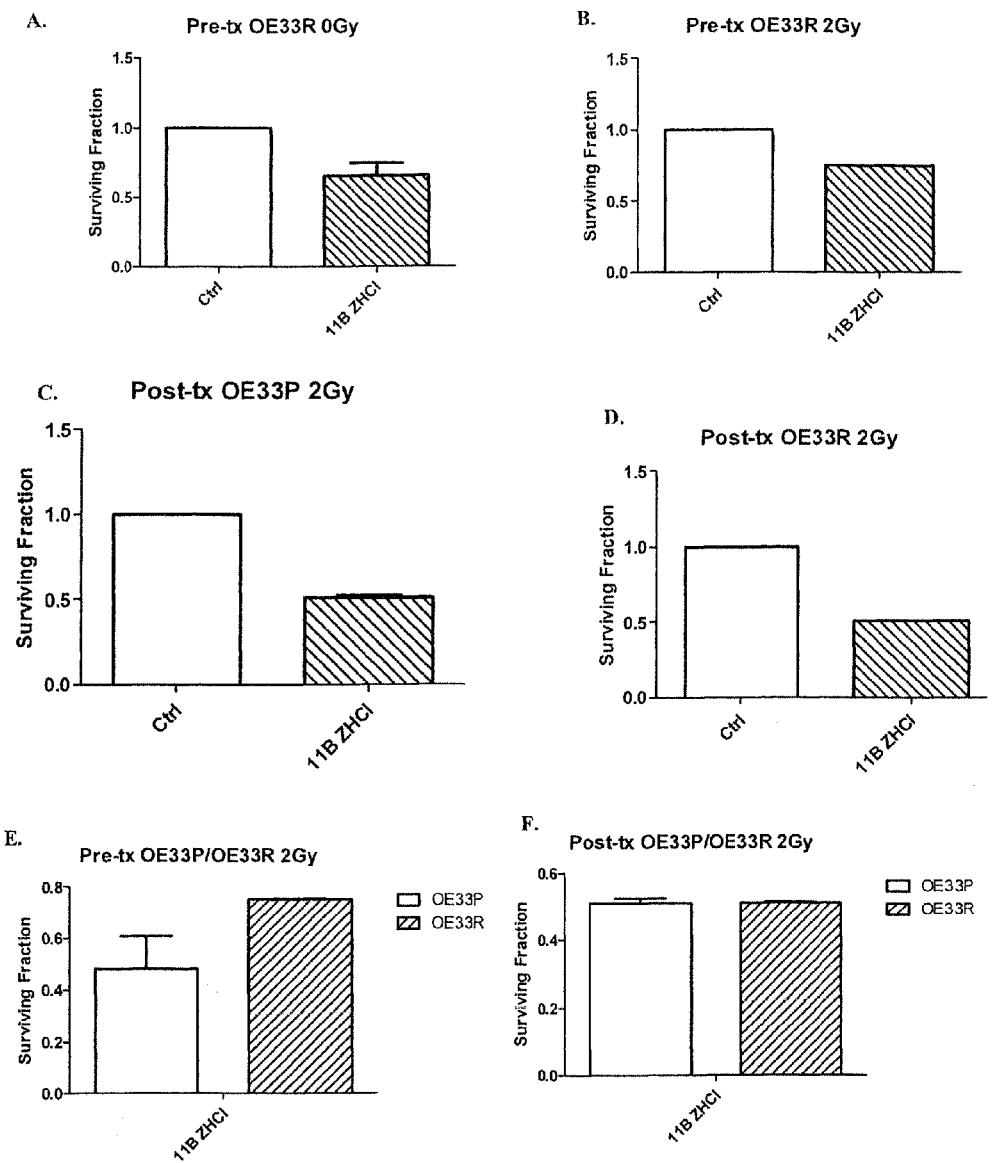
FIG. 31. A is a graph showing surviving fraction of OE33R radioresistant oesophageal adenocarcinoma cells. OE33R were treated with 10 μM of 11B HCl or 11B_CC11_HCl for 24 hours and left until control colonies were sufficiently large enough to score. B. is a graph showing surviving fraction of OE33R radioresistant oesophageal adenocarcinoma cells when cells were treated with 11B_Z_HCl prior to 2Gy irradiation. OE33R were treated with 10 μM of 11B HCl for 24 hours, irradiated and left until control colonies were sufficiently large. C. is a graph showing the surviving fraction of OE33P radiosensitive oesophageal adenocarcinoma cells when cells were treated with 11B_Z_HCl following 2Gy irradiation. OE33P were irradiated, treated with 10 μM of 11B HCl for 24 hours and left until control colonies were sufficiently large. D. is a graph showing surviving fraction of OE33R radioresistant oesophageal adenocarcinoma cells when cells were treated with 11B_Z_HCl following 2Gy irradiation. OE33R were irradiated, treated with 10 μM of 11B HCl for 24 hours and left until control colonies were sufficiently large. E. is a graph comparing surviving fraction of OE33P radiosensitive and OE33R radioresistant oesophageal adenocarcinoma cells when cells were treated with 11B_Z_HCl prior to 2Gy irradiation. OE33P were treated with 10 μM of 11B_Z_HCl for 24 hours, irradiated and left until control colonies were sufficiently large. F. is a graph comparing surviving fraction of OE33P radiosensitive and OE33R radioresistant oesophageal adenocarcinoma cells when cells were treated with 11B_Z_HCl following 2Gy irradiation. OE33P were irradiated, treated with 10 μM of 11B HCl or 11B_CC11_HCl for 24 hours and left until control colonies were sufficiently large.
Figure 32:
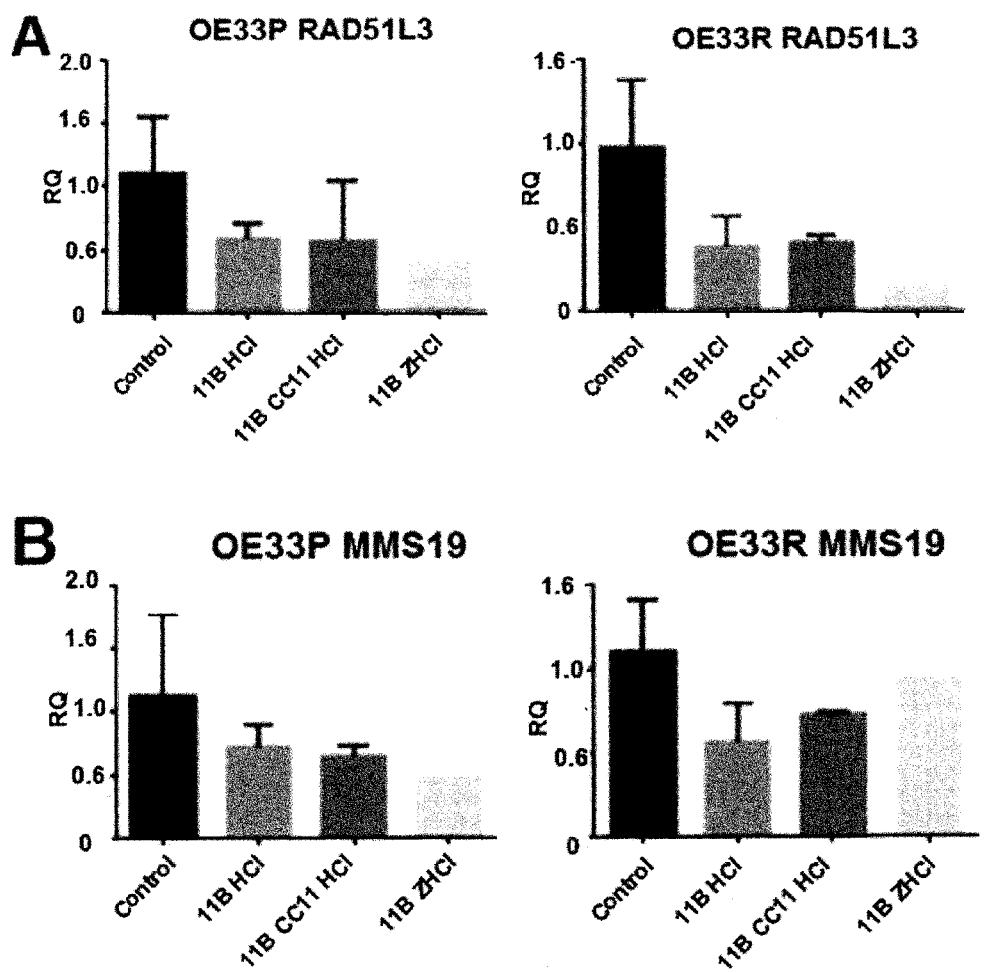
FIG. 32 is a graph showing reductions of RAD51L3, MMS19, SMUG1 and PARP1 in OE33P radiosenstive cells. OE33R radioresistant cells show reduction of RAD51L3, MMS19, PARP1 and MLH1.
Figure 32:
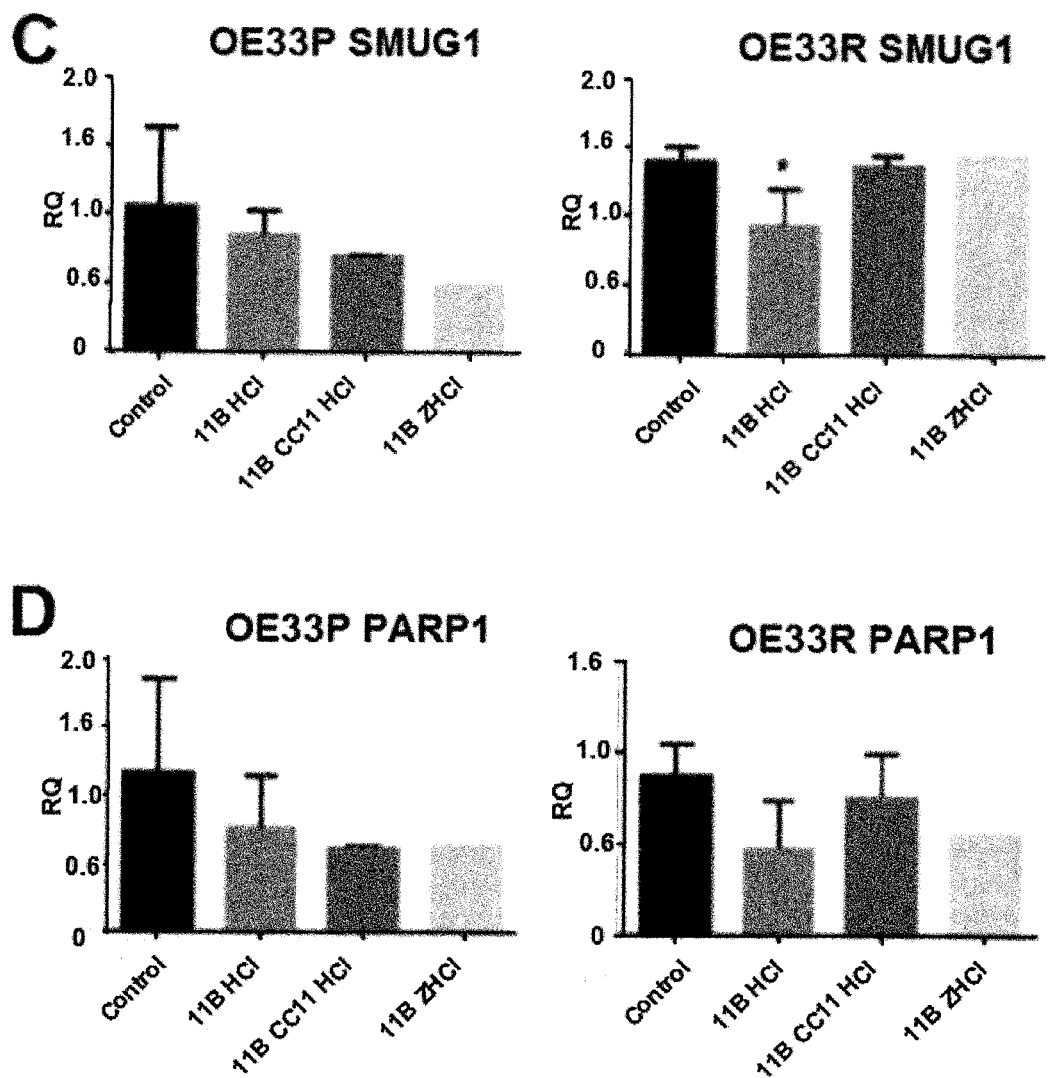
Figure 32:
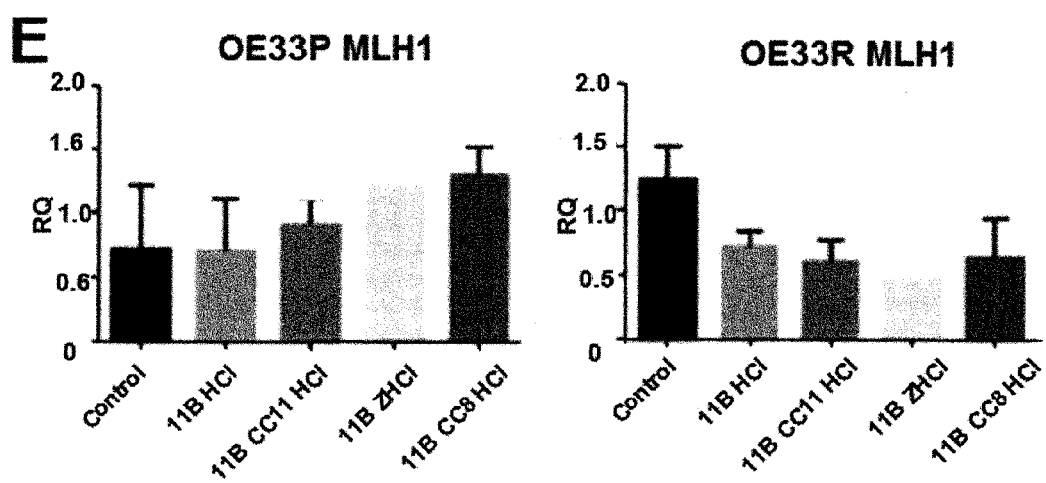

The following compounds were screened in the zebrafish model as described in Examples 1 and 2 below. The chemical structures of the 11B series of compounds are shown in FIGS. 19 and 29. The chemical structures of the 11F-522 series of compounds are shown in FIG. 23. The chemical structures of compounds 4H, 11A and 11C are shown in FIG. 28.

TABLE 1

| | 11B Series Compounds | |
|---|---|---|
| Structure | Code name | Chemical name |
| | 11B-068 | 2-[(E)-2-(2-Hydroxyphenyl)vinyl]-4-quinolinol |
| | 11B-244 | 2-[2-(4-ethoxyphenyl)vinyl]quinoline |
| | 11B-050 | 2-[2-(2-aminophenyl)vinyl]-8-quinolinol |
| Structure XII | 11B-736 | 2-[2-(2-chlorophenyl)vinyl]-8-quinolinol |
| Structure XIII | 11B-739 | 2-[2-(2-ethoxyphenyl)vinyl]-8-quinolinol |
| Structure X | 11B-470 | 2-[(E)-2-(2-Hydroxyphenyl)vinyl]-4-quinolinol |
| | 11B-852 | 2-[2-(2-methylphenyl)vinyl]-8-quinolinol |
| Structure IX | 11B-438 | 2-[(E)-2-(2-Hydroxy-3-methylphenyl)vinyl]-8-quinolinol |
| Structure VII | 11B-074 | 2-[2-(5-bromo-2-methoxyphenyl)vinyl]quinoline |
| | 11B-802 | 2-[2-(2-bromo-5-ethoxyphenyl)vinyl]quinoline |
| Structure XI | 11B-471 | 2-[2-(3-pyridinyl)vinyl]quinoline |
| Structure VIII | 11B-412 | 2-[2-(5-iodo-2-methoxyphenyl)vinyl]quinoline |
| | 11B-279 | 2-[2-(2-methoxyphenyl)vinyl]-8-quinolinol |
| Structure I | 11B-CC2 | 3-(2-Quinolin-2-yl-vinyl)-phenol |
| | 11B-CC2-HCl | 3-(2-Quinolin-2-yl-vinyl)-phenol HCl salt |
| | 11B-CC3 | 4-(2-Quinolin-2-yl-vinyl)-phenol |
| | 11B-CC3-HCl | 4-(2-Quinolin-2-yl-vinyl)-phenol HCl salt |
| Structure II | 11B-CC4 | 2-(2-Quinolin-2-yl-ethyl)-phenol |
| | 11B-CC4-HCl | 2-(2-Quinolin-2-yl-ethyl)-phenol HCl salt |
| Structure III | 11B-CC5 | 3-(2-Quinolin-2-yl-ethyl)-phenol |
| | 11B-CC5-HCl | 3-(2-Quinolin-2-yl-ethyl)-phenol HCl salt |
| | 11B-CC6 | 4-(2-Quinolin-2-yl-ethyl)-phenol |
| | 11B-CC6-HCl | 4-(2-Quinolin-2-yl-ethyl)-phenol HCl salt |
| Structure IV | 11B-CC11 | (E)-2-(2-Quinolin-2-yl-propenyl)-phenol |
| | 11B-CC11-HCl | (E)-2-(2-Quinolin-2-yl-propenyl)-phenol HCl salt |
| | 11B-CC12 | (E)-2-(2-Quinolin-2-yl-vinyl)- -benzene-1,4-diol |
| | 11B-CC12-HCl | (E)-2-(2-Quinolin-2-yl-vinyl)- -benzene- 1,4-diolHCl salt |
| | 11B-CC13 | (E)-2-(2-Quinolin-2-yl-vinyl)- -benzene-2,4-diol |
| | 11B-CC13-HCl | (E)-2-(2-Quinolin-2-yl-vinyl)-benzene-2,4-diolHCl salt |
| Structure V | 11B-CC15 | 3-Quinolin-2-yl-ylethynyl-phenol |
| | 11B-CC15-HCl | 3-Quinolin-2-yl-ylethynyl-phenol HCl salt |
| Structure VI | 11B-CC16 | 2-Quinolin-2-yl-ylethynyl-phenol |
| | 11B-CC16-HCl | 2-Quinolin-2-yl-ylethynyl-phenol HCl salt |
| | 11B-268 | 2-(2-(2-Methoxyphenyl)vinyl)quinoline |
| | 11B-814 | 3-[(E)-2-(6-Methyl-2-quinolinyl)vinyl]phenol |
| | 11B_Z | (Z)-2-(2-(Quinolin-2-yl)vinyl) phenol |
| | 11B_Z_HCl | (Z)-2-(2-(Quinolin-2-yl)vinyl) phenol HCl salt |

TABLE 2

11F-522 Series Compounds

| Structure | Code name | Chemical name |
|---|---|---|
| | 11F-325 | 2-(1,3benzodioxol-5-ylmethyl)-1,2,3,4-tetrahydroisoquinoline |
| | 11F-199 | 2-(1,3benzodioxol-5-ylmethyl)-6,7-dimethoxy-1,2,3,4-tetrahydroisoquinoline |
| Structure XVI | 11F-708 | 2-[(7-methoxy-1,3-benzodioxol-5-yl)methyl]-1,2,3,4-tetrahydroisoquinoline |
| | 11F-050 | 6,7-dimethoxy-2-[(7-methoxy-1,3-benzodioxol-5-yl)methyl]-1,2,3,4-tetrahydroisoquinoline |
| | 11F-330 | 1-(3-chlorophenyl)-6,7-dimethoxy-2-[(7-methoxy-1,3-benzodioxol-5-yl)methyl]-1,2,3,4-tetrahydroisoquinoline |
| | 11F-393 | 2,3-dimethoxy-6-methyl-5,7,8,15-tetrahydrobenzo[c][1,3]benzodioxolo[5,6-g]azecin-14(6H)-one |
| | 11F-289 | 1-(1,3-benzodioxol-5-ylcarbonyl)-6-fluoro-2-methyl-1,2,3,4-tetrahydroquinoline |
| Structure XV | 11F-978 | 4-(1,3-benzodioxol-5-yl)-2-(3,4-dihydro-2(1H)-isoquinolinylmethyl)phenol |
| | 11F-412 | 7-(3,4-dimethylphenyl)-7,8-dihydro-6H-[1,3]dioxolo[4,5-g][1,3]benzoxazine |
| Structure XIV | 11F-001 | 1-(6-bromo-1,3-benzodioxol-5-yl)-6,7-diethoxy-1,2,3,4-tetrahydroisoquinoline |
| | 11F-5199 | 3-(1,3-benzodioxol-5-yl)-6-chloro-5,7-dimethyl-3,4-dihydro-2H-1,3-benzoxazine |
| | 11F-205 | 7-(1,3-benzodioxol-5-yl)-7,8-dihydro-6H-[1,3]dioxolo[4,5-g][1,3]-benzoxazine |
| | 11F-053 | 1-(1,3-benzodioxol-5-yl)-6,7-diethoxy-3,4-dihydro-1H-isochromene |
| | 11F-794 | 1-(1,3-benzodioxol-5-ylmethyl)-4-(3,4,5-trimethoxybenzyl)piperazine |
| | 11F-CC2 | (rac)-6,7-Dimethoxy-1-phenyl-1,2,3,4-tetrahydro-isoquinoline |
| | 11F-CC2-HCl | (rac)-6,7-Dimethoxy-1-phenyl-1,2,3,4-tetrahydro-isoquinoline HCl salt |
| | 11F-CC3 | (rac)-1-Benzo[1,3]dioxol-5-yl-6,7-dimethoxy-1,2,3,4-tetrahydro-isoquinoline |
| | 11F-CC4 | (rac)-6,7-Dimethoxy-2-methyl-1-phenyl-1,2,3,4-tetrahydro-isoquinoline |
| | 11F-CC5 | (rac)-3-(6,7-Dimethoxy-1,2,3,4-tetrahydroisoquinolin-1-yl)-phenol |
| | 11F-CC6 | (rac)-4-(6,7-Dimethoxy-1,2,3,4-tetrahydroisoquinolin-1-yl)-benzene-1,2-diol |
| | 11F-CC7 | (rac)-4-(6,7-Dimethoxy-1,2,3,4-tetrahydroisoquinolin-1-yl)-phenol |
| | 11F-CC8 | (rac)-1-(3,4-Dichloro-phenyl)-6,7-dimethoxy-1,2,3,4-tetrahydro-isoquinoline |
| | 11F-CC9 | (rac)-3-(6,7-Dimethoxy-2-methyl-1,2,3,4-tetrahydro-isoquinolin-1-yl)-phenol |
| Structure XVII | 11F-CC10 | (rac)-1-Benzo[1,3]dioxol-5-yl-6,7-dimethoxy-2-ethyl-1,2,3,4-tetrahydro-isoquinoline |
| | 11F-CC11 | (rac)-1-Benzo[1,3]dioxol-5-yl-6,7-dimethoxy-2-propyl-1,2,3,4-tetrahydro-isoquinoline |
| | 11F-CC12 | (rac)-1-(3,4-Dihydroxy-phenyl)-1,2,3,4-tetrahydro-isoquinoline-6,7-diol |
| | 11F-CC13 | (rac)-1-Benzo[1,3]dioxol-5-yl-6,7-dimethoxy-2-acetyl-)-1,2,3,4-tetrahydro-isoquinoline |
| | 11F-CC14 | (rac)-1-(3,4-Dichloro-phenyl)-6,7-dimethoxy-2-methyl-1,2,3,4-tetrahydro-isoquinoline |
| | 11F-CC15 | (rac)-4-(6,7-Dimethoxy-2-methyl-1,2,3,4-tetrahydro-isoquinoline-1-yl)-phenol |
| | 11F-CC16 | (rac)-1-(benzo[d][1,3]dioxol-5-yl)-1,2,3,4-tetrahydroisoquinoline-6,7-diol |
| | 11F-CC17 | (rac)-1-Cyclohexyl-6,7-dimethoxy-1,2,3,4-tetrahydro-isoquinoline |
| | 11F-CC18 | (rac)-4-(6,7-Dimethoxy-2-methyl-1,2,3,4-tetrahydro-isoquinoline-1-yl)-benzene-1,2-diol |
| | 11F-CC19 | (rac)-1-Benzo[1,3]dioxol-5-yl-6,7-dimethoxy-2-allyl-1,2,3,4-tetrahydro-isoquinoline |
| | 11F-CC20 | (rac)-1-Benzo[1,3]dioxol-5-yl-6,7-dimethoxy-2-benzyl-1,2,3,4-tetrahydro-isoquinoline |
| | 11F-CC21 | (rac)-1-Cyclohexyl-6,7-dimethoxy-2-methyl-1,2,3,4-tetrahydro-isoquinoline |

TABLE 3

Compounds 4H, 11A and 11C

| Structure | Code name | Chemical name |
| --- | --- | --- |
| Structure XVIII | 4H | N'-[1-(2,4-dimethylphenyl)-2,5-dioxo-3-pyrrolidinyl]benzohydrazide |
| Structure XIX | 11A | (5-bromo-N'-[2-(trifluromethyl)benzylidene]-2-furohydrazide) |
| Structure XX | 11C | (3-(1,3-benzodioxol-5-yl-N-(3-pyridinylmethyl)acrylamide) |

Example 1

Quantification of Primary Hyaloid Vasculature Branch Number

All experiments were carried out under ethical approval granted by the UCD animal research ethics committee. Tail: EGFP) zebrafish were maintained according to standard procedures on a 14 hr light/10 hr dark cycle at 28° C. Embryos were obtained by natural spawning and developmental stages established by time and morphological criteria. At 24 hours post fertilisation (hpf), 5 embryos per well were placed in 400 µl of Embryo Medium/0.1% DMSO and incubated with compound (typically, 10 µM or 5 µM) at 28° C. on a 14 h light/10 h dark cycle. Larvae were euthanised, and fixed in 4% PFA at 4° C. overnight before analysis.

Prior to analysis of the intraocular vasculature, the control and treated larvae were observed under an Olympus SZX16 stereo zoom microscope and screened for general malformations. Overall patterning of the vasculature (fin, gut and intersegmental vessels) was examined for abnormalities. Right lenses were dissected from the larvae and transferred to depression slides for observation under epi-fluorescence in the Olympus SZX16. Patterning of the hyaloid vessels on the treated larval lenses was compared to DMSO controls and the archetypal pattern previously described (Alvarez et al., 2007; Alvarez et al., 2009). The number of primary vessels radiating from the back of the lens (3-4 main branches at 5 dpf in controls and previously described), was counted and the average number was graphed for each drug. Compounds 11B-739, 11B-438, 11B-074, 11B-471, 11B-268, 11B-814, 11B_CC2, 11B_CC2_HCl, 11B_CC4_HCl, 11B_CC5, 11B_CC5_HCl, 11B_CC11, 11B_CC11_HCl, 11B_CC16, 11B_CC16_HCl, 11F-001, 11F978, 11F-708, 11F-CC10 and 11C, 11B_Z and 11B_Z_HCl inhibit developmental angiogenesis of the zebrafish hyaloid vasculature in a statistically significant manner (FIG. 1, FIG. 16, FIG. 18, FIG. 20 and FIG. 21, FIG. 22, FIG. 25, and FIG. 29).

Example 2

Quantification of Intersegmental Vessel Number

At 6 hours post fertilisation, 5 embryos per well were placed in 400 µL of embryo medium/0.1% DMSO and incubated with 10 µM compound at 28° C. on a 14 h light/10 h dark cycle. Larvae were manually dechorionated, euthanised, and fixed in 4% PFA at 4° C. overnight before analysis. The larvae were then washed with PBS and transferred to depression slides for observation under epi-fluorescence in an Olympus SZX16 fluorescent microscope. The number of intersegmental vessels was counted and the average number was graphed for each drug. Compounds 11B-470, 11B-438, 11B-736, 11B-471, 11B-412, 11B_CC2, 11B_CC2_HCl, 11B_CC3_HCl, 11B_CC4_HCl, 11B_CC5_HCl, 11B_CC11, 11B_CC11-HCl, 11B_CC12, 11B_CC15, 11B_CC15_HCl, 11B_CC16, 11B_CC16_HCl, 11A, 11C and, 4H, 11B_Z and 11B_Z_HCl inhibit developmental angiogenesis of zebrafish intersegmental vessels in a statistically significant manner (FIG. 1, FIG. 17 and FIG. 18, FIG. 24 and FIG. 29).

Example 3

Analysis of Ocular Neovascularisation in Mouse Oxygen-Induced Retinopathy Model Postnatal day (P) 7 C57BL/6J mice together with their dams were treated in 75% oxygen (hyperoxia) for 5 days causing regression of retinal blood vessels. They were returned to normoxia (relative hypoxia) on P12, causing rapid regrowth of the retinal blood vessels. 5 µM 11B_CC11_HCl, 5 µM 11B_CC16_HCl, 5 µM pazopanib or 2.5 mg/ml avastin was injected intravitreally on P13. The mice were culled on P17, eyes fixed in 4% paraformaldehyde at 4° C. overnight, flat mounted and retinas stained for isolectin (red, stains vasculature). (A) The flat-mounted retinas were imaged and avascular region quantified and expressed as a percentage of the whole retina (B) Graph showing that 11B_CC11_HCl and 11B_CC16_HCl inhibit neovascularisation compared to P17 control.

Example 4

Quantification of Human OE33P and OE33R Cell Number after 24 Hours Drug Treatment OE33P radio-sensitive and OE33R radio-resistant oesophageal adenocarcinoma cells were used to test the effects of the compounds 11B HCl, 11B CC11 HCl, 11B CC16 HCl, 11B 471 and 11B 268 on cell number. Cells were maintained in RPMI media supplemented with 10% foetal calf serum, penicillin (100 U/ml) and streptomycin (100 µg/ml). A total of 11,000 or 13,000 cells, in 100 µl media, were seeded per well in 24 well plates and left to incubate for 24 hours, with an additional 150 µl media added after 5 hours. The media was replaced with solutions containing µM of 11B HCl, 11B CC11 HCl, 11B CC16 HCl, 11B 471, 11B 268 or fresh media as a control. Each drug had 6 replicates. After 24 hours of treatment, the cells were fixed with 1% glutaraldehyde for 15 minutes and then stained with crystal violet for 30 minutes. The plates were blotted and dried overnight. The cells were resuspended with 1% TritonX-100 and shaken for 15 minutes. The absorbance was read on a spectrophotometer at 590 nm.

Example 5

Quantification of Glycolysis in Human OE33P and OE33R Cells In Vitro

OE33P radio-sensitive and OE33R radio-resistant oesophageal adenocarcinoma cells were used to test the effects of compounds 11B HCl, 11B CC11 HCl, 11B CC16 HCl, 11B 471 and 11B 268 on glycolysis. Cells were maintained in RPMI media supplemented with 10% foetal calf serum, penicillin (100 U/ml) and streptomycin (100 µg/ml). A total of 11,000 or 13,000 cells, in 100 µl media, were seeded per well in 24 well plates and left to incubate for 24 hours, with an additional 150 µl media added after 5 hours. The media was replaced with solutions containing µM of 11B HCl, 11B CC11 HCl, 11B CC16 HCl, 11B 471, 11B 268 or fresh media as a control. Each drug had 6 replicates. After 24 hours of treatment, media was replaced with modified DMEM supplemented with 0.5 mM glucose. Rates of glycolysis were determined using Seahorse Biosciences metabolism technology. The media was disposed and the cells washed with PBS. The cells were fixed with 1% glutaraldehyde for 15 minutes and then stained with crystal violet for 30 minutes. The plates were blotted and dried overnight. The cells were resuspended with 1% TritonX-100 and shaken for 15 minutes. The absorbance was read on a spectrophotometer at 590 nm. Rates of glycolysis were then normalised to cell number.

Example 6

Quantification of the Surviving Fraction of Radio-Sensitive and Radio-Resistant Human OE33P and OE33R Cells In Vitro OE33P radio-sensitive and OE33R radio-resistant oesophageal adenocarcinoma cells were used to test the effects of the compounds 11B HCl and 11B CC11 HCl on cell survival. Cells were maintained in RPMI media supplemented with 10% foetal calf serum, penicillin (100 U/ml) and streptomycin (100 µg/ml). Cells were seeded in 6 well plates and left to incubate for 24 hours. The media was replaced with solutions containing 10 µM of 11B HCl, 11B CC11 HCl or fresh media as a control. After 24 hours of treatment, media was replaced. When control colonies had grown sufficiently large, the media was disposed and the cells washed with PBS. The cells were fixed with methanol and stained with crystal violet. The surviving fraction, the ability of the cells to form colonies was then determined.

Example 7

Quantification of Surviving Fraction of Irradiated Human OE33P and OE33R Cells In Vitro when Cells were Treated Prior to Irradiation OE33P radio-sensitive and OE33R radio-resistant oesophageal adenocarcinoma cells were used to test the effects of the compounds 11B HCl and 11B CC11 HCl on cell survival. Cells were maintained in RPMI media supplemented with 10% foetal calf serum, penicillin (100 U/ml) and streptomycin (100 µg/ml). Cells were seeded in 6 well plates and left to incubate for 24 hours. The media was replaced with solutions containing 10 µM of 11B HCl, 11B CC11 HCl or fresh media as a control. After 24 hours of treatment, media was replaced and cells were subjected to 2Gy radiation. When control colonies had grown sufficiently large, the media was disposed and the cells washed with PBS. The cells were fixed with methanol and stained with crystal violet. Surviving fraction, the ability of the cells to form colonies was then determined.

Example 8

Quantification of Surviving Fraction of Irradiated Human OE33P and OE33R Cells when Cells were Treated with 11B HCl and 11B CC11 HCl Following Irradiation OE33P radio-sensitive and OE33R radio-resistant oesophageal adenocarcinoma cells were used to test the effects of the compounds 11B HCl and 11B CC11 HCl on cell survival. Cells were maintained in RPMI media supplemented with 10% foetal calf serum, penicillin (100 U/ml) and streptomycin (100 µg/ml). Cells were seeded in 6 well plates and left to incubate for 24 hours. The cells were subjected to 2Gy irradiation and the media was replaced with solutions containing 10 µM of 11B HCl, 11B CC11 HCl or fresh media as a control. After 24 hours of treatment, media was replaced. When control colonies had grown sufficiently large, the media was disposed and the cells washed with PBS. The cells were fixed with methanol and stained with crystal violet. Surviving fraction, the ability of the cells to form colonies was then determined.

Example 9

Quantification of Oxidative Phosphorylation in Human OE33P and OE33R Cells In Vitro OE33P radiosensitive and OE33R radio-resistant oesophageal adenocarcinoma cells were used to test the effects of the compounds 11B HCl, 11B CC11 HCl, 11B CC16 HCl, 11B 471 and 11B 268 on oxidative phosphorylation. Cells were maintained in RPMI media supplemented with 10% foetal calf serum, penicillin (100 U/ml) and streptomycin (100 µg/ml). A total of 11,000-13,000 cells, in 100 µl media, were seeded per well in 24 well plates and left to incubate for 24 hours, with an additional 150 µl media added after 5 hours. The media was replaced with solutions containing 10 µM of 11B HCl, 11B CC11 HCl, 11B CC16 HCl, 11B 471, 11B 268 or fresh media as a control. Each drug had 6 replicates. After 24 hours of treatment, media was replaced with modified DMEM supplemented with 0.5 mM glucose. Rates of oxidative phosphorylation were determined using Seahorse Biosciences metabolism technology. The media was disposed and the cells washed with PBS. The cells were fixed with 1% glutaraldehyde for 15 minutes and then stained with crystal violet for 30 minutes. The plates were blotted and dried overnight. The cells were resuspended with 1% TritonX-100 and shaken for 15 minutes. The absorbance was read on a spectrophotometer at 595 nm. Rates of oxidative phosphorylation were then normalised to cell number.

Example 10

Quantification of Target Inhibition

Target profiling using Cerep and Eurofins/Panlabs profiling screens was undertaken using 11B_CC11_HCl and 11B_CC16_HCl in order to investigate the mechanism of action. For the guinea pig lung strip assay, a lung strip obtained from Duncan Hartley derived male or female guinea pigs weighing 325±25 g and sacrificed by $CO_2$ overexposure was used. The tissue was placed under 2 g tension in a 10 mL bath containing Krebs solution pH 7.4 at 37° C. Test substance (30 µM)-induced isometrically recorded contraction by 50 percent or more within 5 min, relative to control 3 nM leukotriene D4 response, indicates possible cysteinyl-leukotriene LT1 receptor agonist activity. At a test substance concentration where no significant agonist activity is seen, ability to reduce the leukotriene D4-induced contractile response by 50 percent or more indicates cysteinyl-leukotriene CysLT1 antagonist activity. 30 µM 11B_CC16_HCl did not induce contraction itself, exhibiting no agonist activity. 30 µM 11B_CC16_HCl reduced the leukotriene D4-induced contractile response by 100%, indicating CysLT1 antagonist activity. To measure inhibition of cysteinyl leukotriene 1 (CysLT1 [LTD4]) and cysteinyl leukotriene 2 (CysLT2 [LTC4]) receptor activity, calcium mobilisation was measured using Fluor-3-loaded CHO cells (for cysLT1 assays) or HEK-293 cells (for CysLT2 assays) which stably express either the CysLT1 or CysLT2 receptors. Cells were seeded on FLIPR microtiter plates (Molecular Devices, Sunnyvale, Calif.; Schroeder and Neagle,) and grown to confluence. Subsequently the growth medium was removed and Fluo-3 AM fluorescent indictor dye diluted in Hanks' balanced salt was added to each well and incubated for 1 hour at 37° C. FluoR-3 Am was then removed and cells were washed three times. Baseline fluorescence was determined by measuring the level of fluorescence every 1 second for the first minute and every 3 seconds for the second minute. After ten seconds a range of doses of LTD4 (for CysLT1) or LTC4 (for CysLT2) was added and the $EC_{50}$ of each agonist was determined. For antagonism quantification, 30 µM of 11B_CC11_HCl or 11B_CC16_HCl was added to each well and the ability for each compound to inhibit the CysLT1 & CysLT2 response to LTD4 (0.1 nM) or LTC4 (30 nM) was measured. For CysLT1 antagonism, both 11B_CC11_HCl and 11B_CC16_HCl inhibited calcium mobilisation to below baseline levels (137%). For CysLT2 antagonism, 11B_CC11_HCl inhibited calcium mobilisation by 41% and 11B_CC16_HCl inhibited calcium mobilisation by 48%.

Example 11

Figure 22A:
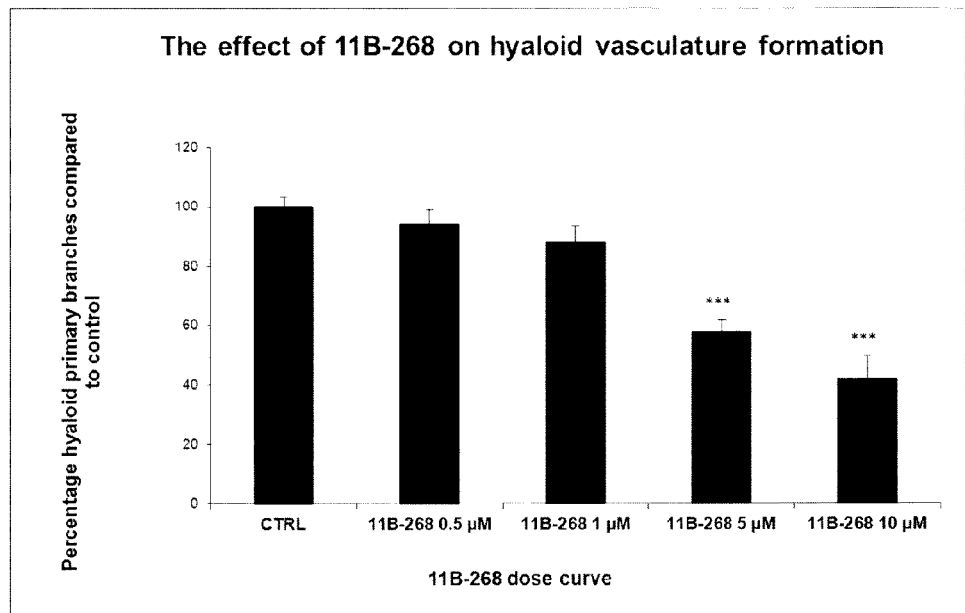
FIGS. 22 A and B show the dose-dependent effect of compounds 11B_CC4_HCl, 11B_CC5_HCl, 11B_CC11_HCl, 11B_CC16, 11B_CC16_HCl, 11B-268 and 11B-814 in inhibiting the development of hyaloid vessels and/or intersegmental vessels. * p-value ≤0.05,  p-value ≤0.01, * p-value ≤0.001.
Figure 22A:
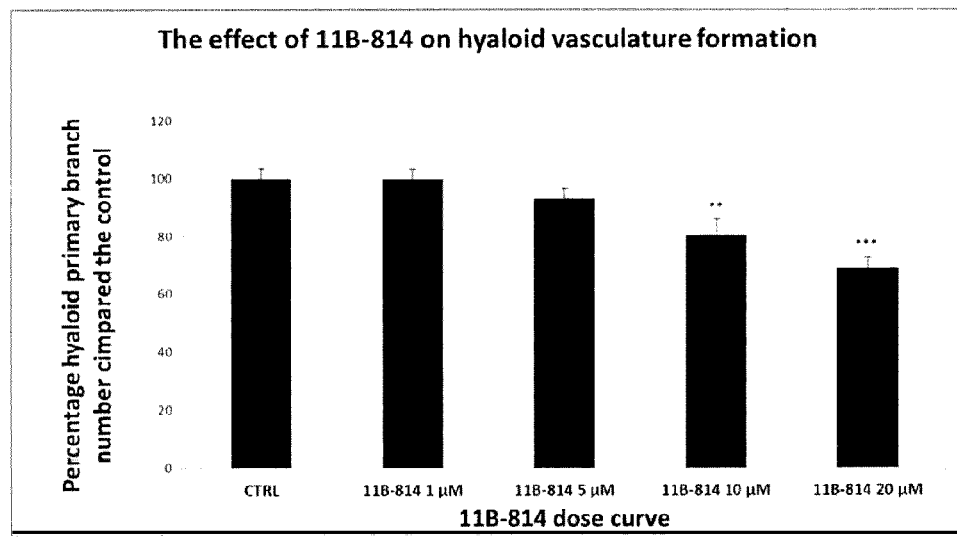
Figure 22B:
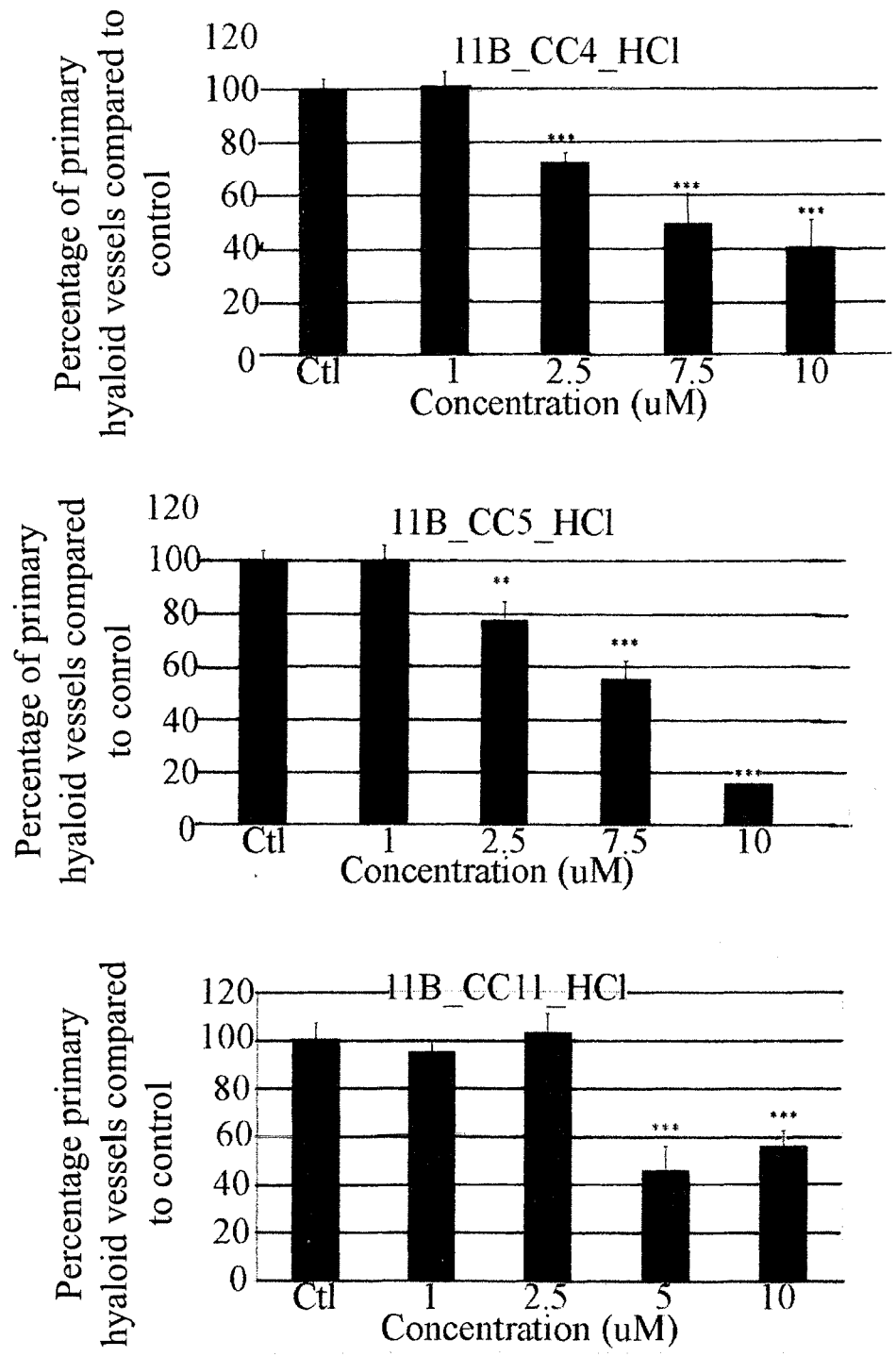
Figure 22B:
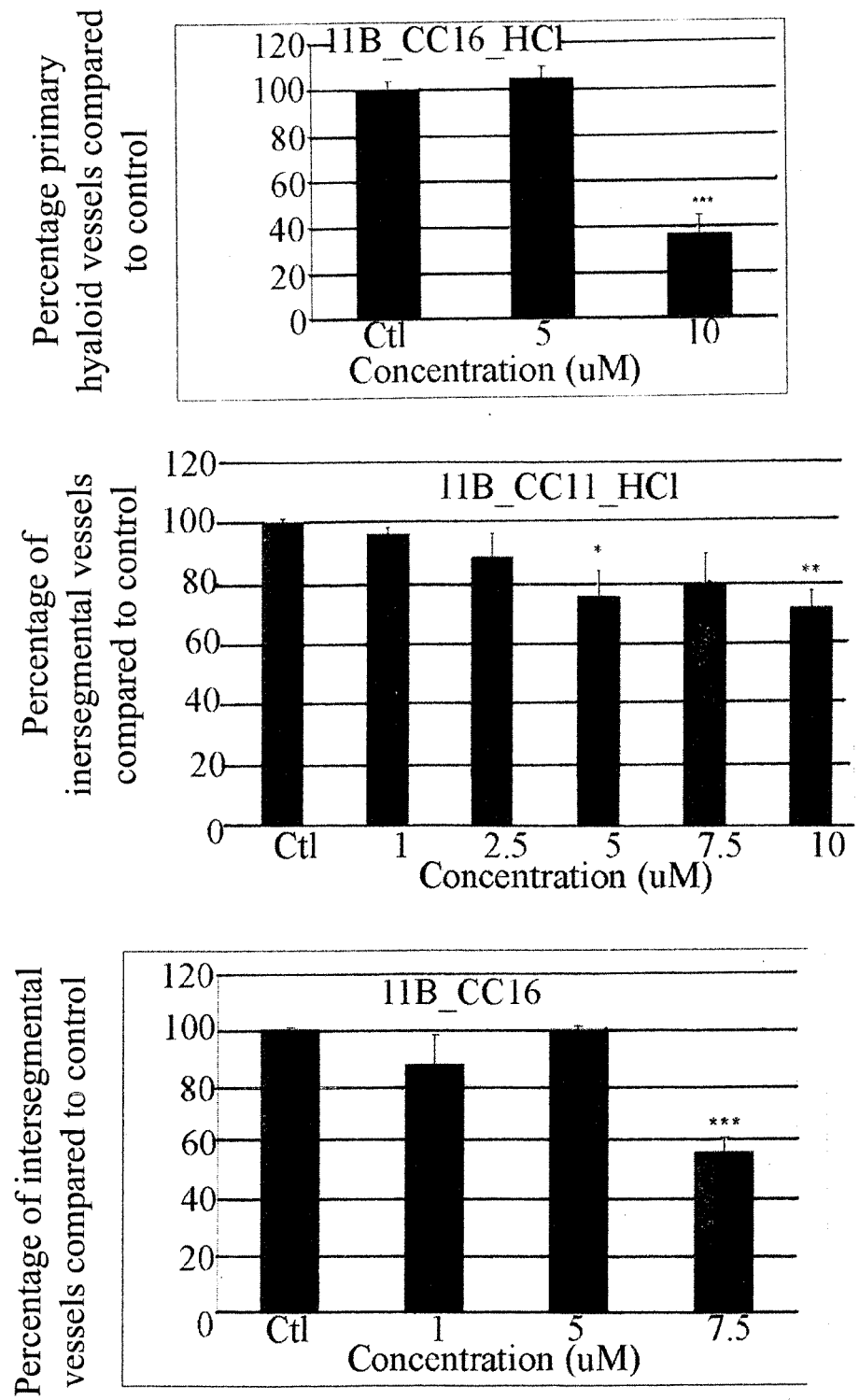

Quantification Dose-Dependence in the Primary Hyaloid Vasculature Branch Number Assay All experiments were carried out under ethical approval granted by the UCD animal research ethics committee. Tail: EGFP zebrafish were maintained according to standard procedures on a 14 hr light/10 hr dark cycle at 28° C. Embryos were obtained by natural spawning and developmental stages established by time and morphological criteria. At 24 hours post fertilisation (hpf), 5 embryos per well were placed in 400 µl of Embryo Medium/0.1% DMSO and incubated with decreasing doses of active compounds (20 µM, 10 µM, 7.5 µM, 5 µM, 2.5 µM, 1 µM and/or 0.5 µM) at 28° C. on a 14 h light/10 h dark cycle. Larvae were euthanised, and fixed in 4% PFA at 4° C. overnight before analysis. Lenses were dissected from the larvae and transferred to depression slides for observation under epi-fluorescence in the Olympus SZX16. Patterning of the hyaloid vessels on the treated larval lenses was compared to DMSO controls and the archetypal pattern previously described (Alvarez et al., 2007; Alvarez et al., 2009). The number of primary vessels radiating from the back of the lens (3-4 main branches at 5 dpf in controls and previously described), was counted and the average number was graphed for each drug. Compounds 11B_CC4_HCl, 11B_CC5_HCl, 11B_CC11_HCl, 11B_CC16_HCl, 11B-268 and 11B-471 inhibit developmental angiogenesis of zebrafish hyaloid vasculature in a dose-dependent statistically significant manner (FIGS. 22A and 22B).

Example 12

Quantification of Dose-Dependence in the Intersegmental Vessel Assay

At 6 hours post fertilisation, 5 embryos per well were placed in 400 µL of Embryo Medium/0.1% DMSO and incubated with decreasing doses of active compound (10 µM, 7.5 µM, 5 µM and/or 1 µM) at 28° C. on a 14 h light/10 h dark cycle. Larvae were manually dechorionated, euthanised, and fixed in 4% PFA at 4° C. overnight before analysis. The larvae were then washed with PBS and transferred to depression slides for observation under epi-fluorescence in an Olympus SZX16 fluorescent microscope. The number of intersegmental vessels was counted and the average number was graphed for each drug. Compounds 11B_CC11_HCl and 11B_CC16_HCl, inhibit developmental angiogenesis of zebrafish intersegmental vessels in a dose-dependent statistically significant manner (FIG. 22B).

Example 13

Figure 26:
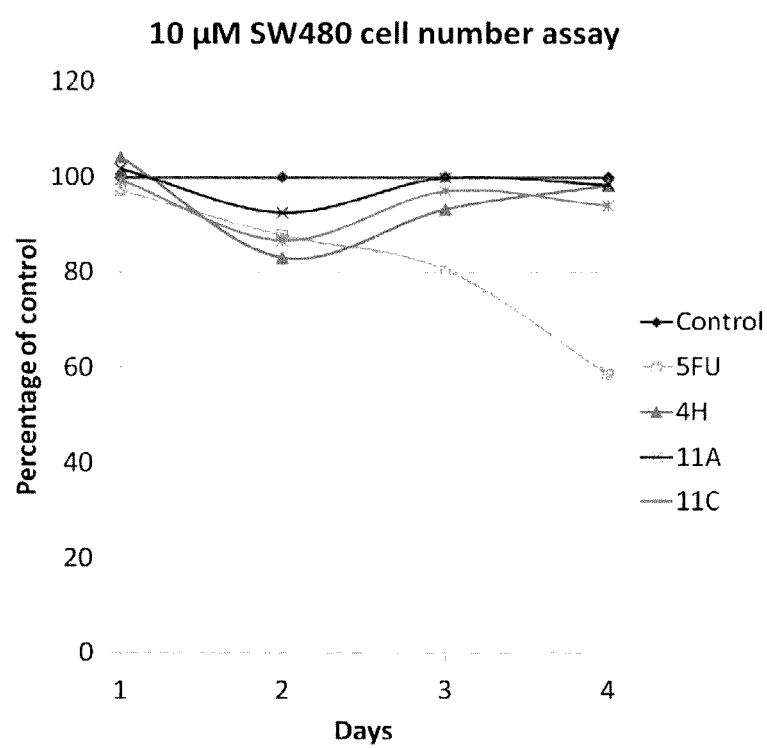
FIG. 26 is a graph showing that compounds 4H, 11A and 11C have no significant effect on the proliferation of human SW480 colorectal cancer cells. Cultures of SW480 were treated with 10 μM of 4H, 11A and 11C or 10 μM of 5-fluorouracil (5-FU) as a positive control. 5-fluorouracil significantly reduced cell number to 60% of the control by 96 hours. 4H, 11A or 11C did not significantly reduce cell number compared to control by 96 hours.

4H, 11a and 11C do not Significantly Reduce the Proliferation of Human SW480 Cells In Vitro SW480 (commercially available colorectal cancer cell line) were used to test the effects of the compounds 4H, 11A and 11C on cell toxicity. Cells were maintained in RPMI media supplemented with 10% foetal calf serum, penicillin (100 U/ml), streptomycin (100 µg/ml) and amphotericin B (4 µg/ml). A total of 5,000 cells were seeded per well in 96 well plates and left to incubate for 24 hours. The cells were washed in PBS and the media was replaced with solutions containing 10 µM of 5-fluorouracil (5FU), 4H, 11A or 11C. Each drug had 10 replicates per time point. At each designated time point, the media was disposed and the cells washed with PBS. The cells were fixed with 1% glutaraldehyde for 20 minutes and then stained with crystal violet for 30 minutes. The plates were blotted and dried overnight. The cells were resuspended with 1% TritonX-100 and shaken for 15 minutes. The absorbance was read on a spectrophotometer at 550 nm. 5-fluorouracil significantly reduced cell number to 60% of the control by 96 hours. Compounds 4H, 11A or 11C did not significantly reduce cell number compared to control by 96 hours (FIG. 26).

Example 14

Compounds 4H, 11a and 11C Significantly Reduce Angiogenic/Inflammatory Factor Secretion from Human Colorectal Tumour Explants To assess the anti-cancer potential of compounds 4H, 11A and 11C we tested their ability to modulate the levels of angiogenic/inflammatory factors secreted from explants cultures of human colorectal cancers. Human colorectal tumour samples were taken directly from the pathology laboratory after surgery once adequate material was taken for diagnostic testing. The tumour samples were washed and stored in DMSO/tumour conditioning media (TCM). The samples were snap-frozen in liquid nitrogen and stored at −80° C. until compound testing was performed.

Prior to compound testing, the tumours were thawed and incubated in fresh TCM for 24 hours. The explants were then treated with 4H, 11A and 11C at 10 µm concentrations for 72 hours. The TCM solutions were collected and stored at −20° C. and the remaining tumour explants were snap-frozen in liquid nitrogen and stored at −80° C. Proteins were extracted from the explants using a nuclear RIPA buffer containing PMSF, sodium orthovandate and protease inhibitors. The explants were homogenised in a PreCellys™ machine. The total protein contents were determined from the resulting lysates using the BCA Assay™. The protein content of each tumour sample was determined using the BCA protein assay. The secretion of angiogenic cytokines was quantified using sandwich ELISA (DuoSet, R&D) for VEGF, ENA-78, MCP-1 and GROα and a multiplex assay (MSD) was used for the inflammatory cytokines: IL-113, TNF, IL-6 and IL-8. The secretion data were normalised according to the tumour sample's protein content.

Figure 27:
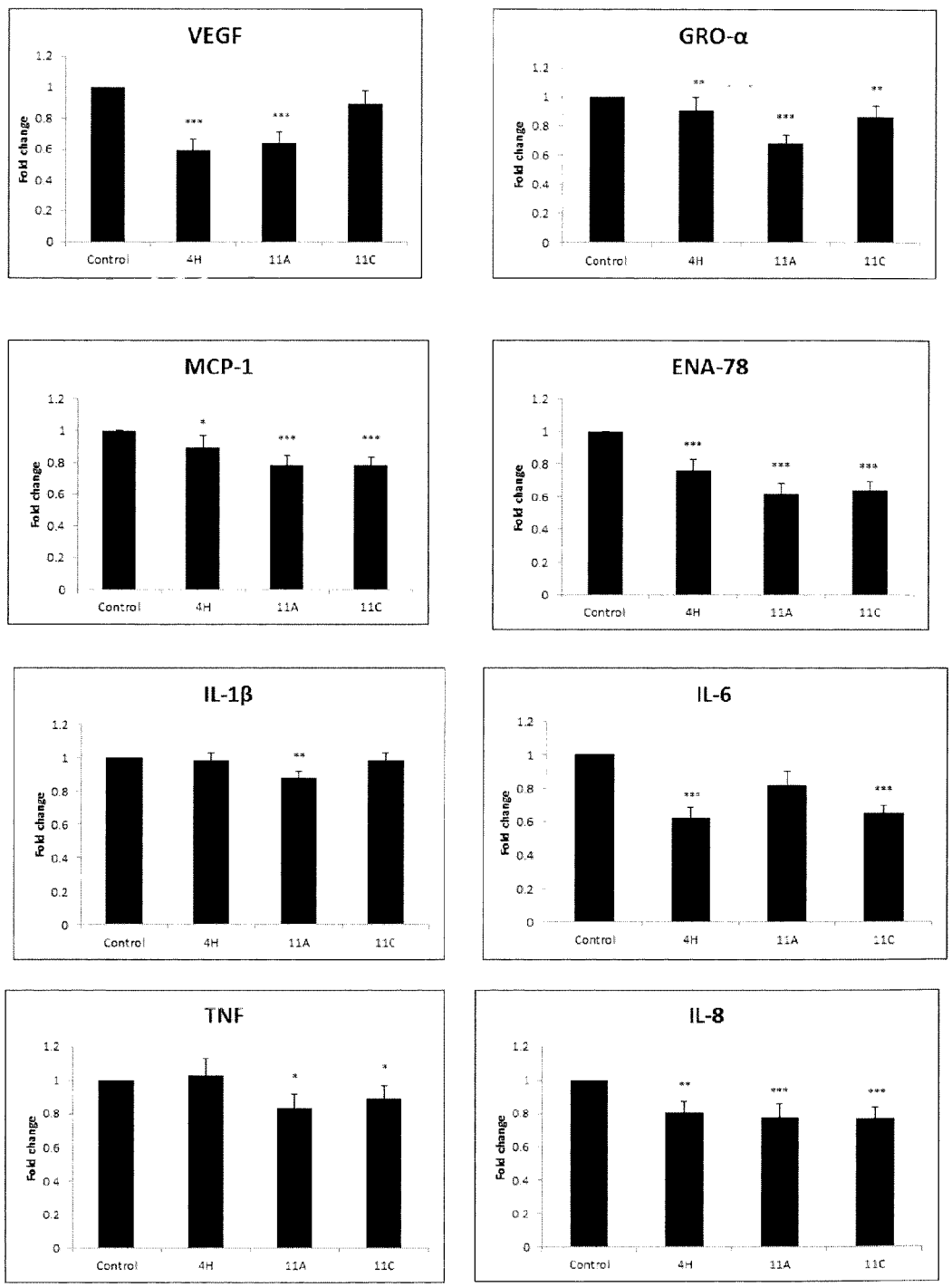
FIG. 27 are graphs showing that compounds 4H, 11A and 11C have significant effects on the levels of specific angiogenic/inflammatory factors secreted from explants cultures of human colorectal cancers. 10 μM 4H significantly reduces the levels of VEGF, GRO-α, MCP-1, ENA-78, IL-6 and IL-8. 10 μM 11A significantly reduces the levels of VEGF, GRO-α, 10 MCP-1, ENA-78, IL-1β TNFα and IL-8. 10 μM 11C significantly reduces the levels of GRO-α, MCP-1, ENA-78, IL-6, TNFα and IL-8. n=40 patients.

Compound 4H significantly reduced the secretion of VEGF, GROα, MCP-1, ENA-78, IL-6 and IL-8 (FIG. 27). Compound 11A significantly reduced the secretion of VEGF, GROα, MCP-1, ENA-78, IL-1β, TNF and IL-8 (FIG. 27). Compound 11C significantly reduced the secretion of GROα, MCP-1, ENA-78, IL-6, TNF and IL-8 (FIG. 27).

Example 15

11B ZHC1 Significantly Reduces Glycolysis of Human OE33P Cells In Vitro

OE33P radiosensitive oesophageal adenocarcinoma cells were used to test the effects of the compound 11B ZHC1 on glycolysis. Cells were maintained in RPMI media supplemented with 10% foetal calf serum, penicillin (100 U/ml) and streptomycin (100 μg/ml). A total of 11,000 cells, in 100 μl media, were seeded per well in 24 well plates and left to incubate for 24 hours, with an additional 150 μl media added after 5 hours. The media was replaced with solutions containing 10 μM of 11B ZHC1 or fresh media as a control. Each treatment had 6 replicates. After 24 hours of treatment, media was replaced with modified DMEM supplemented with 0.5 mM glucose. Rates of glycolysis were determined using Seahorse Biosciences metabolism technology. The media was disposed and the cells washed with PBS. The cells were fixed with 1% glutaraldehyde for 15 minutes and then stained with crystal violet for 30 minutes. The plates were blotted and dried overnight. The cells were resuspended with 1% TritonX-100 and shaken for 15 minutes. The absorbance was read on a spectrophotometer at 590 nm. Rates of glycolysis were then normalised to cell number. No changes in ECAR were detected in OE33R treated cells.

Example 16

11B_Z_HCl Did not Significantly Reduce the Number in Human OE33P and OE33R Cells In Vitro after 24 Hours OE33P radiosensitive and OE33R radioresistant cells were used to test the effects of the compound 11B_Z_HCl on toxicity. Cells were maintained in RPMI media supplemented with 10% foetal calf serum, penicillin (100 U/ml) and streptomycin (100 μg/ml). A total of 11,000 cells, in 100 μl media, were seeded per well in 24 well plates and left to incubate for 24 hours, with an additional 150 μl media added after 5 hours. The media was replaced with solutions containing 10 μM of 11B_Z_HCl or fresh media as a control. Each treatment had 6 replicates. After 24 hours of treatment, the cells were fixed with 1% glutaraldehyde for 15 minutes and then stained with crystal violet for 30 minutes. The plates were blotted and dried overnight. The cells were resuspended with 1% TritonX-100 and shaken for 15 minutes. The absorbance was read on a spectrophotometer at 590 nm.

Example 17

11B_Z_HCl Significantly Reduces Oxidative Phosphorylation in Human OE33P and OE33R Cells In Vitro OE33P radiosensitive and OE33R radioresistant oesophageal adenocarcinoma cells were used to test the effects of the compound 11B_Z_HCl on oxidative phosphorylation. Cells were maintained in RPMI media supplemented with 10% foetal calf serum, penicillin (100 U/ml) and streptomycin (100 μg/ml). A total of 11,000 cells, in 100 μl media, were seeded per well in 24 well plates and left to incubate for 24 hours, with an additional 150 μl media added after 5 hours. The media was replaced with solutions containing 10 μM of 11B_Z_HCl or fresh media as a control. Each treatment had 6 replicates. After 24 hours of treatment, media was replaced with modified DMEM supplemented with 0.5 mM glucose. Rates of oxidative phosphorylation were determined using Seahorse Biosciences metabolism technology. Rates of oxidative phosphorylation were then normalised to cell number.

Example 18

Surviving Fraction of Human OE33P and OE33R Cells In Vitro when Cells were Treated with 11B_Z_HCl OE33P radiosensitive and OE33 radioresistant oesophageal adenocarcinoma cells were used to test the effects of the compound 11B_Z_HCl on cell survival. Cells were maintained in RPMI media supplemented with 10% foetal calf serum, penicillin (100 U/ml) and streptomycin (100 μg/ml). Cells were seeded in 6 well plates and left to incubate for 24 hours. The media was replaced with solutions containing 10 μM of 11B_Z_HCl or fresh media as a control. After 24 hours of treatment, media was replaced. When control colonies had grown sufficiently large, the media was disposed and the cells washed with PBS. The cells were fixed with methanol and stained with crystal violet. Surviving fraction, the ability of the cells to form colonies was then determined.

Example 19

Surviving Fraction of Human OE33P and OE33R Cells In Vitro when Cells were Treated with 11B ZHC1 Prior to Irradiation OE33P radiosensitive and OE33 radioresistant oesophageal adenocarcinoma cells were used to test the effects of the compound 11B_Z_HCl on cell survival. Cells were maintained in RPMI media supplemented with 10% foetal calf serum, penicillin (100 U/ml) and streptomycin (100 μg/ml). Cells were seeded in 6 well plates and left to incubate for 24 hours. The media was replaced with solutions containing 10 μM of 11B_Z_HCl or fresh media as a control. After 24 hours of treatment, media was replaced and cells were subjected to 2Gy radiation. When control colonies had grown sufficiently large, the media was disposed and the cells washed with PBS. The cells were fixed with methanol and stained with crystal violet. Surviving fraction, the ability of the cells to form colonies was then determined.

Example 20

Surviving Fraction of Human OE33P and OE33R Cells In Vitro when Cells were Treated with 11B_Z_HCl Following Irradiation OE33P radiosensitive and OE33 radioresistant oesophageal adenocarcinoma cells were used to test the effects of the compound 11B_Z_HCl on cell survival. Cells were maintained in RPMI media supplemented with 10% foetal calf serum, penicillin (100 U/ml) and streptomycin (100 μg/ml). Cells were seeded in 6 well plates and left to incubate for 24 hours. The cells were subjected to 2Gy radiation and the media was replaced with solutions containing 10 μM of 11B_Z_HCl or fresh media as a control. After 24 hours of treatment, media was replaced. When control colonies had grown sufficiently large, the media was disposed and the cells washed with PBS. The cells were fixed with methanol and stained with crystal violet. Surviving fraction, the ability of the cells to form colonies was then determined.

Example 21

Surviving Fraction of Human OE33P and OE33R Cells In Vitro when Cells were Treated with 11B HCl and 11B_CC11_HCl Following Irradiation OE33P radiosensitive and OE33R radioresistant oesophageal adenocarcinoma cells were used to test the effects of the compound 11B_Z_HCl on cell survival. Cells were maintained in RPMI media supplemented with 10% foetal calf serum, penicillin (100 U/ml) and streptomycin (100 µg/ml). Cells were seeded in 6 well plates and left to incubate for 24 hours. The cells were subjected to 2Gy irradiation and the media was replaced with solutions containing 10 µM of 11B_Z_HCl or fresh media as a control. After 24 hours of treatment, media was replaced. When control colonies had grown sufficiently large, the media was disposed and the cells washed with PBS. The cells were fixed with methanol and stained with crystal violet. Surviving fraction, the ability of the cells to form colonies was then determined.

Example 22

Reduction in the Expression of DNA Repairs in OE33P and OE33R Cells In Vitro when Cells were Treated with 11B HCl, 11B_CC11_HCl and 11B_Z_HCl OE33P radiosensitive and OE33R radioresistant oesophageal adenocarcinoma cells were used to test the effects of the above compounds on the gene expression of DNA repair proteins. Cells were maintained in RPMI media supplemented with 10% foetal calf serum, penicillin (100 U/ml) and streptomycin (100 µg/ml). Cells were seeded in 6 well plates and left to incubate for 24 hours. Cells were treated 10 µM of the above compounds or fresh media as a control. After 24 hours of treatment, RNA and cDNA was isolated and qPCR performed using primer probes to the following primer probes to RAD51L3, MMS19, SMUG1, PARP1 and MLH1.

Example 23

OE33P radiosensitive and OE33R radioresistant oesophageal adenocarcinoma cells were used to test the effects of compounds 11B HCl, 11B_CC11_HCl and 11B_Z_HCL on the gene expression of DNA repair proteins. Cells were maintained in RPMI media supplemented with 10% foetal calf serum, penicillin (100 U/ml) and streptomycin (100 µg/ml). Cells were seeded in 6 well plates and left to incubate for 24 hours. Cells were treated 10 µM of the above compounds or fresh media as a control. After 24 hours of treatment, RNA and cDNA was isolated and qPCR performed using primer probes to the following primer probes to RAD51L3, MMS19, SMUG1, PARP1 and MLH1.

Oesophageal Cancer is the $6^{th}$ most common cause of cancer related deaths worldwide. Globally, there has been a dramatic epidemiological increase in the incidence of oesophageal adenocarcinoma (OAC), with Ireland showing a 48% increase in incidence rates over the last 3 years. Rising increase in obesity levels strongly correlates with the dramatic increases in the number of OAC cases. 5 year survival rates are approximately 10%. Treatment options for these patients are limited. 70% of OAC patients receive a treatment called 'neoadjuvant treatment' meaning they will be treated with a combination of radiation and chemotherapy prior to their surgery. The goal of this treatment is to downsize the tumour in order to make surgery more successful. This is a 6 week treatment that can have many negative side effects for the patients. Unfortunately, only approximately 75% of the patients will respond to this treatment. Therefore approximately 75% of patients receive this treatment, suffer the negative side effects and importantly they will experience a significant delay to surgery which may impact on their overall survival rates. These patients are referred to as 'non responders' Work done by the Department of Surgery at Trinity College Dublin (J Mol Med (2012) 90:1449-1458) has shown that these non responders show high levels of metabolism (energy production) and high levels of DNA repair protein expression. The high level of DNA repair protein expression tries to repair the damaged DNA following radiation and therefore prevents the radiated cells from undergoing cell death.

We have found that the compounds described above can reduce metabolism rates and expression of DNA repair proteins in cancer cells, resulting in a reduced number of surviving cancer cells. These compounds may have clinical utility in not only non responders but also for those tumours that are sensitive to radiation, they may further increase response in this subset of patients also. This neoadjuvant treatment is not specific to OAC; it also applies to colorectal cancer and breast cancer.

The disclosures of the various references mentioned this specification are hereby incorporated by reference in their entirety.

The invention is not limited to the embodiments hereinbefore described, accompanying which may be varied in detail.

REFERENCES

Alvarez Y, Astudillo O, Jensen L, Reynolds A L, Waghorne N, Brazil D P, Cao Y, O'Connor J J, Kennedy B N. 2009. Selective inhibition of retinal angiogenesis by targeting P13 kinase. PLoS One 4:e7867.
Alvarez Y, Cederlund M L, Cottell D C, Bill B R, Ekker S C, Torres-Vazquez J, Weinstein B M, Hyde D R, Vihtelic T S, Kennedy B N. 2007. Genetic determinants of hyaloid and retinal vasculature in zebrafish. BMC Dev Biol 7:114.
Bergers G, Benjamin L E. 2003. Tumorigenesis and the angiogenic switch. Nat Rev Cancer 3:401-410.
Bergers G, Hanahan D. 2008. Modes of resistance to anti-angiogenic therapy. Nat Rev Cancer 8:592-603.
Brockerhoff S E. 2006. Measuring the optokinetic response of zebrafish larvae. Nat Protoc 1:2448-2451.
Carmeliet P. 2005. VEGF as a key mediator of angiogenesis in cancer. Oncology 69 Suppl 3:4-10.
Culy C. 2005. Bevacizumab: antiangiogenic cancer therapy. Drugs Today (Barc) 41:23-36.
den Hertog J. 2005. Chemical genetics: Drug screens in Zebrafish. Biosci Rep 25:289-297.
Doukas J, Mahesh S, Umeda N, Kachi S, Akiyama H, Yokoi K, Cao J, Chen Z, Dellamary L, Tam B, Racanelli-Layton A, Hood J, Martin M, Noronha G, Soll R, Campochiaro P A. 2008. Topical administration of a multi-targeted kinase inhibitor suppresses choroidal neovascularization and retinal edema. J Cell Physiol 216:29-37.
Ellis L M. 2003. Antiangiogenic therapy at a crossroads: clinical trial results and future directions. J Clin Oncol 21: 281s-283s.

Ferrara N. Vascular endothelial growth factor and age-related macular degeneration: from basic science to therapy. Nat Med 16:1107-1111.

Ferrara N, Kerbel R S. 2005. Angiogenesis as a therapeutic target. Nature 438:967-974

Frank R N. 2004. Diabetic retinopathy. N Engl J Med 350: 48-58.

Goldsmith P. 2004. Zebrafish as a pharmacological tool: the how, why and when. Curr Opin Pharmacol 4:504-512.

He A R, Marshall J. 2005. Biologic therapy for colon cancer. Clin Adv Hematol Oncol 3:555-561.

Jager R D, Mieler W F, Miller J W. 2008. Age-related macular degeneration. N Engl J Med 358:2606-2617.

Kleinman M E, Yamada K, Takeda A, Chandrasekaran V, Nozaki M, Baffi J Z, Albuquerque R J, Yamasaki S, Itaya M, Pan Y, Appukuttan B, Gibbs D, Yang Z, Kariko K, Ambati B K, Wilgus T A, DiPietro L A, Sakurai E, Zhang K, Smith J R, Taylor E W, Ambati J. 2008. Sequence- and target-independent angiogenesis suppression by siRNA via TLR3. Nature 452:591-597.

MacRae C A, Peterson R T. 2003. Zebrafish-based small molecule discovery. Chem Biol 10:901-908.

Mandala M, Ferretti G, Barni S. 2004. Oxaliplatin in colon cancer. N Engl J Med 351:1691-1692; author reply 1691-1692.

Narayanan R, Kuppermann B D, Jones C, Kirkpatrick P. 2006. Ranibizumab. Nat Rev Drug Discov 5:815-816.

Peterson R T, Shaw S Y, Peterson T A, Milan D J, Zhong T P, Schreiber S L, MacRae C A, Fishman M C. 2004. Chemical suppression of a genetic mutation in a zebrafish model of aortic coarctation. Nat Biotechnol 22:595-599.

Pichler F B, Laurenson S, Williams L C, Dodd A, Copp B R, Love D R. 2003. Chemical discovery and global gene expression analysis in zebrafish. Nat Biotechnol 21:879-883.

Rattner A, Nathans J. 2006. Macular degeneration: recent advances and therapeutic opportunities. Nat Rev Neurosci 7:860-872.

Takahashi K, Saishin Y, Saishin Y, King A G, Levin R, Campochiaro P A. 2009. Suppression and regression of choroidal neovascularization by the multitargeted kinase inhibitor pazopanib. Arch Ophthalmol 127:494-499.

Wong S F. 2005. Cetuximab: an epidermal growth factor receptor monoclonal antibody for the treatment of colorectal cancer. Clin Ther 27:684-694.

Zon L I, Peterson R T. 2005. In vivo drug discovery in the zebrafish. Nat Rev Drug Discov 4:35-44.

The invention claimed is:

1. A compound selected from:

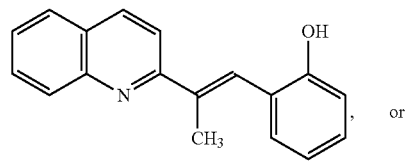

Structure IV

, or

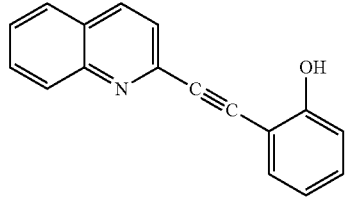

Structure VI and salts thereof.

2. The compound as claimed in claim 1 wherein the salt is a HCl salt.

3. A pharmaceutical composition comprising one or more compound selected from:

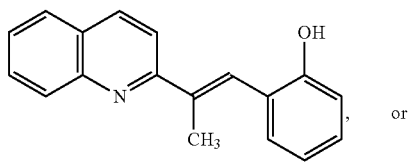

Structure IV

, or

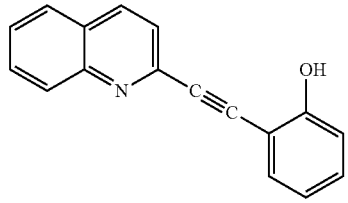

Structure VI and salts thereof.

4. The composition as claimed in claim 3 wherein the salt is a HCl salt of the compound.

5. The composition as claimed in claim 3 further comprising a pharmaceutically acceptable excipient.

6. The composition as claimed in claim 3 in a form for topical administration.

7. The composition as claimed in claim 3 in the form of eye drops.

8. The composition as claimed in claim 3 in a form for systemic administration.

9. The composition as claimed in claim 3 in the form of an injectable solution or suspension.

10. A method for the treatment of an angiogenesis related disease or disorder comprising the step of administering a compound of structure IV or VI or a salt thereof

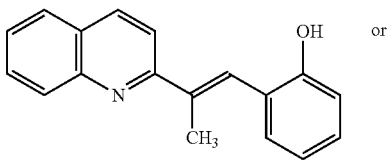

Structure IV or

-continued

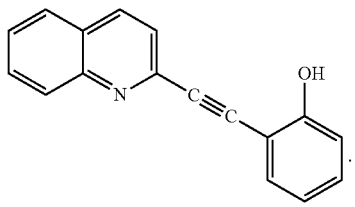

Structure VI

11. The method as claimed in claim 10 wherein the angiogenesis-related disease or disorder is associated with neovascularisation of the eye.

12. The method as claimed in claim 10 wherein the angiogenesis-related disease or disorder is associated with blindness.

13. The method as claimed in claim 10 wherein the angiogenesis-related disease or disorder is age-related. macular degeneration or diabetic retinopathy.

14. The method as claimed in claim 13 wherein the age-related macular degeneration is wet age-related macular degeneration.

15. The method as claimed in claim 10 wherein the angiogenesis-related disease or disorder is cancer.

16. The method as claimed in claim 15 wherein the cancer is a solid tumour forming cancer.

17. The method as claimed in claim 15 wherein the cancer is colorectal cancer.

18. The method as claimed in claim 15 wherein the cancer is oesophageal cancer.

19. The method as claimed in claim 15 wherein the cancer is breast cancer.

20. The method as claimed in claim 10 wherein the angiogenesis-related disease or disorder is diabetic retinopathy.

\* \* \* \* \*